(12) United States Patent
Strop et al.

(10) Patent No.: US 10,941,216 B2
(45) Date of Patent: *Mar. 9, 2021

(54) ENGINEERED POLYPEPTIDE CONJUGATES AND METHODS FOR MAKING THEREOF USING TRANSGLUTAMINASE

(71) Applicants: PFIZER INC., New York, NY (US); RINAT NEUROSCIENCE CORP., South San Francisco, CA (US)

(72) Inventors: Pavel Strop, San Mateo, CA (US); Magdalena Grazyna Dorywalska, Redwood City, CA (US); Arvind Rajpal, San Francisco, CA (US); David Shelton, Oakland, CA (US); Shu-Hui Liu, Redwood City, CA (US); Jaume Pons, San Bruno, CA (US); Russell Dushin, Old Lyme, CT (US)

(73) Assignee: Pfizer Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/593,259

(22) Filed: May 11, 2017

(65) Prior Publication Data

US 2017/0313787 A1 Nov. 2, 2017

Related U.S. Application Data

(62) Division of application No. 13/883,535, filed as application No. PCT/IB2011/054899 on Nov. 3, 2011, now Pat. No. 9,676,871.

(60) Provisional application No. 61/410,840, filed on Nov. 5, 2010, provisional application No. 61/553,917, filed on Oct. 31, 2011.

(51) Int. Cl.
| | |
|---|---|
| *A61K 47/68* | (2017.01) |
| *C07K 16/00* | (2006.01) |
| *C07K 17/02* | (2006.01) |
| *A61P 43/00* | (2006.01) |
| *C07K 16/30* | (2006.01) |

(52) U.S. Cl.
CPC .............. *C07K 17/02* (2013.01); *A61K 47/68* (2017.08); *A61K 47/6803* (2017.08); *A61K 47/6851* (2017.08); *A61K 47/6889* (2017.08); *C07K 16/30* (2013.01); *C07K 2317/31* (2013.01); *C07K 2317/73* (2013.01)

(58) Field of Classification Search
CPC .... C07K 17/02; C07K 16/30; C07K 2317/73; C07K 2317/31; A61K 47/6851; A61K 47/6889; A61K 47/6803; A61K 47/68; A61P 43/00

See application file for complete search history.

(56) References Cited

U.S. PATENT DOCUMENTS

| 6,919,076 | B1 | 7/2005 | Green et al. |
| 7,375,078 | B2* | 5/2008 | Feng ................... C07D 277/46 514/1.3 |
| 7,521,541 | B2 | 4/2009 | Eigenbrot et al. |
| 8,871,908 | B2 | 10/2014 | Liu et al. |
| 9,399,074 | B2 | 7/2016 | Liu et al. |
| 2003/0138785 | A1* | 7/2003 | Kopytek ............. C07D 475/08 435/6.13 |
| 2007/0184537 | A1 | 8/2007 | Schibli et al. |
| 2008/0279868 | A1 | 11/2008 | Boyd et al. |
| 2016/0257746 | A1 | 9/2016 | Liu et al. |

FOREIGN PATENT DOCUMENTS

| EP | 0725145 A1 | 8/1996 |
| WO | 00/43492 A2 | 7/2000 |
| WO | 0044788 A1 | 8/2000 |
| WO | 2009/059278 A1 | 5/2009 |
| WO | 2010/002042 A1 | 1/2010 |
| WO | 2010/011096 A2 | 1/2010 |
| WO | 2010/080124 A2 | 7/2010 |
| WO | 2011/069164 A2 | 6/2011 |
| WO | 2011/090305 A2 | 7/2011 |
| WO | 2011/090306 A2 | 7/2011 |
| WO | 2011/122922 A2 | 10/2011 |

OTHER PUBLICATIONS

Rudikoff et al., PNAS 79: 1979-1983 (Year: 1982).*
Kussie et al., J. Immunol. 152: 146-152 (Year: 1994).*
Chen et al., EMBO J., 14: 2784-2794 (Year: 1995).*
Tanizawa et al., Journal of the National Cancer Institute 86(11): 836-842 (Year: 1994).*
Jeger et al., Angew Chem Int Ed 49: 9995-9997 (Year: 2010).*
MGT Scientific Chart, pp. 1-4 (Year: 2017).*
Carter, P., "Bispecific human IgG by design", Journal of Immunological Methods, 2001, 248(1-2): 7-15.

(Continued)

*Primary Examiner* — Phuong Huynh
(74) *Attorney, Agent, or Firm* — Jenny J. Yeh; Susan L. Wang

(57) ABSTRACT

The present invention provides engineered polypeptide conjugates (e.g., antibody-drug-conjugates, toxin-(biocompatible polymer) conjugates, antibody-(biocompatible polymer) conjugates, and bispecific antibodies) comprising acyl donor glutamine-containing tags and amine donor agents. In one aspect, the invention provides an engineered Fc-containing polypeptide conjugate comprising the formula (Fc-containing polypeptide)-T-A, wherein T is an acyl donor glutamine-containing tag engineered at a specific site or comprises an endogenous glutamine made reactive by the Fc-containing polypeptide engineering, wherein A is an amine donor agent, and wherein the amine donor agent is site-specifically conjugated to the acyl donor glutamine-containing tag or the endogenous glutamine. The invention also provides methods of making engineered polypeptide conjugates using transglutaminase.

6 Claims, 14 Drawing Sheets

Specification includes a Sequence Listing.

(56) References Cited

OTHER PUBLICATIONS

Doronina, S.O., et al., "Novel Peptide Linkers for Highly Potent Antibody-Auristatin Conjugate", Bioconjugate Chemistry, 2008, 19(10): 1960-1963.
Fontana, A., et al., "Site-specific modification and PEGylation of pharmaceutical proteins mediated by transglutaminase", Advanced Drug Delivery Reviews, 2008, 60(1): 13-28.
Gentle, I.E., et al., "Direct Production of Proteins with N-Terminal Cysteine for Site-Specific Conjugation", Bioconjugate Chemistry, 2004, 15(3): 658-663.
Gomez, N., et al., "Triple Light Chain Antibodies: Factors That Influence Its Formation in Cell Culture", Biotechnology and Bioengineering, 2010 (pub'd online Oct. 20, 2009) 105(4): 748-760.
International Search Report dated Sep. 28, 2012 for PCT Application No. PCT/IB2011/054899 filed Nov. 3, 2011, nine pages.
Written Opinion of the International Searching Authority for PCT Application No. PCT/IB2011/054899 filed Nov. 3, 2011, 11 pages.
Jeger, S., et al., "Site-Specific and Stoichiometric Modification of Antibodies by Bacterial Transglutaminase", Angewandte Chemie, 2010, 49(51): 9995-9997.
Josten, A., et al., "Use of microbial transglutaminase for the enzymatic biotinylation of antibodies", Journal of Immunological Methods, 2000, 240(1-2): 47-54.
Junutula, J.R., et al., "Site-specific conjugation of a cytotoxic drug to an antibody improves the therapeutic index", Nature Biotechnology, 2008, 26(8): 925-932.
Kamiya, N., et al., "Site-specific cross-linking of functional proteins by transglutamination", Enzyme and Microbial Technology, 2003, 33(4): 492-496.
Lin, C., et al., "Transglutaminase-Catalyzed Site-Specific Conjugation of Small-Molecule Probes to Proteins in Vitro and on the Surface of Living Cells", Journal of American Chemical Society, 2006, 128(14): 4542-4543.
Mero, A., et al., "Transglutaminase-Mediated PEGylation of Proteins: Direct Identification of the Sites of Protein Modification by Mass Spectrometry using a Novel Monodisperse PEG", Bioconjugate Chemistry, 2009, 20(2): 384-389.
Mindt, T.L., et al., "Modification of Different IgG1 Antibodies via Glutamine and Lysine using Bacterial and Human Tissue Transglutaminase", Bioconjugate Chemistry, 2008, 19(1): 271-278.
Meusel, M., et al., "Synthesis of Hapten-Protein Conjugates using Microbial Transglutaminase", Methods in Molecular Biology, 2004, 283: 109-123.
Ohtsuka, T., et al., "Comparison of Substrate Specificities of Transglutaminases Using Synthetic Peptides as Acyl donors", Bioscience, Biotechnology, and Biochemistry, 2000, 64(12): 2608-2613.
Russell, D., et al., "Transglutaminase may mediate certain physiological effects of endogenous amines and of amine-containing therapeutic agents", Life Sciences, 1982, 30(18): 1499-1508.
Sato, H., et al., "Enzymatic procedure for site-specific pegylation of proteins", Advanced Drug Delivery Reviews, 2002, 54: 487-504.
Takazawa, T., et al., "Enzymatic Labeling of a Single Chain Variable Fragment of an Antibody With Alkaline Phosphatase by Microbial Transglutaminase", Biotechnology and Bioengineering, 2004, 86(4): 399-404.
Tanaka, T., et al., "Peptidyl Linkers for Protein Heterodimerization Catalyzed by Microbial Transglutaminase", Bioconjugate Chemistry, 2004, 15(3): 481-497.
Tanaka, T., et al., "N-terminal glycine-specific protein conjugation catalyzed by microbial transglutaminase", FEBS Letters, 2005, 579(10): 2092-2096.
Veronese, F., et al., "PEGylation, successful approach to drug delivery", Drug Discovery Today, 2005, 10(21): 1451-1458.
Plagmann, I., et al., "Transglutaminase-catalyzed covalent multimerization of camelidae anti-human TNF single domain antibodies improves neutralizing activity," 2009, Journal of Biotechnology, 170-178, vol. 142, No. 2.

\* cited by examiner

| HCQ01 | ...LSLSPG_-LLQGG (SEQ ID NO:15) |
| HCQ02 | ...LSLSPG_-LLQG (SEQ ID NO:16) |
| HCQ03 | ...LSLSQG_-G (SEQ ID NO:17) |
| HNQ01 | GLL-QVQLKE... (SEQ ID NO:18) |
| HNQ02 | LL-QVQLKE...(SEQ ID NO:19) |
| HNQ03 | GL-_VQLKE... (SEQ ID NO:20) |
| HNQ04 | L-_VQLKE... (SEQ ID NO:21) |
| LCQ01 | ...FNRGEC-GGGLLQGG (SEQ ID NO:22) |
| LCQ02 | ...FNRGEC-LLQGG (SEQ ID NO:23) |
| LNQ01 | GLLQG-DIVLT... (SEQ ID NO:24) |
| LNQ02 | LLQ-_IVLT... (SEQ ID NO:25) |

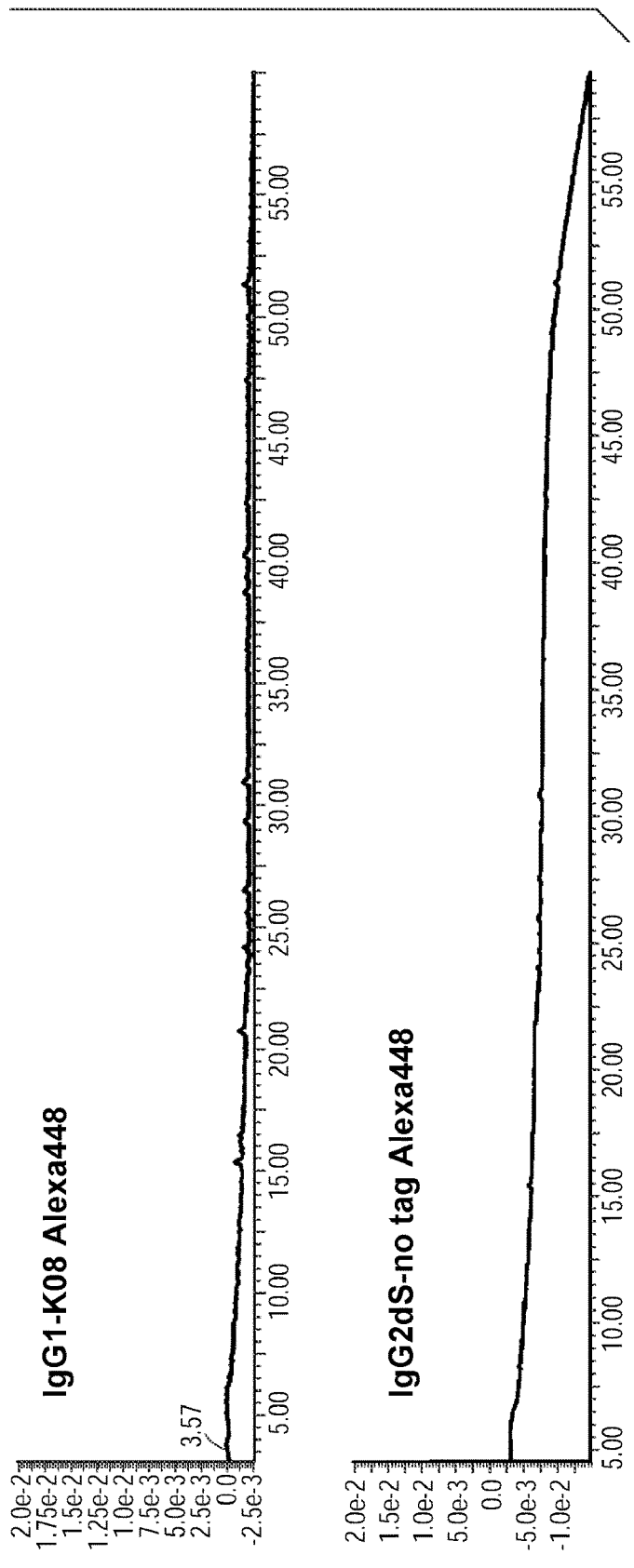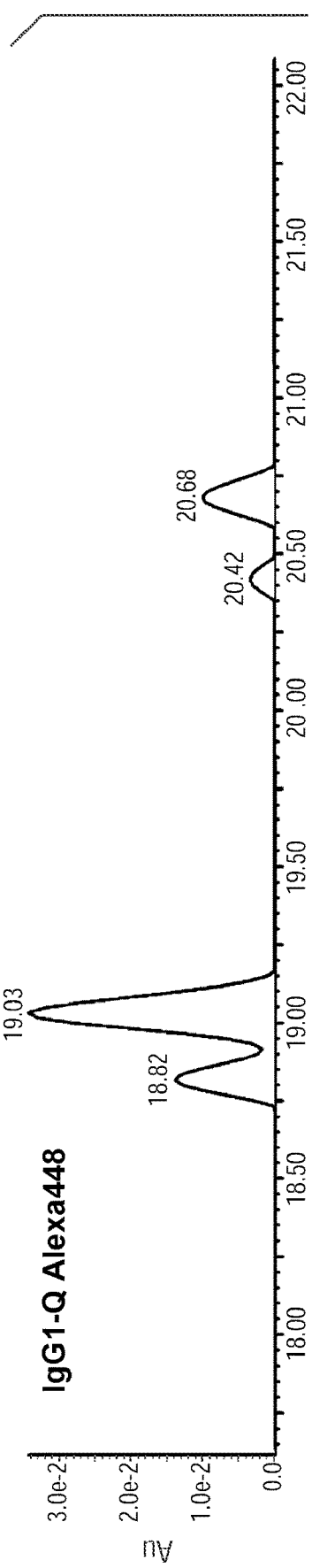
FIG. 8A-2
FIG. 8B-1

ENGINEERED POLYPEPTIDE CONJUGATES AND METHODS FOR MAKING THEREOF USING TRANSGLUTAMINASE

RELATED APPLICATIONS

This application is a divisional of U.S. application Ser. No. 13/883,535 (now U.S. Pat. No. 9,676,871), which is a national stage of PCT international application No. PCT/IB2011/054899, filed Nov. 3, 2011, which claims the benefit of U.S. Provisional Application No. 61/410,840 filed Nov. 5, 2010, and U.S. Provisional Application No. 61/553,917 filed Oct. 31, 2011, which are hereby incorporated by reference in their entireties.

REFERENCE TO SEQUENCE LISTING

This application is being filed electronically via EFS-Web and includes an electronically submitted sequence listing in .txt format. The .txt file contains a sequence listing entitled "PC71673B_SEQListing_ST25.txt" created on May 11, 2017, and having a size of 16 KB. The sequence listing contained in this .txt file is part of the specification and is incorporated herein by reference in its entirety.

FIELD OF THE INVENTION

The field of this invention relates generally to engineered polypeptide conjugates (e.g., antibody-drug-conjugates, toxin-(biocompatible polymer) conjugates, antibody-(biocompatible polymer) conjugates, and bispecific antibodies) comprising acyl donor glutamine-containing tags and amine donor agents. The invention also relates to methods for making such engineered polypeptide conjugates using transglutaminase.

BACKGROUND OF THE INVENTION

Antibody therapy provides targeted therapeutic treatment in patients with various disorders, such as cancers and immunological diseases, and therefore has played an important role in biological research. Different approaches of targeted antibody therapy, such as antibody-drug conjugates (ADC) and engineered bispecific antibodies, have been explored. See, e.g., Doronian et al., *Bioconjuage Chem.* 19:1960-1963 (2008); Junutula et al., *Nature Biotechnology* 26: 925-932 (2008); and Carter, P. *J. Immunol. Methods* 248(1-2):7-15 (2001).

In the case of antibody-drug conjugates (i.e., immunoconjugates), cytotoxic drugs are generally linked or conjugated to antibodies for targeted local delivery of the drug moieties to tumors. Chemical modification has been widely used for conjugating drugs to antibodies either through lysine side chain amines or through cysteine sulfhydryl groups activated by reducing interchain disulfide bonds. However, these types of "residue-specific" conjugation lead to a heterogeneous mixture of conjugates having different molar ratios of drug to antibody, different and non-specific conjugation sites, different efficiency, safety, and pharmacokinetics, and different clearance of antibody-drug conjugates. See Tanaka et al, *FEBS Letters* 579:2092-2096 (2005). Further, inclusion bodies or incorrect disulfide bridges may also be formed in cysteine-introduced antibodies. See, e.g., Gentle et al., *Bioconjugate Chem.* 15:658-663 (2004). Reactive cysteine residues engineered at specific sites of antibodies (e.g., THIOMAB) for specific drug conjugation with defined stoichiometry has also been explored. See Junutula et al., *Nature Biotechnology*, 26: 925-932 (2008). However, expression and conjugation of such cysteine engineered antibodies and antibody-drug conjugates are complicated processes which require lengthy reaction procedures (e.g., reductions and oxidations). See, e.g., Gomez et al., *Biotechnology and Bioengineering*, 105(4): 748-760 (2009). Antibody aggregates may also be generated during the process of making the cysteine engineered antibodies and the antibody-drug conjugates.

Enzymatic approaches using a transglutaminase for protein conjugation have been explored recently as an alternative to "residue-specific" conjugation of antibodies/proteins and drugs. Transglutaminases (EC2.3.2.13; protein-glutamine:gamma-glutamyltransferse; protein-glutamine:amine γ-glutamyltransferase; CAS 80146-85-6) belong to a family of enzymes that catalyze the acyl addition to a primary amine wherein the gamma-carboxamide group of peptide-bound γ-glutanyl residue is the acyl donor and the primary amine is the acyl acceptor and the amine donor. Transglutaminases have been used, for example, for the attachment of proteins to proteins. See, e.g., Tanaka et al, *FEBS Letters* 579:2092-2096 (2005). Enzymatic modification of antibodies using transglutaminases has also been reported. See Josten et al. *J. of Immunological Methods* 240:47-54 (2000); Takazawa et al., *Biotechnology and Bioengineering* 86(4): 399-404 (2004); and Mindt et al., *Bioconjugate Chem* 19:271-27 (2008). Protein conjugation or modification using transglutaminase provides the advantages of high selectivity, simplified reaction procedures, and mild reaction conditions. However, to date, because of the substrate specificity of transglutaminase, site-specific conjugation of antibodies and proteins mediated by a transglutaminase has not been clearly established. Accordingly, more efficient methods for generating a site-specific and homogenous antibody-drug conjugate, antibody conjugate, or protein conjugate using transglutaminase are needed.

All publications, patents, and patent applications cited herein are hereby incorporated by reference herein in their entirety for all purposes to the same extent as if each individual publication, patent, and patent application were specifically and individually indicated to be so incorporated by reference. In the event that one or more of the incorporated literature and similar materials differs from or contradicts this application, including but not limited to defined terms, term usage, described techniques, or the like, this application controls.

BRIEF SUMMARY OF THE INVENTION

The present invention provides engineered polypeptide conjugates (e.g., Fc-containing polypeptide-drug-conjugates, bispecific antibodies, Fab-containing polypeptide-biocompatible polymer-conjugates, and toxin-biocompatible polymer conjugates) and methods for making thereof using transglutaminase. The inventors have discovered that an Fc-containing polypeptide engineered with an acyl donor glutamine-containing tag (e.g., Gln-containing peptide tags or Q-tags) or an endogenous glutamine made reactive by polypeptide engineering (e.g., via amino acid deletion, insertion, substitution, or mutation on the polypeptide), in the presence of transglutaminase, can covalently crosslink with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine. The conjugation efficiency of the Fc-containing polypeptide engineered with an acyl donor glutamine-containing tag (or the reactive endogenous glutamine) and the amine donor agent is at least about 51%, and the conjugation efficiency between the Fc-containing polypeptide and the amine donor agent is less than about 5% in the absence of an acyl donor glutamine-containing tag or the accessible/exposed/reactive endogenous glutamine. For example, deletion or mutation of the last amino acid from Lys (lysine) to another amino acid in the Fc-containing polypeptide spatially adjacent to the Gln-containing peptide tag provides a significant increase in conjugation efficiency of the Fc-containing polypeptides and the small molecule (e.g., a cytotoxic agent or an imaging agent). The inventors have further discovered that, in the presence of transglutaminase, a stable and homogenous population of bispecific antibody can be generated using a Gln-containing peptide tag engineered to a first Fc-containing polypeptide directed to an epitope and another peptide tag (e.g., a Lys containing polypeptide tag) engineered to a second Fc-containing polypeptide directed to a second epitope in reducing environment. A similar bispecific antibody can also be made by combining two different Fc-containing polypeptides engineered to two Gln-containing peptide tags with a diamine. The inventors have further discovered that, in the presence of transglutaminase, a stable and homogenous Fab-containing polypeptide conjugate or a toxin polypeptide conjugate with longer half life can be made by covalently reacting a Gln-containing peptide tag engineered to a Fab-containing polypeptide or a toxin polypeptide with a biocompatible polymer. Further, the selection of the acyl donor glutamine-containing tags, Fc-containing polypeptides, and/or the amine donor agents as described herein allows for site-specific conjugation.

In one aspect, the invention provides an engineered Fc-containing polypeptide conjugate comprising the formula: (Fc-containing polypeptide)-T-A, wherein T is an acyl donor glutamine-containing tag engineered (e.g., via insertion or replacement/substitution of one or more wild-type amino acid(s)) at a specific site or comprises an endogenous glutamine made reactive (i.e., the ability to form a covalent bond as an acyl donor in the presence of an amine and a transglutaminase) by the Fc-containing polypeptide engineering; wherein A is an amine donor agent; and wherein the amine donor agent is site-specifically conjugated to the acyl donor glutamine-containing tag at a carboxyl terminus, an amino terminus, or at an another site in the Fc-containing polypeptide.

In some embodiments, the acyl donor glutamine-containing tag is not spatially adjacent to a reactive Lys (i.e., the ability to form a covalent bond as an amine donor in the presence of an acyl donor and a transglutaminase) in the Fc-containing polypeptide.

In some embodiments, the acyl donor glutamine-containing tag engineering or the Fc-containing polypeptide engineering is an amino acid deletion, insertion, substitution, mutation, or any combination thereof. In some embodiments, the acyl donor glutamine-containing tag engineering or the Fc-containing polypeptide engineering is not at an amino acid substitution from asparagines (Asn) to glutamine at position 297 of human IgG (Kabat numbering scheme).

In some embodiments, the amine donor agent has the formula: X-Y-Z, wherein X is an amine donor unit, Y is a linker, and Z is an agent moiety. In some embodiments, the amine donor unit-linker (Y-Z) is a branched unit and the agent moiety (Z) comprises at least about 2 agent moieties. In some embodiments, the amine donor unit-linker is a linear unit. In some embodiments, the amine donor agent is selected from the group consisting of Alexa 488 cadaverine, 5-FITC cadaverine, Alexa 647 cadaverine, Alexa 350 cadaverine, 5-TAMRA cadaverine, 5-FAM cadaverine, SR101 cadaverine, 5,6-TAMRA cadaverine, 5-FAM lysine, Ac(acetyl)-LysGly-MMAD (monomethyl auristatin D), Amino-PEG3 (polyethylene glycol)-C2-MMAD, Amino-PEG6 C2-MMAD, Amino-PEG3-C2-amino-nonanoyl-MMAD, Aminocaproyl-Val(valine)-Cit(citrulline)-PABC (p-aminobenzyloxycarbonyl)-MMAD, Ac-Lys-Val-Cit-PABC-MMAD, Aminocaproyl-MMAD, Ac-Lys-β-Ala-MMAD, amino-PEG2-C2-MMAE (monomethyl auristatin E), Aminocaproyl-MMAE, amino-PEG3-C2-MMAE, Aminocaproyl-MMAF (monomethyl auristatin F), Aminocaproyl-Val-Cit-PABC-MMAE, Aminocaproyl-Val-Cit-PABC-MMAF, putrescinyl-geldanamycin, and Ac-Lys-putrescinyl-geldanamycin.

In some embodiments, the amine donor unit-linker is selected from the group consisting of Ac-Lys-Gly, aminocaproic acid, Ac-Lys-β-Ala, amino-PEG2-C2, amino-PEG3-C2, amino-PEG6-C2, Ac-Lys-Val-Cit-PABC, Aminocaproyl-Val-Cit-PABC, putrescine, and Ac-Lys-putrescine.

In some embodiments, the agent moiety is a small molecule. In some embodiments, the small molecule is a cytotoxic agent or an imaging agent. In some embodiments, the cytotoxic agent is selected from the group consisting of an anthracycline, an auristatin, a dolastatin, a duocarmycin, an enediyne, a geldanamycin, a maytansine, a puromycin, a taxane, a vinca alkaloid, SN-38, a tubulysin, a hemiasterlin and stereoisomers, isosteres, analogs, or derivatives thereof. In some embodiments, the agent moiety is a biocompatible polymer or a polypeptide.

In another aspect, the invention provides an engineered Fc-containing polypeptide conjugate comprising the formula: (Fc-containing polypeptide)-T-A, wherein the Fc-containing polypeptide comprises a first Fc-containing polypeptide; wherein T is an acyl donor glutamine-containing tag engineered at a specific site or comprises an endogenous glutamine made reactive by the first Fc-containing polypeptide engineering; wherein A is an amine donor agent; wherein the amine donor agent comprises a second Fc-containing polypeptide and a tag and does not comprise a reactive Gln; and wherein the acyl donor glutamine-containing tag is site-specifically crosslinked to the first Fc-containing polypeptide and the second Fc-containing polypeptide. In some embodiments, the acyl donor glutamine-containing tag is not spatially adjacent to a reactive Lys in the first Fc-containing polypeptide. In some embodiments, the engineered Fc-containing polypeptide conjugate is a bispecific Fc-containing polypeptide (e.g., bispecific antibody).

In another aspect, the invention provides an engineered Fc-containing polypeptide conjugate comprising the formula: (Fc-containing polypeptide)-T-A, wherein the Fc-containing polypeptide comprises a first Fc-containing polypeptide; wherein T is an acyl donor glutamine-containing tag engineered at a specific site; wherein A is an amine donor agent; wherein the amine donor agent comprises a second Fc-containing polypeptide and does not comprise a reactive Gln; and wherein the acyl donor glutamine-containing tag is site-specifically crosslinked to the first Fc-containing polypeptide and the second Fc-containing polypeptide. In some embodiments, the acyl donor glutamine-containing tag is not spatially adjacent to a reactive Lys in the first Fc-containing polypeptide. In some embodiments, the engineered Fc-containing polypeptide conjugate is a bispecific Fc-containing polypeptide (e.g., bispecific antibody).

In some embodiments, the tag comprises a G or GG and wherein the tag is spatially adjacent to a reactive Lys in the second Fc-containing polypeptide.

In some embodiments, the tag is an amine donor tag comprising a Lys. In some embodiments, the amine donor tag comprises an amino acid sequence KG. In some embodiments, the amine donor tag comprises an amino acid sequence selected from the group consisting of KGG, GKGG (SEQ ID NO:11), GSKGG (SEQ ID NO:12), GSGKGG (SEQ ID NO:13), and GSGGKGG (SEQ ID NO:14).

In another aspect, the invention provides an engineered Fc-containing polypeptide conjugate comprising the formula: (Fc-containing polypeptide)-T-A, wherein the Fc-containing polypeptide comprises a first Fc-containing polypeptide and a second Fc-containing polypeptide; wherein T is an acyl donor glutamine-containing tag comprising a first acyl donor glutamine-containing tag and a second acyl donor glutamine-containing tag crosslinked to the first Fc-containing polypeptide and the second Fc-containing polypeptide, respectively; wherein A is an amine donor agent; and wherein the first and the second acyl donor glutamine-containing tags are site-specifically crosslinked to each other. In some embodiments, the engineered Fc-containing polypeptide conjugate is a bispecific Fc-containing polypeptide. In some embodiments, the amine donor agent does not comprise a reactive Gln. In some embodiments, the first acyl donor glutamine-containing tag and the second acyl donor glutamine-containing tag are not spatially adjacent to a reactive Lys in the first Fc-containing polypeptide and the second Fc-containing polypeptide, respectively.

In another aspect, the invention provides an engineered Fc-containing polypeptide conjugate comprising the formula: (Fc-containing polypeptide)-T-A, wherein the Fc-containing polypeptide comprises a first Fc-containing polypeptide and a second Fc-containing polypeptide; wherein T is an acyl donor glutamine-containing tag crosslinked to the first Fc-containing polypeptide; wherein A is an amine donor agent; and wherein the acyl donor glutamine-containing tag is site-specifically crosslinked to the second Fc-containing polypeptide. In some embodiments, the engineered Fc-containing polypeptide conjugate is a bispecific Fc-containing polypeptide. In some embodiments, the amine donor agent does not comprise a reactive Gln. In some embodiments, the acyl donor glutamine-containing tag is not adjacent to a reactive Lys in the first Fc-containing polypeptide.

In some embodiments, the amine donor agent is a compound comprising a diamine. In some embodiments, the compound is selected from the group consisting of putrescine (butane-1,4-diamine), ethylenediamine, cadaverine (pentane-1,5-diamine), spermidine, spermine, hydrazine, 1,3-diaminopropane, hexamethylenediamine, phenylenediamine, xylylenediamine, diphenylethylenediamine, 1,8-diaminonapthalene, and stereoisomers, isosteres, analogs or derivatives thereof.

In another aspect, the invention provides an engineered Fab-containing polypeptide conjugate comprising the formula: (Fab-containing polypeptide)-T-A, wherein T is an acyl donor glutamine-containing tag engineered at a specific site or comprises an endogenous glutamine made reactive by the Fab-containing polypeptide engineering; wherein A is an amine donor agent; wherein the amine donor agent is a biocompatible polymer comprising a reactive amine; and wherein the biocompatible polymer is site-specifically conjugated to the acyl donor glutamine-containing tag or the endogenous glutamine at a carboxyl terminus, an amino terminus, or at an another site in the Fab-containing polypeptide. In some embodiments, the acyl donor glutamine-containing tag comprises one Gln.

In another aspect, the invention provides an engineered toxin polypeptide conjugate comprising the formula: (toxin polypeptide)-T-A, wherein T is an acyl donor glutamine-containing tag engineered at a specific site or comprises an endogenous glutamine made reactive by the toxin polypeptide engineering; wherein A is an amine donor agent; wherein the amine donor agent is a biocompatible polymer comprising a reactive amine; and wherein the biocompatible polymer is site-specifically conjugated to the acyl donor glutamine-containing tag or the endogenous glutamine at a carboxyl terminus, an amino terminus, or at an another site in the toxin polypeptide. In some embodiments, both the acyl donor glutamine-containing tag (or the endogenous glutamine) and the biocompatible polymer are substrates for transglutaminase. In some embodiments, the linkage between the acyl donor glutamine-containing tag (or the endogenous glutamine) and the biocompatible polymer is of the formula $CH_2$—$CH_2$—CO—NH—.

In one variation, the invention provides an engineered toxin polypeptide conjugate comprising the formula: (toxin polypeptide)-T-B, wherein T is an acyl donor glutamine-containing tag engineered at a specific site; wherein B is a biocompatible polymer; and wherein the toxin polypeptide is site-specifically conjugated to the acyl donor glutamine-containing tag at any site in the biocompatible polymer. In some embodiments, the acyl donor glutamine-containing tag in the biocompatible polymer is spatially adjacent to a reactive Lys in the toxin polypeptide. In some embodiments, the toxin polypeptide comprises an amine donor tag comprising a Lys.

In another aspect, the invention provides a method for preparing an engineered Fc-containing polypeptide conjugate comprising the formula: (Fc-containing polypeptide)-T-A, wherein T is an acyl donor glutamine-containing tag engineered at a specific site or comprises an endogenous glutamine made reactive by the Fc-containing polypeptide engineering; wherein A is an amine donor agent; and wherein the amine donor agent is site-specifically conjugated to the acyl donor glutamine-containing tag or the endogenous glutamine at a carboxyl terminus, an amino terminus, or at an another site in the Fc-containing polypeptide, comprising the steps of: a) providing an engineered (Fc-containing polypeptide)-T molecule comprising the Fc-containing polypeptide located at the acyl donor glutamine-containing tag or the endogenous glutamine; b) contacting the amine donor agent with the engineered (Fc-containing polypeptide)-T molecule in the presence of a transglutaminase; and c) allowing the engineered (Fc-containing polypeptide)-T to covalently link to the amine donor agent to form the engineered Fc-containing polypeptide conjugate.

In another aspect, the invention provides a method for preparing an engineered Fc-containing polypeptide conjugate comprising the formula: (Fc-containing polypeptide)-T-A, wherein the Fc-containing polypeptide comprises a first Fc-containing polypeptide; wherein T is an acyl donor glutamine-containing tag engineered at a specific site or comprises an endogenous glutamine made reactive by the Fc-containing polypeptide engineering; wherein A is an amine donor agent; wherein the amine donor agent comprises a second Fc-containing polypeptide and a tag and does not comprise a reactive Gln; and wherein the acyl donor glutamine-containing tag is site-specifically crosslinked to the first Fc-containing polypeptide and the second Fc-containing polypeptide, comprising the steps of: a) providing an engineered (Fc-containing polypeptide)-T molecule comprising the first Fc-containing polypeptide located at the acyl donor glutamine-containing tag or the endogenous glutamine; b) providing an engineered (Fc-containing polypeptide)-tag comprising the second Fc-containing polypeptide located at the tag; c) contacting the engineered (Fc-containing polypeptide)-T molecule with the engineered (Fc-containing polypeptide)-tag molecule in reducing environment; and d) allowing the engineered (Fc-containing polypeptide)-T molecule to site-specifically and covalently link to the engineered (Fc-containing polypeptide)-tag molecule to form the Fc-containing polypeptide conjugate in the presence of a transglutaminase. In some embodiments, the acyl donor glutamine-containing tag comprises an amino acid sequence GSPLAQSHGG (SEQ ID NO:7) and the amine donor tag comprises an amino acid sequence GSGGKGG (SEQ ID NO:14). In some embodiments, the crosslinking efficiency of the engineered (Fc-containing polypeptide)-T molecule to the engineered (Fc-containing polypeptide)-tag molecule is at least about 30%. In some embodiments, the acyl donor tag is not spatially adjacent to a reactive Lys in the first Fc-containing polypeptide.

In another aspect, the invention provides a method for preparing an engineered Fc-containing polypeptide conjugate comprising the formula: (Fc-containing polypeptide)-T-A, wherein the Fc-containing polypeptide comprises a first Fc-containing polypeptide; wherein T is an acyl donor glutamine-containing tag engineered at a specific site; wherein A is an amine donor agent; wherein the amine donor agent comprises a second Fc-containing polypeptide and does not comprise a reactive Gln; and wherein the acyl donor glutamine-containing tag is site-specifically crosslinked to the first Fc-containing polypeptide and the second Fc-containing polypeptide, comprising the steps of: a) providing an engineered (Fc-containing polypeptide)-T molecule comprising the first Fc-containing polypeptide located at the acyl donor glutamine-containing tag; b) providing the second Fc-containing polypeptide; c) contacting the engineered (Fc-containing polypeptide)-T molecule with the second Fc-containing polypeptide in reducing environment; and d) allowing the engineered (Fc-containing polypeptide)-T molecule to site-specifically and covalently link to the second Fc-containing polypeptide to form the Fc-containing polypeptide conjugate in the presence of a transglutaminase. In some embodiments, the acyl donor glutamine-containing tag comprises an amino acid sequence GSPLAQSHGG (SEQ ID NO:7) and the amine donor tag comprises an amino acid sequence GSGGKGG (SEQ ID NO:14). In some embodiments, the crosslinking efficiency of the engineered (Fc-containing polypeptide)-T molecule to the second Fc-containing polypeptide is at least about 30%. In some embodiments, the acyl donor glutamine-containing tag is not spatially adjacent to a reactive Lys in the first Fc-containing polypeptide.

In another aspect, the invention provides a method for preparing an engineered Fc-containing polypeptide conjugate comprising the formula: (Fc-containing polypeptide)-T-A, wherein the Fc-containing polypeptide comprises a first Fc-containing polypeptide and a second Fc-containing polypeptide; wherein T is an acyl donor glutamine-containing tag comprising a first acyl donor glutamine-containing tag and a second acyl donor glutamine-containing tag crosslinked to the first Fc-containing polypeptide and the second Fc-containing polypeptide, respectively; wherein A is an amine donor agent; and wherein the first and the second acyl donor glutamine-containing tags are site-specifically crosslinked to each other, comprising the steps of: a) providing a first engineered (Fc-containing polypeptide)-T molecule comprising the first Fc-containing polypeptide attached to the first acyl donor glutamine-containing tag; b) providing a second engineered (Fc-containing polypeptide)-T molecule comprising the second Fc-containing polypeptide attached to the second acyl donor glutamine-containing tag; c) contacting the first engineered (Fc-containing polypeptide)-T molecule with the second engineered (Fc-containing polypeptide)-T molecule and the amine donor agent in reducing environment; and d) allowing the first engineered (Fc-containing polypeptide)-T molecule to site-specifically and covalently react with the second engineered (Fc-containing polypeptide)-T molecule to form the engineered Fc-containing polypeptide conjugate in the presence of a transglutaminase. In some embodiments, the first acyl donor glutamine-containing tag and the second acyl donor glutamine-containing tag are not spatially adjacent to a reactive Lys in the first Fc-containing polypeptide and the second Fc-containing polypeptide, respectively.

In another aspect, the invention provides a method for preparing an engineered Fc-containing polypeptide conjugate comprising the formula: (Fc-containing polypeptide)-T-A, wherein the Fc-containing polypeptide comprises a first Fc-containing polypeptide and a second Fc-containing polypeptide; wherein T is an acyl donor glutamine-containing tag crosslinked to the first Fc-containing polypeptide; wherein A is an amine donor agent; and wherein the acyl donor glutamine-containing tag is site-specifically crosslinked to the second Fc-containing polypeptide, comprising the steps of: a) providing an engineered (Fc-containing polypeptide)-T molecule comprising the first Fc-containing polypeptide attached to the first acyl donor glutamine-containing tag; b) providing the second Fc-containing polypeptide; c) contacting the engineered (Fc-containing polypeptide)-T molecule with the second Fc-containing polypeptide and the amine donor agent in reducing environment; and d) allowing the engineered (Fc-containing polypeptide)-T molecule to site-specifically and covalently react with the second Fc-containing polypeptide to form the engineered Fc-containing polypeptide conjugate in the presence of a transglutaminase. In some embodiments, the acyl donor glutamine-containing tag is not adjacent to a reactive Lys in the first Fc-containing polypeptide.

In another aspect, the invention provides a method for preparing an engineered Fab-containing polypeptide conjugate comprising the formula: (Fab-containing polypeptide)-T-A, wherein T is an acyl donor glutamine-containing tag engineered at a specific site or comprises an endogenous glutamine made reactive by the Fab-containing polypeptide engineering, wherein A is an amine donor agent; wherein the amine donor agent is a biocompatible polymer comprising a reactive amine; and wherein the biocompatible polymer is site-specifically conjugated to the acyl donor glutamine-containing tag or the endogenous glutamine at a carboxyl terminus, an amino terminus, or at an another site in the Fab-containing polypeptide; comprising the steps of: a) providing an engineered (Fab-containing polypeptide)-T molecule comprising the Fab-containing polypeptide located at the acyl donor glutamine-containing tag; b) contacting the biocompatible polymer with the engineered (Fab-containing polypeptide)-T molecule in the presence of a transglutaminase; and c) allowing the engineered (Fab-containing polypeptide)-T to covalently link to the biocompatible polymer to form the engineered Fab-containing polypeptide conjugate.

In another aspect, the invention provides a method for preparing an engineered toxin polypeptide conjugate comprising the formula: (toxin polypeptide)-T-A, wherein T is an acyl donor glutamine-containing tag engineered at a specific site or an endogenous glutamine made reactive by the toxin polypeptide engineering; wherein A is an amine donor agent; wherein the amine donor agent is a biocompatible polymer comprising a reactive amine; and wherein the biocompatible polymer is site-specifically conjugated to the acyl donor glutamine-containing tag or the endogenous glutamine at a carboxyl terminus, an amino terminus, or at an another site in the toxin polypeptide; comprising the steps of: a) providing an engineered (toxin polypeptide)-T molecule comprising the toxin polypeptide located at the acyl donor glutamine-containing tag or the endogenous glutamine; b) contacting the biocompatible polymer with the engineered (toxin polypeptide)-T molecule in the presence of a transglutaminase; and c) allowing the engineered (toxin polypeptide)-T to covalently link to the biocompatible polymer to form the engineered toxin polypeptide conjugate.

In another aspect, the invention provides a method for preparing an engineered toxin polypeptide conjugate comprising the formula: (toxin polypept embodiments, the effector function of the IgG increases more than about 2-fold relative to a wild type IgG.

In some embodiments, the acyl donor glutamine-containing tag is inserted (attached to) or replaces one or more wild-type amino acid(s) at the carboxyl terminus and/or the amino terminus of the toxin polypeptide. In some embodiments, the acyl donor glutamine-containing tag is inserted or replaces one or more wild-type amino acid(s) at an another site on the toxin polypeptide, wherein the another site is not the amino or the carboxyl terminus.

In some embodiments, the engineered polypeptide conjugate as described herein (e.g., the engineered Fc-containing polypeptide conjugate, Fab-containing polypeptide, or toxin polypeptide conjugate) has conjugation efficiency of at least about 51%. In some embodiments, the engineered Fc-containing polypeptide conjugate as described herein (e.g., bispecific antibody) has conjugation efficiency of at least about 30%. In some embodiments, the engineered Fc-containing polypeptide conjugate has conjugation efficiency of at least about 95% and the concentration ratio between the amine donor agent contacted and the engineered (Fc-containing polypeptide) contacted is about 50:1.

In some embodiments, the engineered polypeptide conjugate as described herein (e.g., the engineered Fc-containing polypeptide conjugate, Fab-containing polypeptide, or toxin polypeptide conjugate) is present in a subject (e.g., a mammal) at at least about 20% after at least about 2 hours in vivo exposure.

In another aspect, the invention provides a composition comprising the engineered polypeptide conjugates described herein (e.g., the engineered Fc-containing polypeptide conjugate, Fab-containing polypeptide, or toxin polypeptide conjugate).

In another aspect, the invention provides a pharmaceutical composition comprising engineered polypeptide conjugates described herein (e.g., the engineered Fc-containing polypeptide conjugate, Fab-containing polypeptide, or toxin polypeptide conjugate) and a pharmaceutically acceptable excipient.

In another aspect, the invention provides an engineered polypeptide conjugate (e.g., the engineered Fc-containing polypeptide conjugate, Fab-containing polypeptide, or toxin polypeptide conjugate) purified by the methods described herein.

BRIEF DESCRIPTION OF THE DRAWINGS

FIG. 8A-1, FIG. 8A-2, FIG. 8B-1, and FIG. 8B-2 show site-specific conjugation of the antibody-(acyl donor glutamine-containing tag) and amine donor agent (cadaverine Alexa-488) in the presence of a transglutaminase as verified by mass spectrometry.

DETAILED DESCRIPTION OF THE INVENTION

Figure 1:
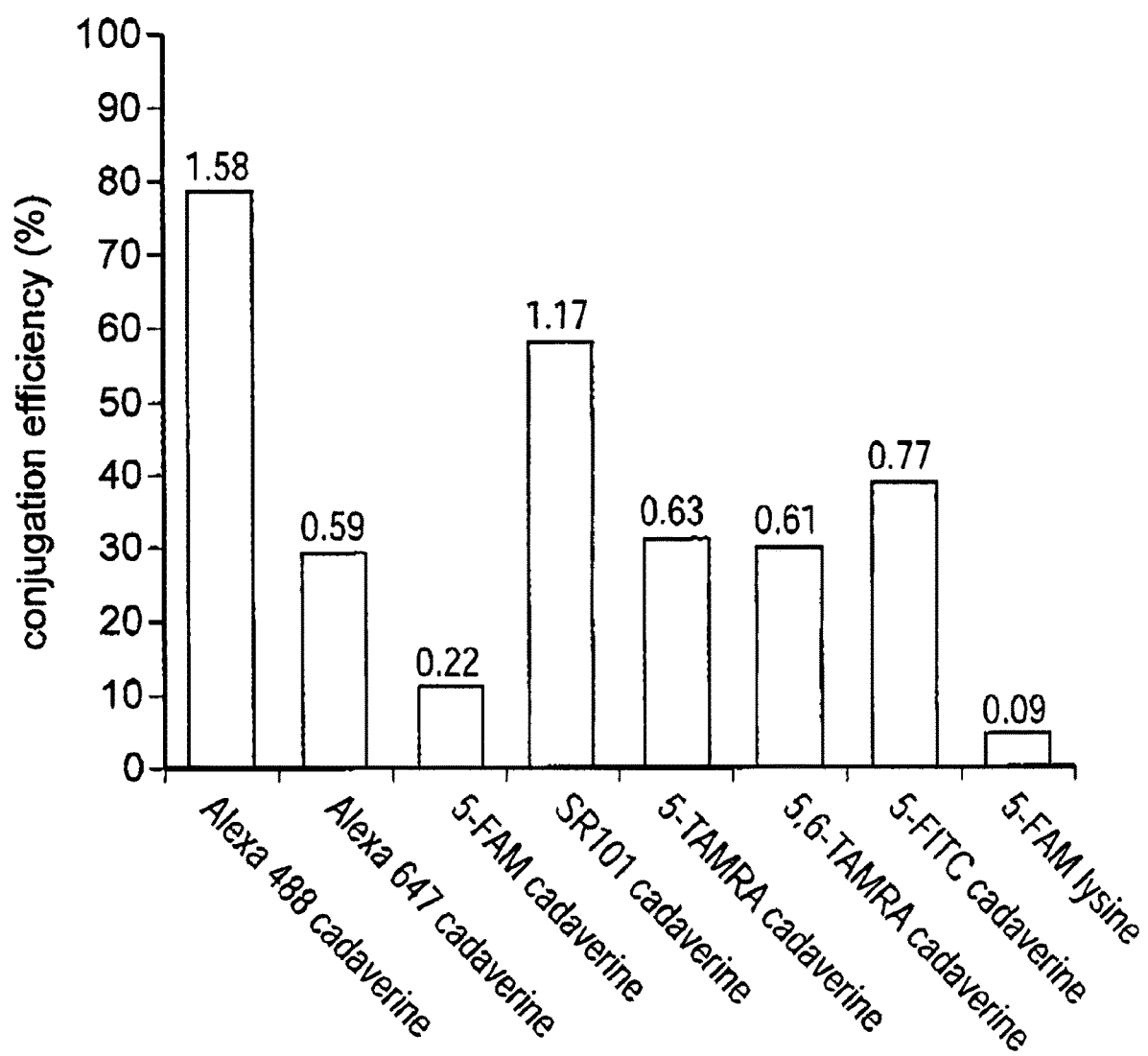
FIG. 1 shows the conjugation efficiencies of transglutaminase-catalyzed conjugation between mAb1-HCQ01 (IgG1 subtype monoclonal antibody) carrying the HCQ01 tag (LLQGG (SEQ ID NO:2)) at the carboxyl terminus of the heavy chain and various amine-containing fluorophore derivatives. The efficiency values for purified conjugates were calculated from the relative UV-vis absorbance at the excitation wavelength of each fluorophore and at 280 nm. The corresponding fluorophore/antibody loading is indicated above each bar.

The present invention provides engineered polypeptide conjugates and methods for making thereof using transglutaminase. The inventors have discovered that an Fc-containing polypeptide engineered with an acyl donor glutamine-containing tag (e.g., Gln containing peptide tags) or an endogenous glutamine made reactive by polypeptide engineering (e.g., via amino acid deletion, insertion, substitution, or mutation of the polypeptide), in the presence of transglutaminase, can covalently crosslink with an amine donor agent (e.g., a small molecule comprising or attached to an amine donor unit) to form a stable and homogenous population of an engineered Fc-containing polypeptide conjugate with the amine donor agent being site-specifically conjugated to the Fc-containing polypeptide through the acyl donor glutamine-containing tag or the endogenous glutamine. The conjugation efficiency of the Fc-containing polypeptide engineered with an acyl donor glutamine-containing tag (or the endogenous glutamine) and the amine donor agent is at least about 51%, and the conjugation efficiency between the Fc-containing polypeptide and the amine donor agent is less than about 5% in the absence of the acyl donor glutamine-containing tag or the accessible/exposed/reactive endogenous glutamine. For example, deletion or mutation of the last amino acid from Lys (lysine) to another amino acid in the Fc-containing polypeptide spatially adjacent to the Gln-containing peptide tag provides a significant increase in conjugation efficiency of the Fc-containing polypeptides and the small molecule (e.g., a cytotoxic agent or an imaging agent). The inventors have also discovered that, in the presence of transglutaminase, a stable and homogenous population of a bispecific antibody can be generated using a Gln-containing peptide tag engineered to a first Fc-containing polypeptide directed to an epitope and another peptide tag (e.g., a Lys containing polypeptide tag) engineered to a second Fc-containing polypeptide directed to a second epitope in reducing environment. A similar bispecific antibody can also be made by combining two different Fc-containing polypeptides engineered to two Gln-containing peptide tags with a diamine. The inventors have further discovered that, in the presence of transglutaminase, a stable and homogenous Fab-containing polypeptide conjugate or a toxin polypeptide conjugate with longer half life can be made by covalently reacting a Gln-containing peptide tag engineered to a Fab-containing polypeptide or a toxin polypeptide with a biocompatible polymer. Further, the selection of the acyl donor glutamine-containing tags, Fc-containing polypeptides, and/or the amine donor agents as described herein allows for site-specific conjugation. Without wishing to be bound by theory, the antibody-drug-conjugates, bispecific antibodies, antibody-biocompatible polymer conjugates, toxin-biocompatible polymer-conjugates generated using the methods described herein are stable, resistant to proteolytic degradation in vivo, in vitro, and ex vivo, and/or have longer half-life.

Accordingly, in one aspect of the invention, provided is an engineered Fc-containing polypeptide conjugate comprising the formula: (Fc-containing polypeptide)-T-A, wherein T is an acyl donor glutamine-containing tag engineered (e.g., via insertion or replacement/substitution of wild-type amino acid(s)) at a specific site or comprises an endogenous glutamine made reactive (i.e., the ability to form a covalent bond as an acyl donor in the presence of an amine and a transglutaminase) by the Fc-containing polypeptide engineering; wherein A is an amine donor agent; and wherein the amine donor agent is site-specifically conjugated to the acyl donor glutamine-containing tag at a carboxyl terminus, an amino terminus, or at an another site in the Fc-containing polypeptide.

In another aspect, provided is an engineered Fc-containing polypeptide conjugate comprising the formula: (Fc-containing polypeptide)-T-A, wherein the Fc-containing polypeptide conjugate comprises a first Fc-containing polypeptide; wherein T is an acyl donor glutamine-containing tag engineered at a specific site or comprises an endogenous glutamine made reactive by the Fc-containing polypeptide engineering; wherein A is an amine donor agent; wherein the amine donor agent comprises a second Fc-containing polypeptide and a tag and does not comprise a reactive Gln; and wherein the acyl donor glutamine-containing tag or the endogenous glutamine is site-specifically crosslinked to the first Fc-containing polypeptide and the second Fc-containing polypeptide.

In another aspect, provided is an engineered Fc-containing polypeptide conjugate comprising the formula: (Fc-containing polypeptide)-T-A, wherein the Fc-containing polypeptide comprises a first Fc-containing polypeptide and a second Fc-containing polypeptide; wherein T is an acyl donor glutamine-containing tag comprising a first acyl donor glutamine-containing tag and a second acyl donor glutamine-containing tag crosslinked to the first Fc-containing polypeptide and the second Fc-containing polypeptide, respectively; wherein A is an amine donor agent; and wherein the first and the second acyl donor glutamine-containing tags are site-specifically crosslinked to each other.

In some embodiments, provided is an engineered Fc-containing polypeptide conjugate comprising the formula: (Fc-containing polypeptide)-A, wherein the Fc-containing polypeptide is aglycosylated at amino acid position 295 (e.g., in human IgG1) and comprises an amino acid modification at amino acid position 297 relative to a wild-type human IgG1 antibody; wherein A is an amine donor agent; and wherein the amine donor agent is site-specifically conjugated to the endogenous glutamine at amino acid position 295 in the Fc-containing polypeptide. In some embodiments, the amino acid modification is not a substitution from asparagin (Asn or N) to glutamine at position 297 of human IgG (Kabat numbering scheme).

In another aspect, provided is an engineered Fab-containing polypeptide conjugate comprising the formula: (Fab-containing polypeptide)-T-A, wherein T is an acyl donor glutamine-containing tag engineered at a specific site or comprises an endogenous glutamine made reactive by the Fab-containing polypeptide engineering; wherein A is an amine donor agent; wherein the amine donor agent is a biocompatible polymer comprising a reactive amine; and wherein the biocompatible polymer is site-specifically conjugated to the acyl donor glutamine-containing tag or the endogenous glutamine at a carboxyl terminus, an amino terminus, or at an another site in the Fab-containing polypeptide.

In another aspect, the invention provides an engineered toxin polypeptide conjugate comprising the formula: (toxin polypeptide)-T-A, wherein T is an acyl donor glutamine-containing tag engineered at a specific site or comprises an endogenous glutamine made reactive by the toxin polypeptide engineering; wherein A is an amine donor agent, wherein the amine donor agent is a biocompatible polymer comprising a reactive amine, and wherein the biocompatible polymer is site-specifically conjugated to the acyl donor glutamine-containing tag or the endogenous glutamine at a carboxyl terminus, an amino terminus, or at an another site in the toxin polypeptide.

In another aspect, the invention provides an engineered toxin polypeptide conjugate comprising the formula: (toxin polypeptide)-T-B, wherein T is an acyl donor glutamine-containing tag at a specific site; wherein B is a biocompatible polymer; and wherein the toxin polypeptide is site-specifically conjugated to the acyl donor glutamine-containing tag at any site in the biocompatible polymer.

In another aspect, provided is a method for preparing an engineered Fc-containing polypeptide conjugate comprising the formula: (Fc-containing polypeptide)-T-A, wherein T is an acyl donor glutamine-containing tag engineered at a specific site or comprises an endogenous glutamine made reactive by the Fc-containing polypeptide engineering; wherein A is an amine donor agent; and wherein the amine donor agent is site-specifically conjugated to the acyl donor glutamine-containing tag or the endogenous glutamine at a carboxyl terminus, an amino terminus, or at an another site in the Fc-containing polypeptide, comprising the steps of: a) providing an engineered (Fc-containing polypeptide)-T molecule comprising the Fc-containing polypeptide located at the acyl donor glutamine-containing tag or the endogenous glutamine; b) contacting the amine donor agent with the engineered (Fc-containing polypeptide)-T molecule in the presence of a transglutaminase; and c) allowing the engineered (Fc-containing polypeptide)-T to covalently link to the amine donor agent to form the engineered Fc-containing polypeptide conjugate.

In another aspect, the invention provides a method for preparing an engineered Fc-containing polypeptide conjugate comprising the formula: (Fc-containing polypeptide)-T-A, wherein the Fc-containing polypeptide comprises a first Fc-containing polypeptide; wherein T is an acyl donor glutamine-containing tag engineered at a specific site or comprises an endogenous glutamine made reactive by the Fab-containing polypeptide engineering; wherein A is an amine donor agent; wherein the amine donor agent comprises a second Fc-containing polypeptide and a tag and does not comprise a reactive Gln; and wherein the acyl donor glutamine-containing tag or the endogenous glutamine is site-specifically crosslinked to the first Fc-containing polypeptide and the second Fc-containing polypeptide, comprising the steps of: a) providing an engineered (Fc-containing polypeptide)-T molecule comprising the first Fc-containing polypeptide located at the acyl donor glutamine-containing tag or the endogenous glutamine; b) providing an engineered (Fc-containing polypeptide)-tag comprising the second Fc-containing polypeptide located at the tag; c) contacting the engineered (Fc-containing polypeptide)-T molecule with the engineered (Fc-containing polypeptide)-tag molecule in reducing environment; and d) allowing the engineered (Fc-containing polypeptide)-T molecule to site-specifically and covalently link to the engineered (Fc-containing polypeptide)-tag molecule to form the Fc-containing polypeptide conjugate in the presence of a transglutaminase.

In another aspect, the invention provides a method for preparing an engineered Fc-containing polypeptide conjugate comprising the formula: (Fc-containing polypeptide)-T-A, wherein the Fc-containing polypeptide comprises a first Fc-containing polypeptide and a second Fc-containing polypeptide; wherein T is an acyl donor glutamine-containing tag comprising a first acyl donor glutamine-containing tag and a second acyl donor glutamine-containing tag crosslinked to the first Fc-containing polypeptide and the second Fc-containing polypeptide, respectively; wherein the first acyl donor glutamine-containing tag and the second acyl donor glutamine-containing tag are not spatially adjacent to a reactive Lys in the first Fc-containing polypeptide and the second Fc-containing polypeptide, respectively; wherein A is an amine donor agent; and wherein the first and the second acyl donor glutamine-containing tags are site-specifically crosslinked to each other, comprising the steps of: a) providing a first engineered (Fc-containing polypeptide)-T molecule comprising the first Fc-containing polypeptide located at the first acyl donor glutamine-containing tag; b) providing a second engineered (Fc-containing polypeptide)-T molecule comprising the second Fc-containing polypeptide located at the second acyl donor glutamine-containing tag; c) contacting the first engineered (Fc-containing polypeptide)-T molecule with the second engineered (Fc-containing polypeptide)-T molecule and the amine donor agent in reducing environment; and d) allowing the first engineered (Fc-containing polypeptide)-T molecule to site-specifically and covalently link to the second engineered (Fc-containing polypeptide)-T molecule to form the engineered Fc-containing polypeptide conjugate in the presence of a transglutaminase.

General Techniques and Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present invention are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium* of *Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, molecular biology, biochemistry, immunology, analytical chemistry, synthetic organic chemistry, and medicinal and pharmaceutical chemistry described herein are those well known and commonly used in the art. Throughout this specification and claims, the word "comprise," or variations such as "comprises" or "comprising," will be understood to imply the inclusion of a stated integer or group of integers but not the exclusion of any other integer or group of integers.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

The term "Fc-containing polypeptide" as used herein refers to a polypeptide (e.g., an antibody or an immunoadhesin) comprising the carboxyl terminal polypeptide sequences of an immunoglobulin heavy chain. The Fc-containing polypeptide may comprise native or variant Fc regions (i.e., sequences). The Fc region of an immunoglobulin generally comprises two constant domains, a CH2 domain and a CH3 domain, and optionally comprises a CH4 domain. An Fc-containing polypeptide may comprise part or all of a wild-type hinge sequence (generally at its amino terminus). An Fc-containing polypeptide may also be a dimer. An Fc-containing polypeptide may be obtained or derived from any suitable immunoglobulin, such as from at least one of the various IgG1, IgG2, IgG3, or IgG4 subtypes, or from IgA, IgE, IgD or IgM. Although the boundaries of the Fc region of an immunoglobulin heavy chain might vary, for example, the human IgG heavy chain Fc region is usually defined to stretch from an amino acid residue at position Glu216, or from Ala231, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991.

An Fc-containing polypeptide may be an Fc-containing fusion polypeptide, wherein one or more polypeptides is operably linked to an Fc-containing polypeptide. An Fc fusion combines the Fc polypeptide of an immunoglobulin with a fusion partner, which in general may be any protein, polypeptide, or small molecule. Virtually any protein or small molecule may be linked to the Fc region to generate an Fc-containing fusion polypeptide. Fc-containing fusion partners may include, but are not limited, the target-binding region of a receptor, an adhesion molecule, a ligand, an enzyme, a cytokine, a chemokine, or some other protein or protein domain.

The term "acyl donor glutamine-containing tag", "glutamine tag," "Q-containing tag", or "Q-tag" as used herein refers to a polypeptide or a protein containing one or more Gln residue(s) that acts as a transglutaminase amine acceptor.

The term "amine donor agent" or "acyl acceptor" as used herein refers to an agent containing one or more reactive amines (e.g., primary amines). For example, the amine donor agent can comprise an amine donor unit (e.g., primary amine $NH_2$), a linker, and an agent moiety (e.g., a small molecule). The amine donor agent can also be a polypeptide (e.g., an antibody) or a biocompatible polymer containing a reactive Lys (e.g., an endogenous Lys).

As used herein, the term "biocompatible polymer" refers to a polymer (e.g., repeating monomeric or structural units) that is suitable for therapeutic or medical treatment in a recipient (e.g., human) without eliciting any undesirable local or systemic effects in the recipient. A biocompatible polymer (synthetic, recombinant, or native) can be a water soluble or water insoluble polymer. A biocompatible polymer can also be a linear or a branched polymer.

As used herein, the term "site specificity," "site-specifically conjugated," or "site-specifically crosslinked" refers to the specific conjugation or crosslinking of the amine donor agent to the polypeptide engineered with an acyl donor glutamine-containing tag at a specific site (e.g., carboxyl terminus or amino terminus of the antibody or toxin polypeptide, accessible site in the antibody (e.g., antibody light chain and/or heavy chain loops) or toxin polypeptide (e.g., polypeptide loops)). The polypeptide engineered with an acyl donor glutamine-containing tag can be a Fc-containing polypeptide, Fab-containing polypeptide, or a toxin polypeptide. The term "site specificity," "site-specifically conjugated," or "site-specifically crosslinked" can also refer to the specific conjugation or crosslinking of the polypeptide (e.g., toxin polypeptide) to the biocompatible polymer engineered with an acyl donor glutamine-containing tag at a specific site (e.g., an accessible site in the biocompatible polymer). Site specificity can be measured by various techniques, including, but not limited to, mass spectrometry (e.g., matrix-assisted laser-desorption ionization mass spectrometry (MALDI-MS), electrospray ionization mass spectrometry (ESI-MS), tandem mass spectrometry (MS), and time-of-flight mass spectrometry (TOF-MS)), hydrophobic interaction chromatography, ion exchange chromatography, site-directed mutagenesis, fluorescence-labeling, size exclusion chromatography, and X-ray crystallography.

As used herein, the term "spatially adjacent to" refers to interference with the desired transglutaminase reaction.

As used herein, the term "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, unless otherwise indicated by context, the term is intended to encompass not only intact polyclonal or monoclonal antibodies, but also fragments thereof (such as Fab, Fab', F(ab')$_2$, Fv), single chain (ScFv) and domain antibodies, including shark and camelid antibodies), and fusion proteins comprising an antibody portion, multivalent antibodies, multispecific antibodies (e.g., bispecific antibodies so long as they exhibit the desired biological activity) and antibody fragments as described herein, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. On one aspect, the immunoglobulin is a human, murine, or rabbit immunoglobulin.

The term "Fab containing polypeptide" as used herein refers to a polypeptide comprising an Fab fragment, Fab' fragment, or "(Fab')2 fragment. An Fab-containing polypeptide may comprise part or all of a wild-type hinge sequence (generally at its carboxyl terminus). An Fab-containing polypeptide may be obtained or derived from any suitable immunoglobulin, such as from at least one of the various IgG1, IgG2, IgG3, or IgG4 subtypes, or from IgA, IgE, IgD or IgM. An Fab-containing polypeptide may be an Fab-containing fusion polypeptide, wherein one or more polypeptides is operably linked to an Fab-containing polypeptide. An Fab fusion combines the Fab polypeptide of an immunoglobulin with a fusion partner, which in general may be any protein, polypeptide, or small molecule. Virtually any protein or small molecule may be linked to the Fab polypeptide to generate an Fab-containing fusion polypeptide. Fab-containing fusion partners may include, but are not limited, the target-binding region of a receptor, an adhesion molecule, a ligand, an enzyme, a cytokine, a chemokine, or some other protein or protein domain.

A "Fab fragment" is comprised of one light chain and the CH1 and variable regions of one heavy chain. The heavy chain of a Fab molecule cannot form a disulfide bond with another heavy chain molecule.

A "Fab' fragment" contains one light chain and a portion of one heavy chain that contains the VH domain and the CH1 domain and also the region between the CH1 and CH2 domains, such that an interchain disulfide bond can be formed between the two heavy chains of two Fab' fragments to form a F(ab')2 molecule.

A "F(ab')2 fragment" contains two light chains and two heavy chains containing a portion of the constant region between the CH1 and CH2 domains, such that an interchain disulfide bond is formed between the two heavy chains. A F(ab')2 fragment thus is composed of two Fab' fragments that are held together by a disulfide bond between the two heavy chains.

"Antibody fragments" as used herein comprise only a portion of an intact antibody, wherein the portion preferably retains at least one, preferably most or all, of the functions normally associated with that portion when present in an intact antibody.

A "multispecific antibody" is one that targets more than one antigen or epitope. A "bispecific," "dual-specific" or "bifunctional" antibody is a hybrid antibody having two different antigen binding sites. Bispecific antibodies are a species of multispecific antibody and may be produced by a variety of methods including, but not limited to, fusion of hybridomas or linking of Fab' fragments. See, e.g., Songsivilai & Lachmann (1990), *Clin. Exp. Immunol.* 79:315-321; and Kostelny et al. (1992), *J. Immunol.* 148:1547-1553.

The two binding sites of a bispecific antibody will bind to two different epitopes, which may reside on the same or different protein targets.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Further, in contrast to polyclonal antibody preparations that typically include different antibodies directed against different determinants (epitopes), each monoclonal antibody is directed against a single determinant on the antigen.

The monoclonal antibodies herein may, in certain embodiments, specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Humanized antibodies may, moreover, comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

As used herein, the term "immunoadhesin" designates antibody-like or immunoglobulin-like molecules which combine the "binding domain" of a heterologous protein (an "adhesin", e.g. a receptor, ligand or enzyme) with the effector component of immunoglobulin constant domains (i.e., Fc domain). Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin may be obtained from any immunoglobulin, such as IgG1, IgG2, IgG3, or IgG4 subtypes, IgA, IgE, IgD or IgM.

The "hinge region," "hinge sequence," and variation thereof, as used herein, includes the meaning known in the art, which is illustrated, for example, Janeway et al., ImmunoBiology: the immune system in health and disease, (Elsevier Science Ltd., NY) ($4^{th}$ ed., 1999); Bloom et al., Protein Science (1997), 6:407-415; Humphreys et al., J. Immunol. Methods (1997), 209:193-202.

As used herein, the term "wild-type amino acid," "wild-type IgG," "wild-type bispecific antibody," or "wild-type mAb" refers to a sequence of amino acids or nucleic acids that occurs naturally within a certain population (e.g., human, mice, rats, cells, etc.).

As used herein, the term "conjugation efficiency" or "crosslinking efficiency" is the ratio between the experimentally measured amount of engineered polypeptide conjugate divided by the maximum expected engineered polypeptide conjugate amount. Conjugation efficiency or crosslinking efficiency can be measured by various techniques well known to persons skilled in the art, such as hydrophobic interaction chromatography. Conjugation efficiency can also be measured at different temperature, such as room temperature or 37° C.

The term "effector function" refers to the biological activities attributable to the Fc region of an antibody. Examples of antibody effector functions include, but are not limited to, antibody-dependent cell-mediated cytotoxicity (ADCC), Fc receptor binding, complement dependent cytotoxicity (CDC), phagocytosis, C1q binding, and down regulation of cell surface receptors (e.g., B cell receptor; BCR). See, e.g., U.S. Pat. No. 6,737,056. Such effector functions generally require the Fc region to be combined with a binding domain (e.g., an antibody variable domain) and can be assessed using various assays known in the art for evaluating such antibody effector functions. An exemplary measurement of effector function is through Fcγ3 and/or C1q binding.

As used herein "antibody-dependent cell-mediated cytotoxicity" or "ADCC" refers to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, PNAS (USA), 95:652-656.

"Complement dependent cytotoxicity" or "CDC" refers to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202: 163 (1996), may be performed.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, FcγRIII, and FcγRIV subclasses, including allelic variants and alternatively spliced forms of these receptors. FcγRll receptors include FcγRIIA (an "activating receptor") and FcγRI!B (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; de Haas et al., 1995, J. Lab. Clin. Med., 126:330-41; Nimmerjahn et al., 2005, Immunity 23:2-4. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

The term "reducing environment" as used herein refers to a reducing condition that can be achieved by a wide variety of reducing agents, such as glutathione (GSH), TCEP (tris (2-carboxyethyl)phosphine), DTT (Dithiothreitol), BME (2-Mercaptoethanol), and cysteine. Reducing agents are typically used in the micro-millimolar range.

The term "purify," and grammatical variations thereof, is used to mean the removal, whether completely or partially, of at least one impurity from a mixture containing the polypeptide and one or more impurities, which thereby improves the level of purity of the polypeptide in the composition (i.e., by decreasing the amount (ppm) of impurity(ies) in the composition).

Reference to "about" a value or parameter herein includes (and describes) embodiments that are directed to that value or parameter per se. For example, description referring to "about X" includes description of "X." Numeric ranges are inclusive of the numbers defining the range.

An "individual" or a "subject" is a mammal, more preferably, a human. Mammals also include, but are not limited to, farm animals, sport animals, pets, primates, horses, dogs, cats, mice, and rats.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. Exemplary methods and materials are described herein, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. The materials, methods, and examples are illustrative only and not intended to be limiting.

Engineered Polypeptide Conjugate

The engineered polypeptide conjugates herein comprise a polypeptide (e.g., a Fc-containing polypeptide, a Fab-containing polypeptide, or a toxin polypeptide) engineered to an acyl donor glutamine-containing tag or an endogenous glutamine made reactive by polypeptide engineering, wherein the polypeptide is site-specifically conjugated to an amine donor agent (e.g., a small molecule or a biocompatible polymer) via the acyl donor glutamine-containing tag or the accessible/exposed/reactive endogenous glutamine. The acyl donor glutamine-containing tag can be inserted or replace/substituted one or more wild-type amino acids on the polypeptide. The endogenous glutamine can be made reactive (i.e., the ability to form a covalent bond as an acyl donor in the presence of an amine and a transglutaminase) by modifying one or more amino acid(s) (e.g., amino acid deletion, insertion, substitution, or mutation) on the Fc-containing polypeptide, Fab-containing polypeptide, or toxin polypeptide. The engineered polypeptide conjugates can also comprise a polypeptide (e.g., a toxin polypeptide) site-specifically conjugated to a biocompatible polymer engineered to contain an acyl donor glutamine-containing tag.

In one aspect, the engineered polypeptide conjugate is an engineered Fc-containing polypeptide conjugate comprising the formula: (Fc-containing polypeptide)-T-A, wherein T is an acyl donor glutamine-containing tag engineered at a specific site (e.g., via acyl donor glutamine-containing tag insertion or replacement/substitution of one or more wild-type amino acid(s)) or comprises an endogenous glutamine made reactive by the Fc-containing polypeptide engineering, wherein A is an amine donor agent, wherein the amine donor agent is site-specifically conjugated to the acyl donor glutamine-containing tag or the endogenous glutamine at a carboxyl terminus, an amino terminus, or elsewhere at an another site in the Fc-containing polypeptide. Accordingly, both the acyl donor glutamine-containing tag (or the accessible/exposed/reactive glutamine) and the amine donor agent are substrates for transglutaminase, and the linkage between the acyl donor glutamine-containing tag (or the accessible/exposed/reactive glutamine) and the amine donor agent is of the formula $CH_2-CH_2-CO-NH-$.

The transglutaminase used in the invention described herein can be obtained or made from a variety of sources. In some embodiments, the transglutaminase is a calcium dependent transglutaminase which requires calcium to induce enzyme conformational changes and allow enzyme activity. For example, transglutaminase can be derived from guinea pig liver and obtained through commercial sources (e.g., Sigma-Aldrich (St Louis, Mo.) and MP Biomedicals (Irvine, Calif.)). In some embodiments, the transglutaminase is a calcium independent transglutaminase which does not require calcium to induce enzyme conformational changes and allow enzyme activity. In some embodiments, the transglutaminase is a microbial transglutaminase derived from a microbial genome, such as transglutaminase from *Streptoverticillium* or *Streptomices* (e.g., *Streptomyces mobarensis* or *Streptoverticillium mobarensis*). Commercially available calcium independent transglutaminase such as ACTIVA™ (Ajinomoto, Japan) is suitable for the present invention. In some embodiments, the transglutaminase is a mammalian protein (e.g., human transglutaminase), a bacterial protein, a plant protein, a fungi protein (e.g., *Oomycetes* and *Actinomicetes* transglutaminases), or a prokaryotic protein. In some embodiments, the transglutaminase is from *Micrococcus, Clostridium, Turolpsis, Rhizopus, Monascus*, or *Bacillus*.

In some embodiments, the transglutaminase used in the invention described herein can also be a recombinant protein produced using recombinant techniques known to persons skilled in the art. In some embodiments, the transglutaminase used in the invention described herein can be a purified protein. For example, the purified transglutaminase is least about 50% pure. As used herein, "pure" or "purified" protein refers to a protein (e.g., transglutaminase) free from other protein contaminants. In some embodiments, the purified transglutaminase is at least about any of 55%-60%, 60%-65%, 65%-70%, 70%-75%, 75%-80%, 80%-85%, 85%-90%, 90%-95%, 95%-98%, or 99% pure. In some embodiments, the purified transglutaminase is about any of 50%, 55%, 60%, 65%, 70%, 75%, 80%, 85%, 90%, 95%, 96%, 97%, 98%, 99%, or 100% pure.

In some embodiments, the acyl donor glutamine-containing tag of the engineered Fc-containing polypeptide conjugate as described herein is not spatially adjacent to a reactive Lys in the Fc-containing polypeptide. For example, the acyl donor glutamine-containing tag is not spatially adjacent to a reactive Lys in the carboxyl terminus, the amino terminus, or both the carboxyl and the amino termini of the Fc-containing polypeptide.

In some embodiments, the acyl donor glutamine-containing tag comprises at least one Gln. In some embodiments, the acyl donor glutamine-containing tag comprises one Gln. In some embodiments, the acyl donor glutamine-containing tag comprises an amino acid sequence XXQX (SEQ ID NO:1), wherein X can be a conventional or nonconventional amino acid, as described herein. In some embodiments, X is L (Leu), A (Ala), G (Gly), S (Ser), V (Val), F (Phe), Y (Tyr), H (His), R (Arg), N (Asn), E (Glu), D (Asp), C (Cys), Q (Gln), I (Ile), M (Met), P (Pro), T (Thr), K (Lys), or W (Trp). In some embodiments, the acyl donor glutamine-containing tag comprises an amino acid sequence selected from the group consisting of LLQGG (SEQ ID NO:2), LLQG (SEQ ID NO:3), LSLSQG (SEQ ID NO:4), GGGLLQGG (SEQ ID NO:5), GLLQG (SEQ ID NO:6), LLQ, GSPLAQSHGG (SEQ ID NO:7), GLLQGGG (SEQ ID NO:8), GLLQGG (SEQ ID NO:9), GLLQ (SEQ ID NO:10), LLQLLQGA (SEQ ID NO:47), LLQGA (SEQ ID NO:48), LLQYQGA (SEQ ID NO:49), LLQGSG (SEQ ID NO:50), LLQYQG (SEQ ID NO:51), LLQLLQG (SEQ ID NO:52), SLLQG (SEQ ID NO:53), LLQLQ (SEQ ID NO:54), LLQLLQ (SEQ ID NO:55), and LLQGR (SEQ ID NO:56).

In some embodiments, the acyl donor glutamine-containing tag comprises an amino acid sequence selected from the group consisting of QVQLKE (SEQ ID NO:39) and VQLKE (SEQ ID NO:40). In some embodiments, the acyl donor glutamine-containing tag comprises an amino acid sequence selected from the group consisting of LLQGG (SEQ ID NO:2), LLQG (SEQ ID NO:3), LSLSQG (SEQ ID NO:4), GGGLLQGG (SEQ ID NO:5), GLLQG (SEQ ID NO:6), LLQ, GSPLAQSHGG (SEQ ID NO:7), GLLQGGG (SEQ ID NO:8), GLLQGG (SEQ ID NO:9), GLLQ (SEQ ID NO:10), QVQLKE (SEQ ID NO:39), VQLKE (SEQ ID NO:40), LLQLLQGA (SEQ ID NO:47), LLQGA (SEQ ID NO:48), LLQYQGA (SEQ ID NO:49), LLQGSG (SEQ ID NO:50), LLQYQG (SEQ ID NO:51), LLQLLQG (SEQ ID NO:52), SLLQG (SEQ ID NO:53), LLQLQ (SEQ ID NO:54), LLQLLQ (SEQ ID NO:55), and LLQGR (SEQ ID NO:56). In some embodiments, the acyl donor glutamine-containing tag does not comprise an amino acid sequence selected from the group consisting of LGGQGGG (SEQ ID NO:41), GGGQGGL (SEQ ID NO:42), GXGQGGG (SEQ ID NO:43), GGXQGGG (SEQ ID NO:44), GGGQXGG (SEQ ID NO:45), and GGGQGXG (SEQ ID NO:46), wherein X is G, A, S, L, V, F, Y, R, N, or E).

In some embodiments, the Fc-containing polypeptide of the engineered Fc-containing polypeptide conjugate comprises an amino acid modification at the last amino acid position in the carboxyl terminus relative to a wild-type Fc-containing polypeptide at the same position. In some embodiments, the modification is an amino acid deletion, insertion, substitution, mutation, or any combination thereof. In some embodiments, the substitution comprises replacing a wild type amino acid with another (e.g., a non-wild type amino acid). In some embodiment, the insertion comprises inserting one or more amino acid(s) (e.g., inserting one, two, three or more amino acids). In some embodiments, the another (e.g., non-wild type) or inserted amino acid is Arg. In some embodiments, the another (e.g., non-wild type) amino acid is Ala, Asn, Asp, Cys, Glu, Gln, Gly, His, Ile, Leu, Met, Phe, Pro, Ser, Thr, Trp, Tyr, or Val. For example, the last amino acid in the carboxyl terminus of the Fc-containing polypeptide is substituted with Arg, and the acyl donor glutamine-containing tag engineered to the Fc-containing polypeptide comprises an amino acid sequence of LLQGG (SEQ ID NO:2), LLQG (SEQ ID NO:3), or LLQ. The last amino acid in the carboxyl terminus of the Fc-containing polypeptide can also be deleted, and the acyl donor glutamine-containing tag engineered to the Fc-containing polypeptide comprises an amino acid sequence of LLQGG (SEQ ID NO:2), LLQG (SEQ ID NO:3), or LLQ.

In some embodiments, the Fc-containing polypeptide comprises an amino acid modification at the first amino acid position in the amino terminus relative to a wild-type Fc-containing polypeptide at the same position. In some embodiments, the modification is an amino acid deletion, insertion, substitution, mutation, or any combination thereof. In some embodiments, the substitution comprises replacing a wild type amino acid with another (e.g., non-wild type) amino acid. In some embodiment, the insertion comprises inserting an amino acid. In some embodiments, the another (e.g., non-wild type or inserted) amino acid is Arg. In some embodiments, the another (non-wild type or inserted) amino acid is Ala, Asn, Asp, Cys, Glu, Gln, Gly, His, Ile, Leu, Met, Phe, Pro, Ser, Thr, Trp, Tyr, or Val. For example, the first amino acid in the amino terminus of the Fc-containing polypeptide is Gln, and the acyl donor glutamine-containing tag engineered to the Fc-containing polypeptide comprises an amino acid sequence LLQGG (SEQ ID NO:2), LLQG (SEQ ID NO:3), or LLQ.

In some embodiments, the Fc-containing polypeptide conjugate comprises a full length antibody heavy chain and an antibody light chain. In some embodiments, the acyl donor glutamine-containing tag is linked to/located at the Fc-containing polypeptide at the carboxyl terminus of a heavy chain, a light chain, or both the heavy chain and the light chain. In some embodiments, the acyl donor glutamine-containing tag comprises a first acyl donor glutamine-containing tag (e.g., Q-tags listed in Tables 7-9) and a second acyl donor glutamine-containing tag (e.g., Q-tags listed in Tables 7-9), wherein the first acyl donor glutamine-containing tag is located at the carboxyl terminus of the heavy chain, and a second acyl donor glutamine-containing tag is located at the carboxyl terminus of the light chain. In some embodiments, the first acyl donor glutamine-containing tag comprises an amino acid sequence LLQGG (SEQ ID NO:2) or LLQGA (SEQ ID NO:48) and the second acyl donor glutamine-containing tag comprises an amino acid sequence LLQGG (SEQ ID NO:2) or LLQGA (SEQ ID NO:48). In some embodiments, the acyl donor glutamine-containing tag is located at the Fc-containing polypeptide at the amino terminus of a heavy chain, a light chain, or both the heavy chain and the light chain. In some embodiments, the acyl donor glutamine-containing tag comprises a first acyl donor glutamine-containing tag and a second acyl donor glutamine-containing tag, wherein the first acyl donor glutamine-containing tag is located at the amino terminus of a heavy chain, and a second acyl donor glutamine-containing tag is located at the amino terminus of a light chain.

In some embodiments, the Fc-containing polypeptide comprises an antibody. In some embodiments, the antibody is a monoclonal antibody, a polyclonal antibody, a human antibody, a humanized antibody, a chimeric antibody, a bispecific antibody, a minibody, or an antibody fragment.

In some embodiments, the antibody is an IgG. In some embodiments, the IgG is selected from the group consisting of IgG1, IgG2, IgG3, and IgG4.

In some embodiments, the antibody is an IgA, IgE, IgD, or IgM.

In some embodiments, the acyl donor glutamine-containing tag is located at the Fc-containing polypeptide by insertion or by replacement of one or more wild-type amino acid(s) at an another site on the Fc-containing polypeptide, wherein the another site is not an amino or a carboxyl terminus. For example, the acyl donor glutamine-containing tag is part of an antibody loop. The acyl donor glutamine-containing tag can be linked to one or more heavy chain loop(s). The acyl donor glutamine-containing tag can also be linked to one or more light chain loop(s) of the antibody. In some embodiments, the acyl donor glutamine-containing tag is located at both a heavy chain and a light chain loops. In some embodiments, the another site comprises various positions as listed Tables 7, 8, and 9. In some embodiments, the another site is amino acid position(s) 108, 135, 160, 168, 189-192, 190-192, 200-202, 222-223, 251-254, 252-253, 222-223, 293-297, 294-297, 295, 297, or 385 (Kabat numbering scheme) of the human IgG1 antibody.

In some embodiment, Fc-containing polypeptide is engineered to make the endogenous glutamine reactive for amine donor agent. In some embodiments, the Fc-containing polypeptide engineering is an amino acid deletion, insertion, substitution, mutation or any combination thereof on the Fc-containing polypeptide. For example, the wild-type amino acid Asn at position 297 is substituted or replaced with amino acid A, resulting in aglycosylation at position 297 and reactive endogenous glutamine at position 295. In some embodiments, the Fc-containing polypeptide engineering is not an amino acid substitution from asparagines (Asn) to glutamine at position 297 of human IgG (Kabat numbering scheme).

In some embodiments, the effector function (e.g., as measured by Fcγ3 and/or C1q binding) of the engineered Fc-containing polypeptide conjugate decreases no greater than about any of 1-fold, 2-fold, 3-fold, 4-fold, or 5-fold relative to a wild type Fc-containing polypeptide. In some embodiments, the engineered Fc-containing polypeptide conjugate is an IgG, wherein the effector function of the IgG decreases no greater than about 2-fold relative to a wild type IgG. In other embodiments, the effector function of the IgG decreases about 2-fold relative to a wild type IgG. In other embodiments, the effector function of the IgG decreases more than about 2-fold relative to a wild type IgG. In some embodiments, the engineered Fc-containing polypeptide conjugate is an IgG, wherein the effector function of the IgG decreases no greater than about 1-fold relative to a wild type IgG. In other embodiments, the effector function of the IgG decreases about 1-fold relative to a wild type IgG. In some embodiments, the effector function of the IgG decreases more than about any of 1-fold, 3-fold, 4-fold, or 5-fold relative to a wild type IgG.

In some embodiments, the effector function (e.g., as measured by Fcγ3 and/or C1q binding) of the engineered Fc-containing polypeptide conjugate increases at least about 1-fold to 3000-fold relative to a wild type Fc-containing polypeptide. In some embodiments, the effector function of the engineered Fc-containing polypeptide conjugate increases at least about any of 1- to 5-fold, 6- to 10-fold, 11- to 15-fold, 16- to 20-fold, 21- to 25-fold, 26- to 30-fold, 31- to 35-fold, 36- to 40-fold, 41- to 45-fold, 46- to 50-fold, 51- to 55-fold, 56- to 60-fold, 61- to 65-fold, 66- to 70-fold, 71- to 75-fold, 76- to 80-fold, 81- to 85-fold, 86- to 90-fold, 91- to 95-fold, 96- to 100-fold, 101- to 200-fold, 201- to 300-fold, 301- to 500-fold, 501- to 1000-fold, 1001- to 1500-fold, 1501- to 2000-fold, 2001- to 2500-fold, 2501- to 3000-fold relative to a wild type Fc containing polypeptide. In some embodiments, the engineered Fc-containing polypeptide conjugate is an IgG, wherein the effector function of the IgG increases about 1-fold to 300-fold relative to a wild type IgG. In some embodiments, the effector function of the IgG increases about any of 2-fold, 3-fold, 4-fold, 5-fold, 10-fold, 15-fold, 20-fold, 40-fold, 60-fold, 80-fold, 100-fold, 150-fold, 200-fold, 250-fold, 300-fold, 400-fold, 500-fold, 600-fold, 700-fold, 800-fold, 900-fold, 1000-fold, 1500-fold, 2000-fold, 2500-fold, or 3000-fold relative to a wild type IgG.

In some embodiments, the amine donor agent has the formula: X-Y-Z, wherein X is an amine donor unit; Y is a linker; and Z is an agent moiety.

The number of the amine donor agents which may be conjugated via the acyl donor glutamine-containing tag (or the accessible/exposed/reactive endogenous glutamine) to the Fc-containing polypeptide is dependent on the number of acyl donor glutamine-containing tags (or the accessible/exposed/reactive endogenous glutamine) which are linked/inserted to the Fc-containing polypeptide(s) as well as the number of Gln on the acyl donor glutamine-containing tag (or the accessed/exposed endogenous glutamine). For example, two amine donor agents may be site-specifically conjugated to an antibody at the carboxyl termini of the two heavy chains and/or two amine donor agents may be site-specifically conjugated to the same antibody at the carboxyl termini of the two light chains.

The amine donor unit of the present invention is a primary amine ($NH_2$) that provides a substrate for transglutaminase to allow conjugation of the agent moiety to the Fc-containing polypeptide via the acyl donor glutamine-containing tag or the accessible/exposed/reactive endogenous glutamine. Accordingly, the linkage between the acyl donor glutamine-containing tag (or the accessible/exposed/reactive endogenous glutamine) and the amine donor unit is of the formula $CH_2$—$CH_2$—CO—NH—.

The linker of the present invention can be a cleavable or a non-cleavable linker. For example, the linker (with amine donor unit) or the amine donor agent can be released from the Fc-containing polypeptide. In some embodiments, the linker can be a peptide linker (e.g., conventional or nonconventional amino acid(s)) and/or a non-peptide linker. Examples of non-peptide linker include alkyl linker and PEG linker.

In some embodiments, the amine donor unit-linker (e.g., X-Y) is a linear unit comprising an agent moiety. In other embodiments, the amine donor unit-linker is a branched unit comprising at least about 2, 3, 4, 5, 6, 7, 8, 9, 10, 11, 12, or more agent moieties.

Exemplary amine donor unit-linkers include, but are not limited to, the amine donor unit-linker is selected from the group consisting of Ac-Lys-Gly, aminocaproic acid, Ac-Lys-β-Ala, amino-PEG2 (Polyethylene Glycol)-C2, amino-PEG3-C2, amino-PEG6-C2, Ac-Lys-Val (valine)-Cit (citrulline)-PABC (p-aminobenzyloxycarbonyl), aminocaproyl-Val-Cit-PABC, putrescine, and Ac-Lys-putrescine.

The agent moiety of the engineered Fc-containing polypeptide of the present invention includes a small molecule, a protein or polypeptide, and a biocompatible polymer.

In some embodiments, a small molecule is a cytotoxic agent, an immunosuppressive agent, or an imaging agent (e.g., a fluorophore). In some embodiments, the cytotoxic agent is a chemotherapeutic agent.

Examples of a cytotoxic agent include, but are not limited to, an anthracycline, an auristatin, a dolastatin, CC-1065, a duocarmycin, an enediyne, a geldanamycin, a maytansine, a puromycin, a taxane, a vinca alkaloid, SN-38, tubulysin, hemiasterlin, and stereoisomers, isosteres, analogs or derivatives thereof.

The anthracyclines are derived from bacteria *Strepomyces* and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., *Antimicrob. Agents Chemother.* 42:2961-2965 (1998). Exemplary dolastatins and auristatins include, but are not limited to, auristatin E, auristatin EB (AEB), auristatin EFP (AEFP), MMAD, MMAF, MMAE, and 5-benzoylvaleric acid-AE ester (AEVB).

Duocarmycin and CC-1065 are DNA alkylating agents with cytotoxic potency. See Boger and Johnson, *PNAS* 92:3642-3649 (1995). Exemplary dolastatins and auristatins include, but are not limited to, (+)-docarmycin A and (+)-duocarmycin SA, and (+)-CC-1065.

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, and dynemicin.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethylaminoethylamino-17-demethoxygeldanamycin).

Maytansines or their derivatives maytansinoids inhibit cell proliferation by inhibiting the mcirotubules formation during mitosis through inhibition of polymerization of tubulin. See Remillard et al., Science 189:1002-1005 (1975).

Exemplary maytansines and maytansinoids include, but are not limited to, mertansine (DM1) and its derivatives as well as ansamitocin.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Vinca alkyloids are also anti-tubulin agents. Exemplary vinca alkyloids include, but are not limited to, vincristine, vinblastine, vindesine, and vinorelbine.

In some embodiments, the agent moiety is an immunosuppressive agent. Examples of an immunosuppressive agent include, but are not limited to, gancyclovier, etanercept, tacrolimus, sirolimus, voclosporin, cyclosporine, rapamycin, cyclophosphamide, azathioprine, mycophenolgate mofetil, methotrextrate, and glucocorticoid and its analogs.

In some embodiments, the agent moiety is an imaging agent (e.g., a fluorophore), such as fluorescein, rhodamine, lanthanide phosphors, and their derivatives thereof. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101).

In some embodiments, the agent moiety is a polypeptide. In some embodiments, the polypeptide is an antibody, such as a humanized, human, chimeric, or murine monoclonal antibody.

In some embodiments, the agent moiety is a toxin polypeptide (or a toxin protein). Examples of a toxin polypeptide include, but are not limited to, diphtheria A chain, nonbinding active fragments of diphtheria toxin, exotoxin A chain, ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, tricothecenes, inhibitor cystine knot (ICK) peptides (e.g., ceratotoxins), and conotoxin (e.g., KIIIA or SmIIIa).

In some embodiments, therapeutic radioisotopes or other labels can be incorporated in the agent moiety for conjugation of an Fc-containing polypeptide to an amine donor agent. Examples of a radioisotope or other labels include, but are not limited to, $^3H$, $^{14}C$, $^{15}N$, $^{35}S$, $^{18}F$, $^{32}P$, $^{33}P$, $^{64}Cu$, $^{68}Ga$, $^{89}Zr$, $^{90}Y$, $^{99}Tc$, $^{123}I$, $^{124}I$, $^{125}I$, $^{131}I$, $^{111}In$, $^{131}In$, $^{153}Sm$, $^{186}Re$, $^{188}Re$, $^{211}At$, $^{212}Bi$, and $^{153}Pb$.

In some embodiments, the agent moiety is a biocompatible polymer. The Fc-containing polypeptide can be conjugated to the biocompatible polymer via the acyl donor glutamine-containing tag or the accessible/exposed/reactive endogenous glutamine to improve the biological characteristics of the Fc-containing polypeptide, e.g., to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

In some embodiments, the amine donor agent (X-Y-Z) is

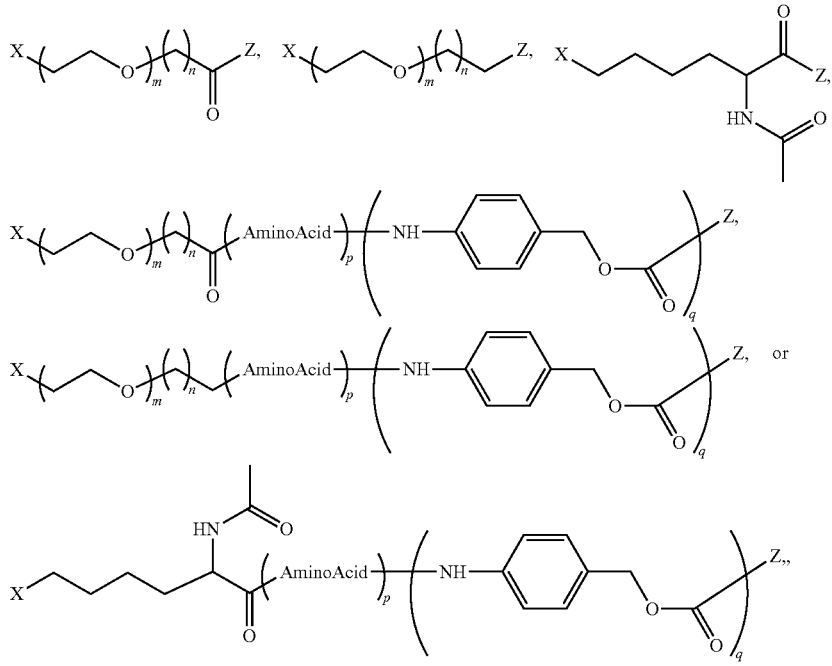

wherein X is $NH_2$ (i.e., thus forming a covalent bond with glutamine as $CH_2$—$CH_2$—CO'NH—), m is a 0 to 20, n is 1 to 8, p is 0 to 3, q is 0 or 1, amino acid is any conventional or nonconventional amino acid and Z is a cytotoxic agent or an imaging agent.

Conventional or naturally occurring amino acids are divided into groups based on common side-chain properties: (1) non-polar: Norleucine, Met, Ala, Val, Leu, Ile; (2) polar without charge: Cys, Ser, Thr, Asn, Gln; (3) acidic (negatively charged): Asp, Glu; (4) basic (positively charged): Lys, Arg; and (5) residues that influence chain orientation:

Gly, Pro; and (6) aromatic: Trp, Tyr, Phe, His. Conventional amino acids include L or D stereochemistry.

Unconventional amino acids are non-naturally occurring amino acids. Examples of an uncoventioanl amino acid include, but are not limited to, aminoadipic acid, beta-alanine, beta-aminopropionic acid, aminobutyric acid, piperidinic acid, aminocaprioic acid, aminoheptanoic acid, aminoisobutyric acid, aminopimelic acid, citrulline, diaminobutyric acid, desmosine, diaminopimelic acid, diaminopropionic acid, N-ethylglycine, N-ethylaspargine, hyroxylysine, allo-hydroxylysine, hydroxyproline, isodesmosine, allo-isoleucine, N-methylglycine, sarcosine, N-methylisoleucine, N-methylvaline, norvaline, norleucine, orithine, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and amino acids (e.g., 4-hydroxyproline).

In some embodiments, the amine donor agent is selected from the group consisting of Alexa 488 cadaverine, 5-FITC cadaverine, Alexa 647 cadaverine, Alexa 350 cadaverine, 5-TAMRA cadaverine, 5-FAM cadaverine, SR101 cadaverine, 5,6-TAMRA cadaverine, 5-FAM lysine, Ac-Lys-Gly-MMAD, amino-PEG3-C2-MMAD, amino-PEG6-C2-MMAD, amino-PEG3-C2-amino-nonanoyl-MMAD], aminocaproyl-Val-Cit-PABC-MMAD, Ac-Lys-β-Ala-MMAD, Aminocaproyl-MMAD, Ac-Lys-Val-Cit-PABC-MMAD, Aminocaproyl-MMAE, amino-PEG3-C2-MMAE, amino-PEG2-C2-MMAE, Aminocaproyl-MMAF, Aminocaproyl-Val-Cit-PABC-MMAE, Aminocaproyl-Val-Cit-PABC-MMAF, amino-PEG2-C2-MMAF, amino-PEG3-C2-MMAF, putrescinyl-geldanamycin, and Ac-Lys-putrescinyl-geldanamycin. In some embodiments, the amine donor agent is aminocaproyl-Val-Cit-PABC-MMAE, aminocaproyl-Val-Cit-PABC-MMAF, Ac-Lys-putrescinyl-geldanamycin, Ac-Lys-β-Ala-MMAD, Ac-Lys-Val-Cit-PABC-MMAD, aminocaproyl-Val-Cit-PABC-MMAD, or amino-PEG6-C2-MMAD. In some embodiments, the acyl donor glutamine-containing tag comprises the amino acid sequence LLQGG (SEQ ID NO:2) and the amine donor agent is aminocaproyl-Val-Cit-PABC-MMAE, aminocaproyl-Val-Cit-PABC-MMAF, aminocaproyl-Val-Cit-PABC-MMAD, Ac-Lys-putrescinyl-geldanamycin, Ac-Lys-β-Ala-MMAD, Ac-Lys-Val-Cit-PABC-MMAD, or amino-PEG6-C2-MMAD. Exemplary structures of the amine donor agent are listed in Table 1.

TABLE 1
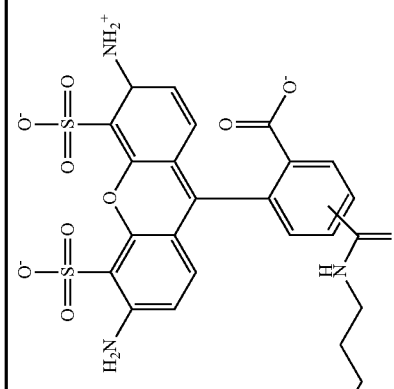
Alexa 488 cadaverine
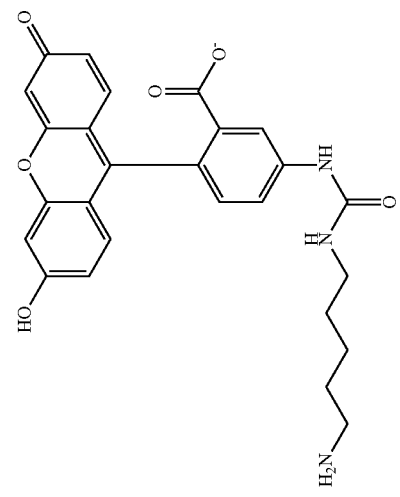
5-FITC cadaverine
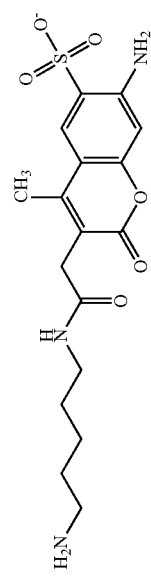
Alexa 350 cadaverine TABLE 1-continued
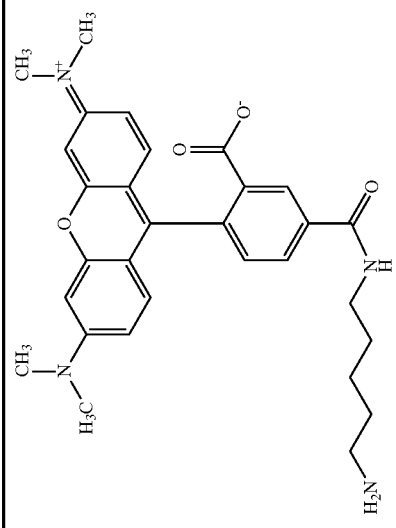
5-TAMRA cadaverine
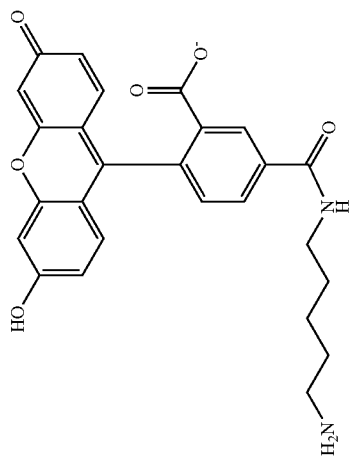
5-FAM cadaverine TABLE 1-continued
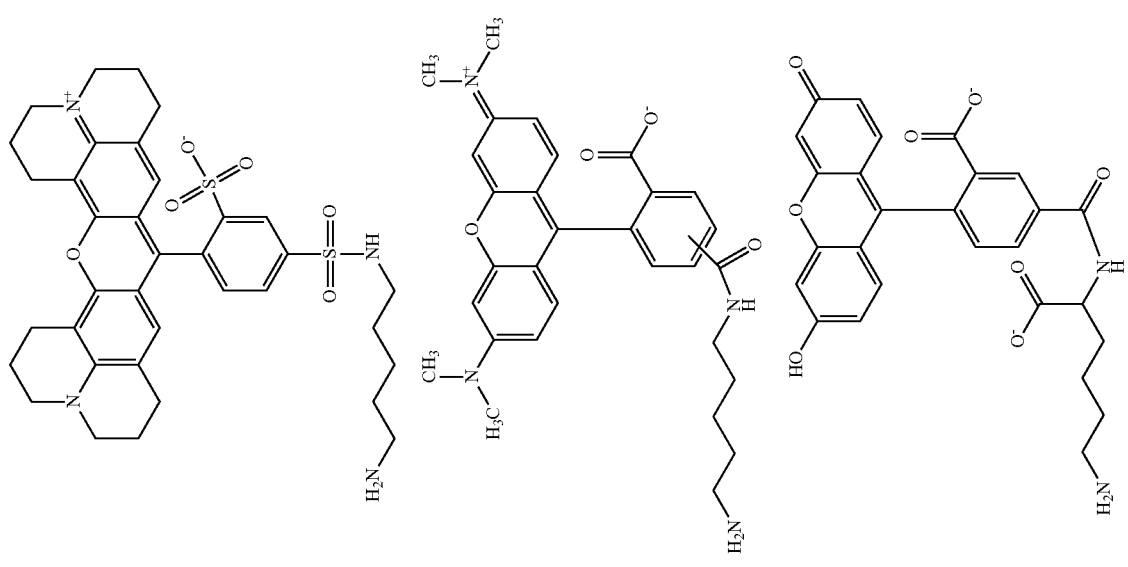
SR101 cadaverine
5,6-TAMRA cadaverine
5-FAM lysine TABLE 1-continued
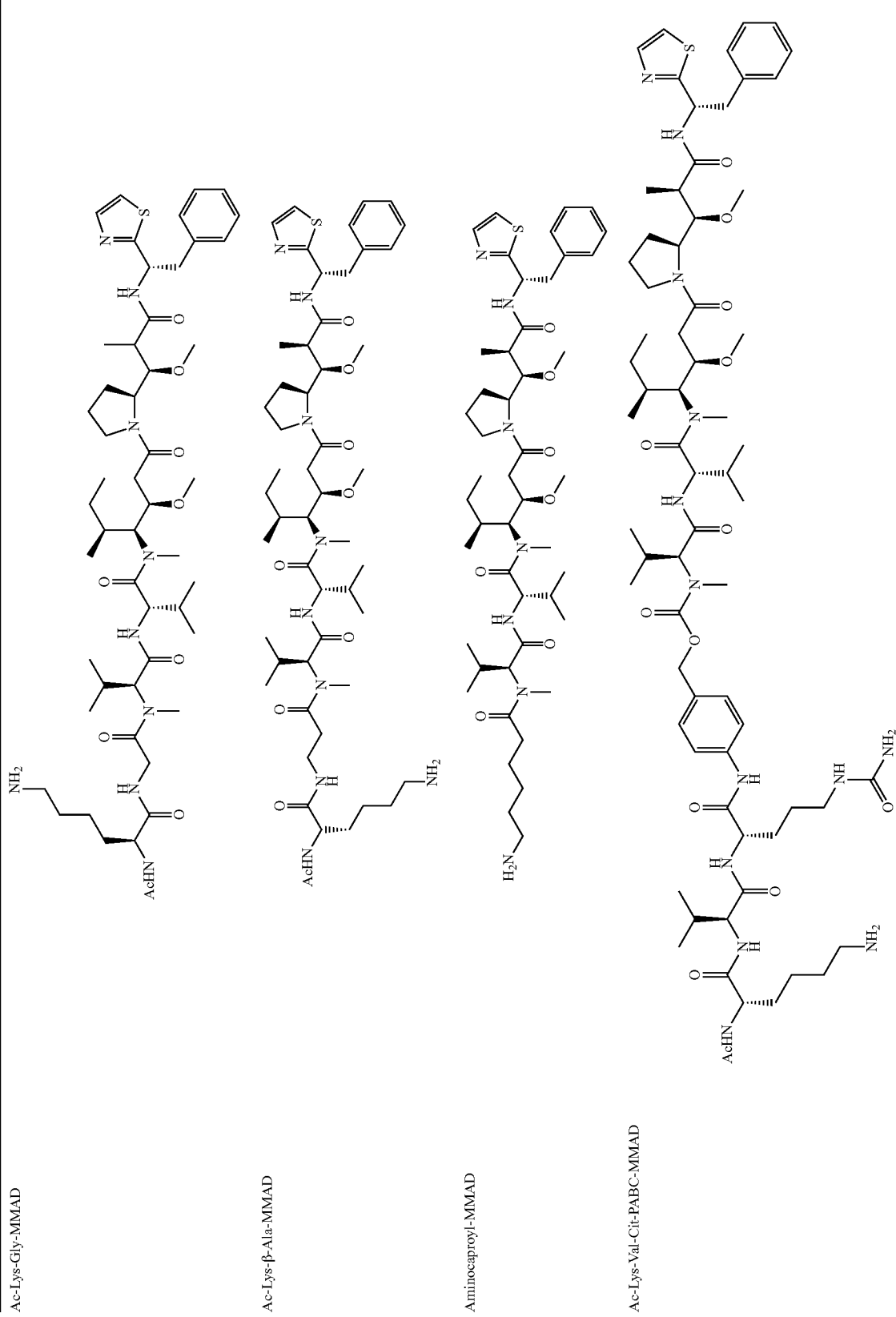
Ac-Lys-Gly-MMAD
Ac-Lys-β-Ala-MMAD
Aminocaproyl-MMAD
Ac-Lys-Val-Cit-PAB TABLE 1-continued
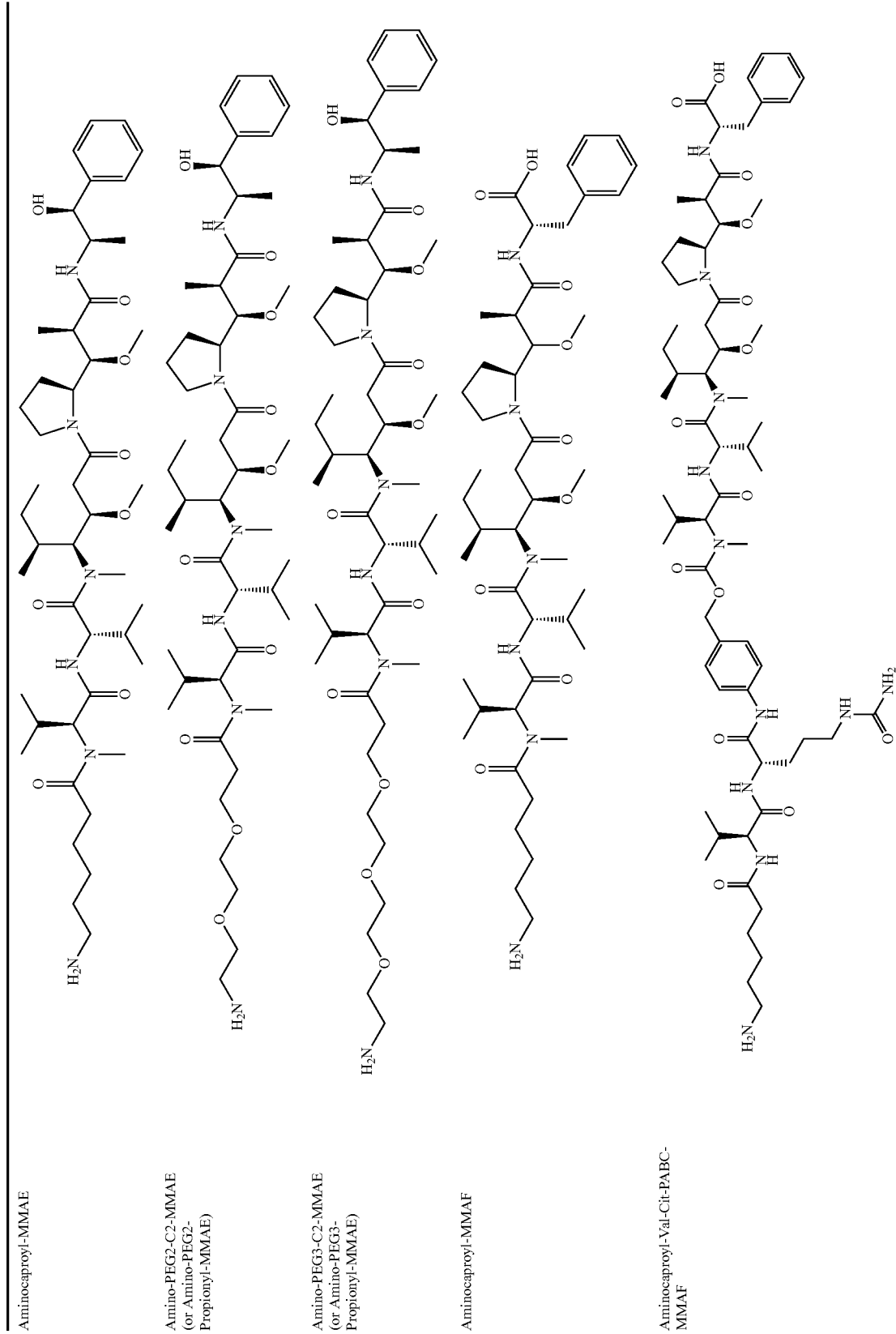

TABLE 1-continued

| Amino-PEG3-C2-MMAD (or Amino-PEG3-Propionyl-MMAD) |
| Amino-PEG6-C2-MMAD (or Amino-PEG6-Propionyl-MMAD) |
| Amino-PEG3-C2-amino-nonanoyl-MMAD (or Amino-PEG3-Propionyl-amino-nonanoyl-MMAD) |
| Amino-nonanoyl-MMAD |

TABLE 1-continued
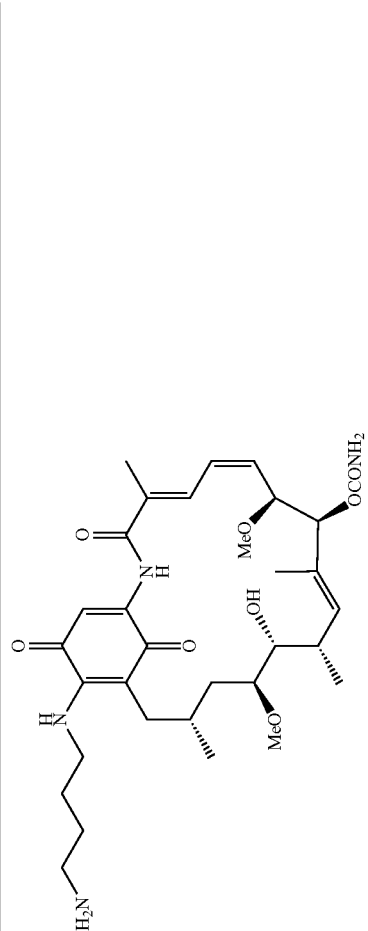
Putresciny1-Geldanamycin
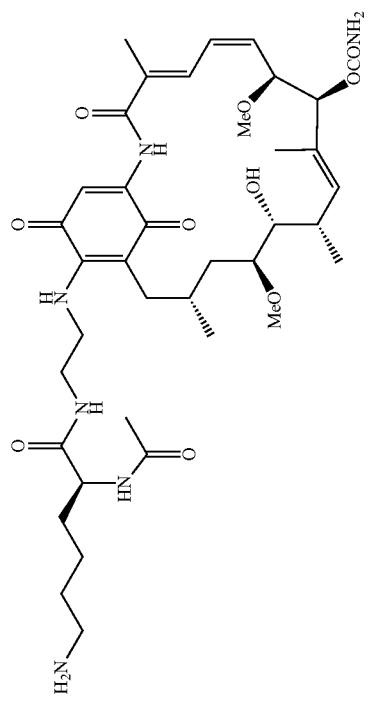
Ac-Lys-Putresciny1-Geldanamycin TABLE 1-continued
| Maytansine analogue | 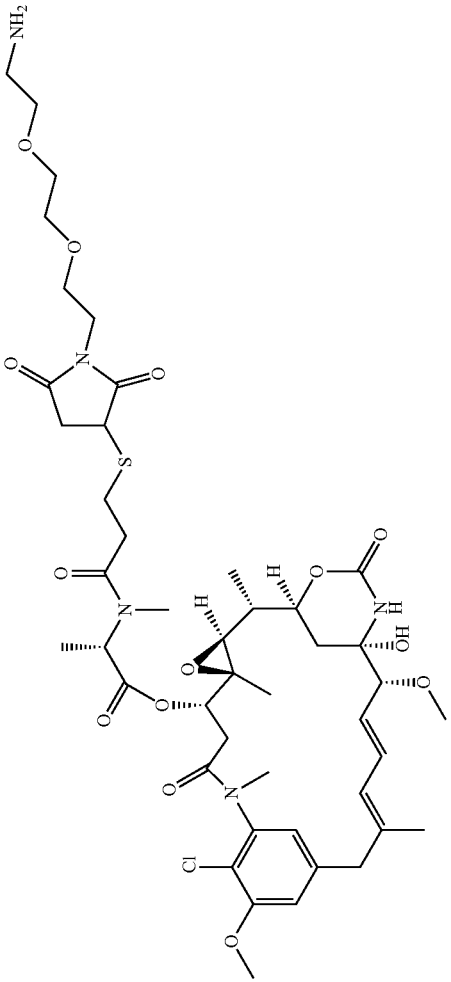 |

In another aspect, the invention provides an engineered Fc-containing polypeptide conjugate comprising the formula: (Fc-containing polypeptide)-T-A, wherein the Fc-containing polypeptide comprises a first Fc-containing polypeptide; wherein T is an acyl donor glutamine-containing tag engineered at a specific site or comprises an endogenous glutamine made reactive by the first Fc-containing polypeptide engineering; wherein A is an amine donor agent; wherein the amine donor agent comprises a second Fc-containing polypeptide and a tag and does not comprise a reactive Gln; and wherein the acyl donor glutamine-containing tag or the endogenous glutamine is site-specifically crosslinked to the first Fc-containing polypeptide and the second Fc-containing polypeptide. In some embodiments, the engineered Fc-containing polypeptide conjugate is a bispecific Fc-containing polypeptide (e.g., bispecific antibody). In some embodiments, the acyl donor glutamine-containing tag or the endogenous glutamine is not spatially adjacent to a reactive Lys (i.e., the ability to form a covalent bond as an amine donor in the presence of an acyl donor and a transglutaminase) in the first Fc-containing polypeptide.

In some embodiments, the tag in the amine donor agent comprises a G or GG and the tag is spatially adjacent to a reactive Lys in the second Fc-containing polypeptide. Accordingly, the acyl donor glutamine-containing tag (or the accessible/exposed/reactive endogenous glutamine) and the reactive Lys in the second Fc-containing polypeptide of the engineered Fc-containing polypeptide conjugate are substrates for transglutaminase, and the linkage between the acyl donor glutamine-containing tag (or the endogenous glutamine) and the reactive Lys in the second Fc-containing polypeptide is of the formula $CH_2-CH_2-CO-NH-$.

In some embodiments, the tag is an amine donor tag (i.e., K-tag) comprising a Lys. In some embodiments, the amine donor tag comprises an amino acid sequence KG. In some embodiments, the amine donor tag comprises an amino acid sequence selected from the group consisting of KGG, GKGG (SEQ ID NO:11), GSKGG (SEQ ID NO:12), GSGKGG (SEQ ID NO:13), and GSGGKGG (SEQ ID NO:14). Accordingly, the acyl donor glutamine-containing tag (or the accessible/exposed/reactive endogenous glutamine) and the amine donor tag of the engineered Fc-containing polypeptide conjugate are substrates for transglutaminase, and the linkage between the acyl donor glutamine-containing tag (or the endogenous glutamine) and the amine donor tag is of the formula $CH_2-CH_2-CO-NH-$.

In another aspect, the invention provides an engineered Fc-containing polypeptide conjugate comprising the formula: (Fc-containing polypeptide)-T-A, wherein the Fc-containing polypeptide comprises a first Fc-containing polypeptide; wherein T is an acyl donor glutamine-containing tag engineered at a specific site; wherein A is an amine donor agent; wherein the amine donor agent comprises a second Fc-containing polypeptide and does not comprise a reactive Gln; and wherein the acyl donor glutamine-containing tag is site-specifically crosslinked to the first Fc-containing polypeptide and the second Fc-containing polypeptide. In some embodiments, the engineered Fc-containing polypeptide conjugate is a bispecific Fc-containing polypeptide (e.g., bispecific antibody). In some embodiments, the acyl donor glutamine-containing tag and a reactive Lys (i.e., an endogenous reactive Lys) in the second Fc-containing polypeptide are substrates for transglutaminase, and the linkage between the acyl donor glutamine-containing tag and the reactive Lys in the second Fc-containing polypeptide is of the formula $CH_2-CH_2-CO-NH'$. In some embodiments, the acyl donor glutamine-containing tag is not spatially adjacent to a reactive Lys in the first Fc-containing polypeptide In another aspect, the invention provides an engineered Fc-containing polypeptide conjugate comprising the formula: (Fc-containing polypeptide)-T-A, wherein the Fc-containing polypeptide comprises a first Fc-containing polypeptide and a second Fc-containing polypeptide; wherein T is an acyl donor glutamine-containing tag comprising a first acyl donor glutamine-containing tag and a second acyl donor glutamine-containing tag crosslinked to the first Fc-containing polypeptide and the second Fc-containing polypeptide, respectively; wherein A is an amine donor agent; and wherein the first and the second acyl donor glutamine-containing tags are site-specifically crosslinked to each other. In some embodiments, the amine donor agent does not comprise a reactive Gln. In some embodiments, the engineered Fc-containing polypeptide conjugate is a bispecific Fc-containing polypeptide (e.g., bispecific antibody). In some embodiments, the first acyl donor glutamine-containing tag and the second acyl donor glutamine-containing tag are not spatially adjacent to a reactive Lys in the first Fc-containing polypeptide and the second Fc-containing polypeptide, respectively.

In some embodiments, the amine donor agent is a compound comprising a diamine. Examples of a compound comprising a diamine include, but are not limited to, putrescine (butane-1,4-diamine), ethylenediamine, cadaverine (pentane-1,5-diamine), spermidine, spermine, hydrazine, 1,3-diaminopropane, hexamethylenediamine, phenylenediamine (e.g., o-phenylenediamine, m-phenylenediamine, or p-phenylenediamine), xylylenediamine (e.g., o-xylylenediamine, m-xylyenediamine, or p-xylylenediamine), diphenylethylenediamine, 1,8-diaminonapthalene, and stereoisomers, isosteres, analogs or derivatives thereof. In some embodiments, the amine donor agent is putrescine or cadaverine.

In another aspect, the invention provides an engineered Fc-containing polypeptide conjugate comprising the formula: (Fc-containing polypeptide)-T-A, wherein the Fc-containing polypeptide comprises a first Fc-containing polypeptide and a second Fc-containing polypeptide; wherein T is an acyl donor glutamine-containing tag crosslinked to the first Fc-containing polypeptide; wherein A is an amine donor agent; and wherein the acyl donor glutamine-containing tag is site-specifically crosslinked to the second Fc-containing polypeptide. In some embodiments, the amine donor agent does not comprise a reactive Gln. In some embodiments, the acyl donor glutamine-containing tag is not adjacent to a reactive Lys in the first Fc-containing polypeptide. In some embodiments, the engineered Fc-containing polypeptide conjugate is a bispecific Fc-containing polypeptide (e.g., bispecific antibody). In some embodiments, the acyl donor glutamine-containing tag and the reactive Lys (i.e., an endogenous reactive Lys) in the second Fc-containing polypeptide are substrates for transglutaminase, and the linkage between the acyl donor glutamine-containing tag and the reactive Lys in the second Fc-containing polypeptide is of the formula $CH_2-CH_2-CO-NH-$.

In some embodiments, the effector function (e.g., as measured by Fcγ3 and/or C1q binding) of the engineered bispecific Fc-containing polypeptide conjugate decreases no greater than about any of 1-fold, 2-fold, 3-fold, 4-fold, or 5-fold relative to a wild type bispecific Fc-containing polypeptide. In some embodiments, the engineered Fc-containing polypeptide conjugate is a bispecific IgG, wherein the effector function of the bispecific IgG decreases no greater than about 2-fold relative to a wild type bispecific IgG. In other embodiments, the effector function of the bispecific IgG decreases about 2-fold relative to a wild type bispecific IgG. In other embodiments, the effector function of the bispecific IgG decreases more than about 2-fold relative to a wild type bispecific IgG. In some embodiments, the engineered bispecific Fc-containing polypeptide conjugate is a bispecific IgG, wherein the effector function of the bispecific IgG decreases no greater than about 1-fold relative to a wild type bispecific IgG. In other embodiments, the effector function of the bispecific IgG decreases about 1-fold relative to a wild type bispecific IgG. In some embodiments, the effector function of the bispecific IgG decreases more than about any of 1-fold, 3-fold, 4-fold, or 5-fold relative to a wild type bispecific IgG.

In some embodiments, the effector function (e.g., as measured by Fcγ3 and/or C1q binding) of the engineered Fc-containing polypeptide conjugate increases at least about any of 1-fold to 300-fold relative to a wild type Fc-containing polypeptide. In some embodiments, the engineered Fc-containing polypeptide conjugate is a bispecific IgG, wherein the effector function of the bispecific IgG increases at least about any of 1- to 5-fold, 6- to 10-fold, 11- to 15-fold, 16- to 20-fold, 21- to 25-fold, 26- to 30-fold, 31- to 35-fold, 36- to 40-fold, 41- to 45-fold, 46- to 50-fold, 51- to 55-fold, 56- to 60-fold, 61- to 65-fold, 66- to 70-fold, 71- to 75-fold, 76- to 80-fold, 81- to 85-fold, 86- to 90-fold, 91- to 95-fold, 96- to 100-fold, 101- to 200-fold, 201- to 300-fold, 301- to 500-fold, 501- to 1000-fold, 1001- to 1500-fold, 1501- to 2000-fold, 2001- to 2500-fold, 2501- to 3000-fold relative to a wild type bispecific IgG. In some embodiments, the effector function of the bispecific IgG increases about any of 2-fold, 3-fold, 4-fold, 5-fold, 10-fold, 15-fold, 20-fold, 40-fold, 60-fold, 80-fold, 100-fold, 150-fold, 200-fold, 250-fold, 300-fold, 400-fold, 500-fold, 600-fold, 700-fold, 800-fold, 900-fold, 1000-fold, 1500-fold, 2000-fold, 2500-fold, or 3000-fold relative to a wild type bispecific IgG.

In some embodiments, the engineered bispecific Fc-containing polypeptide conjugate (e.g., bispecific antibody) can be modified or derivatized, such as by making an engineered fusion Fc-containing polypeptide conjugate disclosed herein linked to another polypeptide or molecular agent. For example, the engineered bispecific Fc-containing polypeptide can be modified or derivatized with a chemical group, including but not limited to PEG, a methyl or ethyl group, an ester, a carbohydrate group and the like, using well known techniques by persons skilled in the art. These chemical groups (and others like them which have been used to stability therapeutic compounds in vivo) are useful to improve the biological characteristics of the engineered bispecific Fc-containing polypeptide conjugate, e.g., to increase serum half-life and bioactivity, or extend in vivo half-lives.

In some embodiments, the engineered bispecific Fc-containing polypeptide conjugate described herein can be labeled using any of a multitude of methods known in the art. In some embodiments, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In some embodiments, the label or marker can be therapeutic, e.g., a drug conjugate or toxin as described herein. Examples of labels for polypeptides include, but are not limited to: radioisotopes or radionuclides, fluorescent labels, enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs, stereoisomers, isosteres, or homologs thereof. In some embodiments, labels are attached by spacer arms of various lengths to reduce potential steric hindrance.

In another aspect, the invention provides an engineered Fab-containing polypeptide conjugate comprising the formula: (Fab-containing polypeptide)-T-A, wherein T is an acyl donor glutamine-containing tag engineered at a specific site or comprises an endogenous glutamine made reactive by the Fab-containing polypeptide engineering; wherein A is an amine donor agent, wherein the amine donor agent is a biocompatible polymer comprising a reactive amine, and wherein the biocompatible polymer is site-specifically conjugated to the acyl donor glutamine-containing tag or the endogenous glutamine at a carboxyl terminus, an amino terminus, or elsewhere at an another site in the Fab-containing polypeptide. For example, the Fab-containing polypeptide can be site-specifically conjugated to the biocompatible polymer via the acyl donor glutamine-containing tag or the accessible/exposed/reactive endogenous glutamine as described herein to improve the biological characteristics of the Fab-containing polypeptide, e.g., to increase the serum half-life and bioactivity, and/or to extend its in vivo half-lives. In some embodiments, biocompatible polymer is a water soluble polymer such as a PEG derivative or a zwitterion-containing biocompatible polymer. In some embodiments, the acyl donor glutamine-containing tag comprises at least one Gln. In some embodiments, the acyl donor glutamine-containing tag comprises an amino acid sequence XXQX (SEQ ID NO:1), wherein X is L (Leu), A (Ala), G (Gly), S (Ser), V (Val), F (Phe), Y (Tyr), H (His), R (Arg), N (Asn), E (Glu), D (Asp), C (Cys), Q (Gln), I (Ile), M (Met), P (Pro), T (Thr), K (Lys), or W (Trp). In some embodiments, the acyl donor glutamine-containing tag comprises an amino acid sequence selected from the group consisting of LLQGG (SEQ ID NO:2), LLQG (SEQ ID NO:3), LSLSQG (SEQ ID NO:4), GGGLLQGG (SEQ ID NO:5), GLLQG (SEQ ID NO:6), LLQ, GSPLAQSHGG (SEQ ID NO:7), GLLQGGG (SEQ ID NO:8), GLLQGG (SEQ ID NO:9), GLLQ (SEQ ID NO:10), LLQLLQGA (SEQ ID NO:47), LLQGA (SEQ ID NO:48), LLQYQGA (SEQ ID NO:49), LLQGSG (SEQ ID NO:50), LLQYQG (SEQ ID NO:51), LLQLLQG (SEQ ID NO:52), SLLQG (SEQ ID NO:53), LLQLQ (SEQ ID NO:54), LLQLLQ (SEQ ID NO:55), and LLQGR (SEQ ID NO:56). In some embodiments, the acyl donor glutamine-containing tag comprises an amino acid sequence selected from the group consisting of QVQLKE (SEQ ID NO:39) and VQLKE (SEQ ID NO:40). Accordingly, both the acyl donor glutamine-containing tag (or the endogenous glutamine) and the biocompatible polymer are substrates for transglutaminase, and the linkage between the acyl donor glutamine-containing tag (or the endogenous glutamine) and the biocompatible polymer is of the formula $CH_2-CH_2-CO-NH-$.

The reactive amine in the biocompatible polymer can be a primary amine. In some embodiments, primary amine in the biocompatible polymer is an endogenous primary amine or an exogenous primary amine. An amine donor tag comprising a Lys as described herein can be added or engineered to the biocompatible polymer to provide an exogenous primary amine. In some embodiments, the amine donor tag comprises a Lys. In some embodiments, the amine donor tag comprises an amino acid sequence KG. In some embodiments, the amine donor tag comprises an amino acid sequence selected from the group consisting of KGG, GKGG (SEQ ID NO:11), GSKGG (SEQ ID NO:12), GSGKGG (SEQ ID NO:13), and GSGGKGG (SEQ ID NO:14).

In some embodiments, the acyl donor glutamine-containing tag or the endogenous glutamine (accessible/exposed/reactive) is located at the Fab-containing polypeptide at the carboxyl terminus of a heavy chain, a light chain, or both the heavy chain and the light chain. In some embodiments, the acyl donor glutamine-containing tag comprises a first acyl donor glutamine-containing tag and a second acyl donor glutamine-containing tag, wherein the first acyl donor glutamine-containing tag is located at the carboxyl terminus of the heavy chain, and a second acyl donor glutamine-containing tag is located at the carboxyl terminus of the light chain. In some embodiments, the acyl donor glutamine-containing tag or the endogenous glutamine (accessible/exposed/reactive) is located at the Fab-containing polypeptide at the amino terminus of a heavy chain, a light chain, or both the heavy chain and the light chain. In some embodiments, the acyl donor glutamine-containing tag comprises a first acyl donor glutamine-containing tag and a second acyl donor glutamine-containing tag, wherein the first acyl donor glutamine-containing tag is located at the amino terminus of a heavy chain, and a second acyl donor glutamine-containing tag is located at the amino terminus of a light chain.

In some embodiments, the acyl donor glutamine-containing tag is located at or inserted at an another site in the Fab-containing polypeptide, wherein the another site is not an amino or a carboxyl terminus. For example, the acyl donor glutamine-containing tag is part of an antibody loop. The acyl donor glutamine-containing tag can be linked to one or more heavy chain loop(s). The acyl donor glutamine-containing tag can also be linked one or more light chain loop(s) of the antibody. In some embodiments, the acyl donor glutamine-containing tag is linked to both a heavy chain and a light chain loops.

In some embodiments, the Fab-containing polypeptide comprises an antibody. In some embodiments, the antibody is a monoclonal antibody, a polyclonal antibody, a human antibody, a humanized antibody, a chimeric antibody, a bispecific antibody, or an antibody fragment. In some embodiments, the antibody is an IgG. In some embodiments, the IgG is selected from the group consisting of IgG1, IgG2, IgG3, and IgG4. In some embodiments, the antibody is an IgA, IgE, IgD, or IgM.

In another aspect, the invention provides an engineered toxin polypeptide conjugate comprising the formula: (toxin polypeptide)-T-A, wherein T is an acyl donor glutamine-containing tag engineered at a specific site or an endogenous glutamine made reactive by the toxin polypeptide engineering; wherein A is an amine donor agent, wherein the amine donor agent is a biocompatible polymer comprising a reactive amine, and wherein the biocompatible polymer is site-specifically conjugated to the acyl donor glutamine-containing tag or the endogenous glutamine at a carboxyl terminus, an amino terminus, or elsewhere at an another site in the toxin polypeptide. For example, the toxin polypeptide can be site-specifically conjugated to the biocompatible polymer via the acyl donor glutamine-containing tag or the endogenous glutamine (accessible/exposed/reactive) as described herein to improve the biological characteristics of the toxin polypeptide, e.g., to increase the serum half-life and bioactivity, and/or to extend its in vivo half-lives. In some embodiments, toxin polypeptide is a ceratotoxin or a conotoxin (e.g., KIIIA or SmIIIa). In some embodiments, the biocompatible polymer is a water soluble polymer such as PEG derivative or a zwitterion-containing biocompatible polymer. In some embodiments, the acyl donor glutamine-containing tag comprises at least one Gln. In some embodiments, the acyl donor glutamine-containing tag comprises an amino acid sequence XXQX (SEQ ID NO:1), wherein X is L (Leu), A (Ala), G (Gly), S (Ser), V (Val), F (Phe), Y (Tyr), H (His), R (Arg), N (Asn), E (Glu), D (Asp), C (Cys), Q (Gln), I (Ile), M (Met), P (Pro), T (Thr), K (Lys), or W (Trp). In some embodiments, the acyl donor glutamine-containing tag comprises an amino acid sequence selected from the group consisting of LLQGG (SEQ ID NO:2), LLQG (SEQ ID NO:3), LSLSQG (SEQ ID NO:4), GGGLLQGG (SEQ ID NO:5), GLLQG (SEQ ID NO:6), LLQ, GSPLAQSHGG (SEQ ID NO:7), GLLQGGG (SEQ ID NO:8), GLLQGG (SEQ ID NO:9), GLLQ (SEQ ID NO:10), LLQLLQGA (SEQ ID NO:47), LLQGA (SEQ ID NO:48), LLQYQGA (SEQ ID NO:49), LLQGSG (SEQ ID NO:50), LLQYQG (SEQ ID NO:51), LLQLLQG (SEQ ID NO:52), SLLQG (SEQ ID NO:53), LLQLQ (SEQ ID NO:54), LLQLLQ (SEQ ID NO:55), and LLQGR (SEQ ID NO:56). In some embodiments, the acyl donor glutamine-containing tag comprises an amino acid sequence selected from the group consisting of QVQLKE (SEQ ID NO:39) and VQLKE (SEQ ID NO:40). Accordingly, both the acyl donor glutamine-containing tag (or the endogenous glutamine) and the biocompatible polymer are substrates for transglutaminase, and the linkage between the acyl donor glutamine-containing tag (or the endogenous glutamine) and the biocompatible polymer is of the formula $CH_2$—$CH_2$—CO—NH—.

In some embodiments, the acyl donor glutamine-containing tag is located at the carboxyl terminus of the toxin polypeptide. In some embodiments, the acyl donor glutamine-containing tag is located at the amino terminus of the toxin polypeptide. In some embodiments, the acyl donor glutamine-containing tag is located elsewhere at an another site of the toxin polypeptide.

In one variation, the invention provides an engineered toxin polypeptide conjugate comprising the formula: (toxin polypeptide)-T-B, wherein T is an acyl donor glutamine-containing tag engineered at a specific site; wherein B is a biocompatible polymer, and wherein the toxin polypeptide is site-specifically conjugated to the acyl donor glutamine-containing tag at an any site in the biocompatible polymer.

In some embodiments, the acyl donor glutamine-containing tag or the endogenous glutamine in the biocompatible polymer is spatially adjacent to a reactive Lys (e.g., reactive endogenous Lys) in the toxin polypeptide. In some embodiments, the toxin polypeptide comprises an amine donor tag as described herein. For example, the amine donor tag comprising a Lys can be linked to the toxin polypeptide.

Exemplary structures of the (toxin polypeptide)-(acyl donor glutamine-containing tag), biocompatible polymer, and the resulting (toxin polypeptide)-(acyl donor glutamine-containing tag)-(biocompatible polymer) are listed below:

DCLGWFKSCDPKNDKCCKNYTCSRRDRWCKYDLLQGG + H$_2$N~~~(O~~~)$_n$OH

Ceratotoxin-Qtag          Amino-PEG

↓

Ceratotoxin-PEG

Ceratotoxin-Qtag corresponds to SEQ ID NO: 81.

Exemplary structures of the (toxin polypeptide)-(amine donor tag), (acyl donor glutamine-containing tag)-(biocompatible polymer), and the resulting (toxin polypeptide)-(amine donor tag)-(acyl donor glutamine-containing tag)-(biocompatible polymer) are listed below QRCCNGRRGCSSRWCRDHSRCC-Ktag + LLQGG~~~(O~~~)$_n$OH SmIIIA-Ktag          Q-tag PEG

↓

SmIIIa-PEG

SmIIIA corresponds to SEQ ID NO: 82.

Methods for Making the Engineered Polypeptide Conjugate

The methods for making the engineered polypeptide conjugates described herein are also provided in the present invention. In one aspect, the invention provides a method for preparing an engineered Fc-containing polypeptide conjugate comprising the formula: (Fc-containing polypeptide)-T-A, wherein T is an acyl donor glutamine-containing tag engineered at a specific site or comprises an endogenous glutamine made reactive by the Fc-containing polypeptide engineering; wherein A is an amine donor agent; and wherein the amine donor agent is site-specifically conjugated to the acyl donor glutamine-containing tag or the endogenous glutamine at a carboxyl terminus, an amino terminus, or elsewhere at an another site in the Fc-containing polypeptide, comprising the steps of: a) providing an engineered (Fc-containing polypeptide)-T molecule comprising the Fc-containing polypeptide located at the acyl donor glutamine-containing tag or the endogenous glutamine; b) contacting the amine donor agent with the engineered (Fc-containing polypeptide)-T molecule in the presence of a transglutaminase; and c) allowing the engineered (Fc-containing polypeptide)-T to covalently link to the amine donor agent to form the engineered Fc-containing polypeptide conjugate.

In some embodiments, the engineered Fc-containing polypeptide conjugate prepared using the methods described herein has conjugation efficiency of at least about 51%. In some embodiments, the engineered Fc-containing polypeptide conjugate has conjugation efficiency of at least about any of 51%-60%, 61%-70%, 71%-80%, 81%-90%, or 91%-100%. In some embodiments, the engineered Fc-containing polypeptide conjugate has conjugation efficiency of about any of 55%, 60%, 65%, 70%, 75%, 80%, 85%, 90%, 91%, 92%, 93%, 94%, 95%, 96%, 97%, 98%, 99%, or 100%. In some embodiments, the acyl donor glutamine-containing tag comprises the amino acid sequence LLQGG (SEQ ID NO:2), Q, LLQLLQGA (SEQ ID NO:47), LLQG (SEQ ID NO:3), LLQGA (SEQ ID NO:48), LLQGSG (SEQ ID NO:50), LLQYQG (SEQ ID NO:51), LLQLQG (SEQ ID NO:52), SLLQG (SEQ ID NO:53), LLQLQ (SEQ ID NO:54), LLQLLQ (SEQ ID NO:55), or LLQGR (SEQ ID NO:56).

In some embodiments, the engineered Fc-containing polypeptide conjugate comprises a first and a second acyl donor glutamine-containing tags, wherein the first acyl donor glutamine-containing tag comprising the amino acid sequence LLQGG (SEQ ID NO:2) is located at the carboxyl terminus of the heavy chain of the Fc-containing polypeptide, the second acyl donor glutamine-containing tag comprising the amino acid sequence GGGLLQGG (SEQ ID NO:5) is located at the carboxyl terminus of the light chain of the Fc-containing polypeptide, and the conjugation efficiency of the engineered Fc-containing polypeptide conjugate prepared using the methods described herein is at least about 65%.

In some embodiments, the engineered Fc-containing polypeptide conjugate comprises a first and a second acyl donor glutamine-containing tags, wherein the first acyl donor glutamine-containing tag comprising the amino acid sequence LLQG (SEQ ID NO:3) replaces wild-type amino acid positions 190-192 (Kabat numbering scheme) in the Fc-containing polypeptide (i.e., IgG1), the second acyl donor glutamine-containing tag comprising the amino acid sequence LLQGA (SEQ ID NO:48) replaces wild-type amino acid K at the carboxyl terminus of the Fc-containing polypeptide, and the conjugation efficiency of the engineered Fc-containing polypeptide conjugate prepared using the methods described herein is at least about 80%.

In some embodiments, the conjugation efficiency of the engineered Fc-containing polypeptide conjugate comprising an amino acid modification (e.g., deletion, insertion, substitution, or mutation) at the last amino acid position in the carboxyl terminus of the Fc-containing polypeptide has an increased conjugation efficiency relative to the same engineered Fc-containing polypeptide conjugate without the amino acid modification at the same position. In some embodiments, the conjugation efficiency increases by at least about 5% to about 99%. In some embodiments, the conjugation efficiency increases by about any of 5%, 10%, 15%, 25%, 30%, 35%, 40%, 45%, 50%, 55%, 60%, 65%, 70%, 75%, 80%, 85%, 90%, 95%, 96%, 97%, 98%, or 99%. In some embodiments, the amino acid modification is a substitution comprising a replacement of a wild type amino acid with Arg. In some embodiments, the amino acid modification is an insertion of one or more amino acid (e.g., Arg). In some embodiments, the amino acid modification is an amino acid deletion.

In some embodiments, the conjugation efficiency of the engineered Fc-containing polypeptide conjugate comprising an amino acid modification (e.g., deletion, insertion, substitution, or mutation) at the first amino acid position in the amino terminus of the Fc-containing polypeptide has an increased conjugation efficiency relative to the same engineered Fc-containing polypeptide conjugate without the amino acid modification at the same position. In some embodiments, the conjugation efficiency increases by at least about 5% to about 99%. In some embodiments, the conjugation efficiency increases by about any of 5%, 10%, 15%, 25%, 30%, 35%, 40%, 45%, 50%, 55%, 60%, 65%, 70%, 75%, 80%, 85%, 90%, 95%, 96%, 97%, 98%, or 99%. In some embodiments, the amino acid modification is a substitution comprising a replacement of a wild type amino acid with Gln. In some embodiments, the amino acid modification is an insertion of an amino acid (e.g., Gln). In some embodiments, the amino acid modification is an amino acid deletion.

In some embodiments, the conjugation efficiency of the engineered Fc-containing polypeptide conjugate comprising one or more amino acid modification (e.g., deletion, insertion, substitution, or mutation) in an another (e.g., accessible/reactive site other than carboxyl or amino terminus) site on the antibody (e.g., one or more heavy chain loops and/or light chain loops) of the Fc-containing polypeptide has an increased conjugation efficiency relative to the same engineered Fc-containing polypeptide conjugate without the amino acid modification at the same position. Examples of the accessible/reactive site on the antibody are listed in Tables 7, 8, and 9. In some embodiments, the conjugation efficiency increases by at least about 5% to about 99%. In some embodiments, the conjugation efficiency increases by about any of 5%, 10%, 15%, 25%, 30%, 35%, 40%, 45%, 50%, 55%, 60%, 65%, 70%, 75%, 80%, 85%, 90%, 95%, 96%, 97%, 98%, or 99%.

In some embodiments, the concentration ratio between the amine donor agent contacted and the engineered (Fc-containing polypeptide)-T molecule contacted is from about 2:1 to about 800:1. For example, the concentration ratio between the amine donor agent (e.g., a cytotoxic drug) and the engineered Fc-containing polypeptide attached to an acyl donor glutamine-containing tag loaded or used for the transglutaminase-catalyzed conjugation reaction can be about 20:1. In some embodiments, the concentration ratio between the amine donor agent contacted and the engineered (Fc-containing polypeptide)-T molecule contacted is about any of 2:1, 3:1, 4:1, 5:1, 6:1, 7:1, 8:1, 9:1, 10:1, 15:1, 20:1, 25:1, 30:1, 35:1, 40:1, 45:1, 50:1, 60:1, 70:1, 80:1, 90:1, 100:1, 200:1, 300:1, 400:1, 500:1, 600:1, 700:1, or 800:1.

In some embodiments, when an Fc-containing polypeptide (antibody) is conjugated with an amine donor agent via an acyl donor glutamine-containing tag or an endogenous glutamine (accessible/exposed/reactive) at a specific site (e.g., C-terminus), the antibody-drug-conjugate is more stable (e.g., longer in vivo half-life). Accordingly, in some embodiments, the engineered polypeptide conjugate as described herein (e.g., the engineered Fc-containing polypeptide conjugate, Fab-containing polypeptide, or toxin polypeptide conjugate) is present in a subject (e.g., a mammal) at least about 50% after at least about 1 day in vivo. For example, the engineered polypeptide conjugate is present in a subject at at least about any of 20%, 25%, 30%, 35%, 40%, 45%, 50%, 55%, 60%, 65%, 70%, 75%, 80%, 85%, 90%, or 95% after at least about any of 2 hours, 2-6 hours, 6-12 hours, 12-18 hours, 18-24 hours, 1 day, 2 days, 3 days, 4 days, 5 days, 6 days, 1 week, or 2 weeks in vivo. In some embodiments, the acyl donor glutamine-containing tag is LLQGG (SEQ ID NO:2) or LLQGA (SEQ ID NO:48) and the amine donor agent is aminocaproyl-VC-PABC-MMAD.

In another aspect, the invention provides a method for preparing an engineered Fc-containing polypeptide conjugate comprising the formula: (Fc-containing polypeptide)-T-A, wherein the Fc-containing polypeptide comprises a first Fc-containing polypeptide; wherein T is an acyl donor glutamine-containing tag engineered at a specific site or comprises an endogenous glutamine made reactive by the Fc-containing polypeptide engineering; wherein A is an amine donor agent; wherein the amine donor agent comprises a second Fc-containing polypeptide and a tag and does not comprise a reactive Gln; and wherein the acyl donor glutamine-containing tag or the endogenous glutamine is site-specifically crosslinked to the first Fc-containing polypeptide and the second Fc-containing polypeptide, comprising the steps of: a) providing an engineered (Fc-containing polypeptide)-T molecule comprising the first Fc-containing polypeptide attached to the acyl donor glutamine-containing tag; b) providing an engineered (Fc-containing polypeptide)-tag comprising the second Fc-containing polypeptide attached to the tag; c) contacting the engineered (Fc-containing polypeptide)-T molecule with the engineered (Fc-containing polypeptide)-tag molecule in reducing environment; and d) allowing the engineered (Fc-containing polypeptide)-T molecule to site-specifically and covalently react with the engineered (Fc-containing polypeptide)-tag molecule to form the Fc-containing polypeptide conjugate in the presence of a transglutaminase. In some embodiments, the acyl donor glutamine-containing tag is not spatially adjacent to a reactive Lys in the first Fc-containing polypeptide. In some embodiments, the acyl donor glutamine-containing tag comprises an amino acid sequence GSPLAQSHGG (SEQ ID NO:7) and the amine donor tag comprises an amino acid sequence GSGGKGG (SEQ ID NO:14).

In some embodiments, the crosslinking efficiency of the engineered (Fc-containing polypeptide)-T molecule to the engineered (Fc-containing polypeptide)-tag molecule is at least about 30%. In some embodiments, the crosslinking efficiency of the engineered (Fc-containing polypeptide)-T molecule to the engineered (Fc-containing polypeptide)-tag molecule is at least about any of 30%-35%, 35%-40%, 45%-50%, 50%-55%, 56%-60%, 61%-65%, 66%-70%, 71%-75%, 76%-80%, 81%-85%, 86%-90%, 91%-95%, or 96%-99%. In some embodiments, the crosslinking efficiency of the engineered (Fc-containing polypeptide)-T molecule to the engineered (Fc-containing polypeptide)-tag molecule is about any of 32%, 34%, 36%, 38%, 40%, 42%, 44%, 46%, 48%, 50%, 55%, 60%, 65%, 70%, 75%, 80%, 85%, 90%, 95%, or 99%.

In another aspect, the invention provides a method for preparing an engineered Fc-containing polypeptide conjugate comprising the formula: (Fc-containing polypeptide)-T-A, wherein the Fc-containing polypeptide comprises a first Fc-containing polypeptide; wherein T is an acyl donor glutamine-containing tag engineered at a specific site; wherein A is an amine donor agent; wherein the amine donor agent comprises a second Fc-containing polypeptide and does not comprise a reactive Gln; and wherein the acyl donor glutamine-containing tag is site-specifically crosslinked to the first Fc-containing polypeptide and the second Fc-containing polypeptide, comprising the steps of: a) providing an engineered (Fc-containing polypeptide)-T molecule comprising the first Fc-containing polypeptide located at the acyl donor glutamine-containing tag; b) providing the second Fc-containing polypeptide; c) contacting the engineered (Fc-containing polypeptide)-T molecule with the second Fc-containing polypeptide in reducing environment; and d) allowing the engineered (Fc-containing polypeptide)-T molecule to site-specifically and covalently link to the second Fc-containing polypeptide to form the Fc-containing polypeptide conjugate in the presence of a transglutaminase. In some embodiments, the acyl donor glutamine-containing tag is not spatially adjacent to a reactive Lys in the first Fc-containing polypeptide. In some embodiments, the acyl donor glutamine-containing tag comprises an amino acid sequence GSPLAQSHGG (SEQ ID NO:7) and the amine donor tag comprises an amino acid sequence GSGGKGG (SEQ ID NO:14). In some embodiments, the crosslinking efficiency of the engineered (Fc-containing polypeptide)-T molecule to the second Fc-containing polypeptide is at least about 30%. In some embodiments, the crosslinking efficiency of the engineered (Fc-containing polypeptide)-T molecule to the second Fc-containing polypeptide is at least about any of 30%-35%, 35%-40%, 45%-50%, 50%-55%, 56%-60%, 61%-65%, 66%-70%, 71%-75%, 76%-80%, 81%-85%, 86%-90%, 91%-95%, or 96%-99%. In some embodiments, the crosslinking efficiency of the engineered (Fc-containing polypeptide)-T molecule to the second Fc-containing polypeptide is about any of 32%, 34%, 36%, 38%, 40%, 42%, 44%, 46%, 48%, 50%, 55%, 60%, 65%, 70%, 75%, 80%, 85%, 90%, 95%, or 99%.

In another aspect, the invention provides a method for preparing an engineered Fc-containing polypeptide conjugate comprising the formula: (Fc-containing polypeptide)-T-A, wherein the Fc-containing polypeptide comprises a first Fc-containing polypeptide and a second Fc-containing polypeptide; wherein T is an acyl donor glutamine-containing tag comprising a first acyl donor glutamine-containing tag and a second acyl donor glutamine-containing tag crosslinked to the first Fc-containing polypeptide and the second Fc-containing polypeptide, respectively; wherein A is an amine donor agent; and wherein the first and the second acyl donor glutamine-containing tags are site-specifically crosslinked to each other, comprising the steps of: a) providing a first engineered (Fc-containing polypeptide)-T molecule comprising the first Fc-containing polypeptide located at the first acyl donor glutamine-containing tag; b) providing a second engineered (Fc-containing polypeptide)-T molecule comprising the second Fc-containing polypeptide located at the second acyl donor glutamine-containing tag; c) contacting the first engineered (Fc-containing polypeptide)-T molecule with the second engineered (Fc-containing polypeptide)-T molecule and the amine donor agent in reducing environment; and d) allowing the first engineered (Fc-containing polypeptide)-T molecule to site-specifically and covalently link to the second engineered (Fc-containing polypeptide)-T molecule to form the engineered Fc-containing polypeptide conjugate in the presence of a transglutaminase. In some embodiments, the first acyl donor glutamine-containing tag and the second acyl donor glutamine-containing tag are not spatially adjacent to a reactive Lys in the first Fc-containing polypeptide and the second Fc-containing polypeptide, respectively.

In some embodiments, the crosslinking efficiency of the first engineered (Fc-containing polypeptide)-T molecule to the second engineered (Fc-containing polypeptide)-T molecule is at least about 50%. In some embodiments, the crosslinking efficiency of the first engineered (Fc-containing polypeptide)-T molecule to the second engineered (Fc-containing polypeptide)-T molecule is at least about any of 30%-35%, 35%-40%, 45%-50%, 50%-55%, 56%-60%, 61%-65%, 66%-70%, 71%-75%, 76%-80%, 81%-85%, 86%-90%, 91%-95%, or 96%-99%. In some embodiments, the crosslinking efficiency of the first engineered (Fc-containing polypeptide)-T molecule to the second engineered (Fc-containing polypeptide)-T molecule is about any of 32%, 34%, 36%, 38%, 40%, 42%, 44%, 46%, 48%, 50%, 55%, 60%, 65%, 70%, 75%, 80%, 85%, 90%, 95%, or 99%.

In another aspect, the invention provides a method for preparing an engineered Fc-containing polypeptide conjugate comprising the formula: An engineered Fc-containing polypeptide conjugate comprising the formula: (Fc-containing polypeptide)-T-A, wherein the Fc-containing polypeptide comprises a first Fc-containing polypeptide and a second Fc-containing polypeptide; wherein T is an acyl donor glutamine-containing tag crosslinked to the first Fc-containing polypeptide; wherein A is an amine donor agent; and wherein the acyl donor glutamine-containing tag is site-specifically crosslinked to the second Fc-containing polypeptide, comprising the steps of: a) providing an engineered (Fc-containing polypeptide)-T molecule comprising the first Fc-containing polypeptide located at the first acyl donor glutamine-containing tag; b) providing the second Fc-containing polypeptide; c) contacting the engineered (Fc-containing polypeptide)-T molecule with the second Fc-containing polypeptide and the amine donor agent in reducing environment; and d) allowing the engineered (Fc-containing polypeptide)-T molecule to site-specifically and covalently link to the second Fc-containing polypeptide to form the engineered Fc-containing polypeptide conjugate in the presence of a transglutaminase. In some embodiments, the acyl donor glutamine-containing tag is not adjacent to a reactive Lys in the first Fc-containing polypeptide. In some embodiments, the crosslinking efficiency of the engineered (Fc-containing polypeptide)-T molecule to the second Fc-containing polypeptide is at least about 30%. In some embodiments, the crosslinking efficiency of the engineered (Fc-containing polypeptide)-T molecule to the second Fc-containing polypeptide is at least about any of 30%-35%, 35%-40%, 45%-50%, 50%-55%, 56%-60%, 61%-65%, 66%-70%, 71%-75%, 76%-80%, 81%-85%, 86%-90%, 91%-95%, or 96%-99%. In some embodiments, the crosslinking efficiency of the engineered (Fc-containing polypeptide)-T molecule to the second Fc-containing polypeptide is about any of 32%, 34%, 36%, 38%, 40%, 42%, 44%, 46%, 48%, 50%, 55%, 60%, 65%, 70%, 75%, 80%, 85%, 90%, 95%, or 99%.

In another aspect, the invention provides a method for preparing an engineered Fab-containing polypeptide conjugate comprising the formula: (Fab-containing polypeptide)-T-A, wherein T is an acyl donor glutamine-containing tag engineered at a specific site or comprises an endogenous glutamine made reactive by the Fab-containing polypeptide engineering; wherein A is an amine donor agent; wherein the amine donor agent is a biocompatible polymer comprising a reactive amine, and wherein the biocompatible polymer is site-specifically conjugated to the acyl donor glutamine-containing tag or the endogenous glutamine at a carboxyl terminus, an amino terminus, or elsewhere at an another site in the Fab-containing polypeptide, comprising the steps of: a) providing an engineered (Fab-containing polypeptide)-T molecule comprising the Fab-containing polypeptide located at the acyl donor glutamine-containing tag; b) contacting the biocompatible polymer with the engineered (Fab-containing polypeptide)-T molecule in the presence of a transglutaminase; and c) allowing the engineered (Fab-containing polypeptide)-T to covalently link to the biocompatible polymer to form the engineered Fab-containing polypeptide conjugate.

In some embodiments, the engineered Fab-containing polypeptide conjugate prepared using the methods described herein has conjugation efficiency of at least about 51%. In some embodiments, the engineered Fab-containing polypeptide conjugate has conjugation efficiency of at least about any of 51%-60%, 61%-70%, 71%-80%, 81%-90%, or 91%-100%. In some embodiments, the engineered Fab-containing polypeptide conjugate has conjugation efficiency of about any of 55%, 60%, 65%, 70%, 75%, 80%, 85%, 90%, 95%, or 100%.

In another aspect, the invention provides a method for preparing an engineered toxin polypeptide conjugate comprising the formula: (toxin polypeptide)-T-A, wherein T is an acyl donor glutamine-containing tag engineered at a specific site or comprises an endogenous glutamine made reactive by the toxin polypeptide engineering; wherein A is an amine donor agent; wherein the amine donor agent is a biocompatible polymer comprising a reactive amine, and wherein the biocompatible polymer is site-specifically conjugated to the acyl donor glutamine-containing tag or the endogenous glutamine at a carboxyl terminus, an amino terminus, or elsewhere at an another site in the toxin polypeptide, comprising the steps of: a) providing an engineered (toxin polypeptide)-T molecule comprising the toxin polypeptide located at the acyl donor glutamine-containing tag or the endogenous glutamine; b) contacting the biocompatible polymer with the engineered (toxin polypeptide)-T molecule in the presence of a transglutaminase; and c) allowing the engineered (toxin polypeptide)-T to covalently link to the biocompatible polymer to form the engineered toxin polypeptide conjugate.

In another aspect, the invention provides a method for preparing an engineered toxin polypeptide conjugate comprising the formula: (toxin polypeptide)-T-B, wherein T is an acyl donor glutamine-containing tag engineered at a specific site; wherein B is a biocompatible polymer, and wherein the toxin polypeptide is site-specifically conjugated to the acyl donor glutamine-containing tag at any site in the biocompatible polymer, comprising the steps of: a) providing an engineered T-B molecule comprising the acyl donor glutamine-containing tag located at the biocompatible polymer; b) contacting the toxin polypeptide with the engineered T-B molecule in the presence of a transglutaminase; and c) allowing the engineered T-B molecule to covalently react with the toxin polypeptide to form the engineered toxin polypeptide conjugate.

In some embodiments, the engineered toxin polypeptide conjugate prepared using the methods described herein has conjugation efficiency of at least about 51%. In some embodiments, the engineered toxin polypeptide conjugate has conjugation efficiency of at least about any of 51%-60%, 61%-70%, 71%-80%, 81%-90%, or 91%-100%. In some embodiments, the engineered toxin polypeptide conjugate has conjugation efficiency of about any of 55%, 60%, 65%, 70%, 75%, 80%, 85%, 90%, 95%, or 100%.

In some embodiments, the methods provided herein further comprise a purification step. The engineered Fc-containing polypeptide conjugates, engineered Fab-containing polypeptide conjugates, or the toxin polypeptide conjugates described herein can be purified using various purification methods, such as, e.g., hydroxylapatite chromatography; dialysis; affinity chromatography; hydrophobic interaction chromatography (HIC) (e.g, fractionation on a HIC); ammonium sulphate precipitation; polyethylene glycol or polyethylene glycol derivative precipitation, anion or cation exchange chromatography; reverse phase HPLC; chromatography on silica; chromatofocusing; SDS-PAGE, gel filtration, size exclusion chromatography, and weak partitioning chromatography.

In some embodiments, at least one purification step comprises a step of affinity chromatography method. Protein A ligand (synthetic, recombinant, or native) may be used to affinity purify the engineered Fc-containing polypeptide conjugates described herein. Synthetic or recombinant Protein A ligand may be purchased commercially from GE Healthcare (Piscataway, N.J.), Pierce (Rockford, Ill.), Sigma-Aldrich (St. Louis, Mo.), or Applied Biosystems (Foster City, Calif.), and native Protein A ligand (e.g., MABSELECT™, PROSEP™ Va, and PROSEP™ Ultra Plus) may be purchased commercially from GE Healthcare (Piscataway, N.J.) or Millipore (Billerica, Mass.).

In some embodiments, the purified engineered Fc-containing polypeptide conjugate, the purified engineered Fab-containing polypeptide conjugate, or the purified toxin polypeptide conjugates resulting from the purification step is highly pure, i.e., at least about any of 70%-75%, 75%-80%, 80%-85%, 85%-90%, 90%-95%, 95%-98%, or 99% pure. For example, the purified engineered polypeptide conjugate is about any of 80%, 85%, 90%, 91%, 92%, 93%, 94%, 95%, 96%, 97%, 98%, or 99% pure.

Pharmaceutical Compositions

The present invention also provides a pharmaceutical composition comprising the engineered polypeptide conjugates as described herein (e.g., the engineered Fc-containing polypeptide conjugate, engineered Fab-containing polypeptide conjugate, or engineered toxin polypeptide conjugates) in a pharmaceutically acceptable excipient or carrier. The engineered polypeptide conjugates can be administered alone or in combination with one or more other engineered polypeptide conjugates of the invention or in combination with one or more other drugs (or as any combination thereof). The pharmaceutical compositions, methods and uses of the invention thus also encompass embodiments of combinations (co-administration) with other active agents, as detailed below.

As used herein, the term "co-administration," "co-administered," or "in combination with" is intended to mean and does refer to the following: (i) simultaneous administration of a combination of an engineered polypeptide conjugate disclosed herein and therapeutic agent(s) to a patient in need of treatment, when such components are formulated together into a single dosage form which releases said components at substantially the same time to said patient; (ii) substantially simultaneous administration of such combination of an engineered polypeptide conjugate disclosed herein and therapeutic agent(s) to a patient in need of treatment, when such components are formulated apart from each other into separate dosage forms which are taken at substantially the same time by said patient, whereupon said components are released at substantially the same time to said patient; (iii) sequential administration of such combination of an engineered polypeptide conjugate disclosed herein and therapeutic agent(s) to a patient in need of treatment, when such components are formulated apart from each other into separate dosage forms which are taken at consecutive times by said patient with a significant time interval between each administration, whereupon said components are released at substantially different times to said patient; and (iv) sequential administration of such combination of an engineered polypeptide conjugate disclosed herein and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route Generally, the engineered polypeptide conjugates disclosed herein (e.g., the engineered Fc-containing polypeptide conjugate, engineered Fab-containing polypeptide conjugate, or engineered toxin polypeptide conjugates) are suitable to be administered as a formulation in association with one or more pharmaceutically acceptable excipient(s). The term 'excipient' is used herein to describe any ingredient other than the compound(s) of the invention. The choice of excipient(s) to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In some embodiments, isotonic agents, including, but not limited to, sugars, polyalcohols (e.g., mannitol, sorbitol) or sodium chloride are included in the pharmaceutical composition. Additional examples of pharmaceutically acceptable substances include, but are not limited to, wetting agents or minor amounts of auxiliary substances such as wetting or emulsifying agents, preservatives or buffers, which enhance the shelf life or effectiveness of the antibody.

In some embodiments, the engineered polypeptide conjugates described herein (e.g., the engineered Fc-containing polypeptide conjugate, engineered Fab-containing polypeptide conjugate, or engineered toxin polypeptide conjugates) can be deimmunized to reduce immunogenicity upon administration to a subject suing known techniques such as those described, e.g., in PCT Publication WO98/52976 and WO00/34317.

Pharmaceutical compositions of the present invention and methods for their preparation are readily apparent to those skilled in the art. Such compositions and methods for their preparation may be found, for example, in Remington's Pharmaceutical Sciences, 21st Edition (Mack Publishing Company, 2005). Pharmaceutical compositions are preferably manufactured under GMP conditions.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. Any method for administering peptides, proteins or antibodies accepted in the art may suitably be employed for the engineered Fc-containing polypeptide conjugates disclosed herein The pharmaceutical compositions of the invention are typically suitable for parenteral administration. Parenteral administration of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. For example, parenteral administration includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. In some embodiments, parenteral administration is the intravenous or the subcutaneous route.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include controlled, delayed, sustained, pulsed, targeted and programmed release formulations. For example, in one aspect, sterile injectable solutions can be prepared by incorporating the engineered Fc-containing polypeptide, e.g., antibody-drug conjugate or bispecific antibody, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An exemplary, non-limiting pharmaceutical composition of the invention is a formulation as a sterile aqueous solution having a pH that ranges from about 5.0 to about 6.5 and comprising from about 1 mg/mL to about 200 mg/mL of an engineered polypeptide conjugate disclosed herein, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dehydrate.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the agent moiety (e.g., small molecules such as cytotoxic agent) and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

For administration to human subjects, the total monthly dose of an engineered polypeptide conjugate disclosed herein (e.g., the engineered Fc-containing polypeptide conjugate, engineered Fab-containing polypeptide conjugate, or engineered toxin polypeptide conjugates) is typically in the range of about 0.01 mg to about 1200 mg per patient, depending, of course, on the mode of administration. For example, an intravenous monthly dose may require about 1 to about 1000 mg/patient. The total monthly dose may be administered in single or divided doses and may, at the physician's discretion, fall outside of the typical range given herein.

An exemplary, non-limiting range for a therapeutically or prophylactically effective amount of an engineered polypeptide conjugate, e.g., an Fc-containing polypeptide conjugate, Fab-containing polypeptide conjugate, or toxin polypeptide conjugate, disclosed herein is about 0.01 to about 1000 mg/patient/month. In certain embodiments, the engineered Fc-containing polypeptide conjugate may be administered at about 1 to about 200 or about 1 to about 150 mg/patient/month. In some embodiments, the patient is human.

Kits

The invention also provides kits (or articles of manufacture) for use in the treatment of the disorders described above. Kits of the invention include one or more containers comprising a purified engineered polypeptide conjugate (e.g., the engineered Fc-containing polypeptide conjugate, engineered Fab-containing polypeptide conjugate, or engineered toxin polypeptide conjugates) and instructions for using the conjugate for treating a disease. For example, the instructions comprise a description of administration of the engineered polypeptide conjugate to treat a disease, such as cancer (e.g., pancreatic, ovarian, colon, breast, prostate, or lung cancer). The kit may further comprise a description of selecting an individual suitable for treatment based on identifying whether that individual has the disease and the stage of the disease.

The instructions relating to the use of the engineered polypeptide conjugate generally include information as to dosage, dosing schedule, and route of administration for the intended treatment. The containers may be unit doses, bulk packages (e.g., multi-dose packages) or subunit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an engineered polypeptide as described herein. The container may further comprise a second pharmaceutically active agent.

Kits may optionally provide additional components such as buffers and interpretive information. Normally, the kit comprises a container and a label or package insert(s) on or associated with the container.

EXAMPLES

It is understood that the examples and embodiments described herein are for illustrative purposes only and that various modifications or changes in light thereof will be suggested to persons skilled in the art and are to be included within the spirit and purview of this application.

Example 1

Site-Specific Antibody-Drug Conjugation Using a Transglutaminase

Antibody conjugation to a desired payload (drug or agent moiety) was achieved via microbial transglutaminase-catalyzed transamidation reaction between an antibody carrying a glutamine tag (Q-tag) at the carboxyl terminus of the heavy and/or light chains and an amine-containing derivative of the payload (imaging agent or cytotoxin) of choice.

Antibody-Drug Conjugation

In this transamidation reaction, the glutamine on the antibody acted as an acyl donor, and the amine-containing compound acted as an acyl acceptor (amine donor). Purified antibody in the concentration of 1.67-4.04 µM was incubated with a 20-100 M excess acyl acceptor, ranging between 167-404 µM, in the presence of 0.225-0.545% (w/v) Streptoverticillium mobaraense transglutaminase (ACTIVA™, Ajinomoto, Japan) in 150-900 mM NaCl, and 25 mM MES, HEPES [4-(2-hydroxyethyl)-1-piperazineethanesulfonic acid] or Tris HCl buffer at pH range 6.2-8.8. The reaction conditions were adjusted for individual acyl acceptor derivatives, and the optimal efficiency and specificity were typically observed for 2.87 µM antibody, 287 µM derivative, and 0.378% (w/v) transglutaminase in 150 mM NaCl, 25 mM Tris HCl, pH 8.8. Following incubation at room temperature for 2.5 hours, the antibody was purified on MabSelect resin (GE Healthcare, Waukesha, Wis.) using standard affinity chromatography methods known to persons skilled in the art, such as commercial affinity chromatography from GE Healthcare. The conjugation efficiency was determined for antibody-fluorophore conjugates using relative UV-vis absorbance by the fluorophore and the antibody at their respective wavelengths, and for antibody-drug conjugates using hydrophobic interaction chromatographic analysis.

Hydrophobic Interaction Chromatography

The relative distribution of conjugation products with different drug:antibody stoichiometries was determined using hydrophobic interaction chromatography (HIC). Antibody-drug conjugates with zero, one or two drugs per antibody were readily resolved based on their differential retention on the HIC column due to the high hydrophobicity of the cytotoxin moieties. Conjugation products were injected onto a TSKgel Butyl-NPR column, 2.5 µm particle size, 4.6 mm×10 cm (Tosoh Bioscience, Japan) in Buffer A (1.5 M ammonium sulfate, 50 mM sodium phosphate, pH 7), and eluted with a linear gradient from 0 to 100% Buffer B (50 mM sodium phosphate, pH 7) over 85 min at 0.8 mL/min. An Agilent 1100 series chromatography system and Chemstation software (Agilent Technologies, Santa Clara, Calif.) were used to separate, quantify and fractionate the conjugates.

Antibody-Fluorophore Conjugation Efficiencies

Figure 2A:
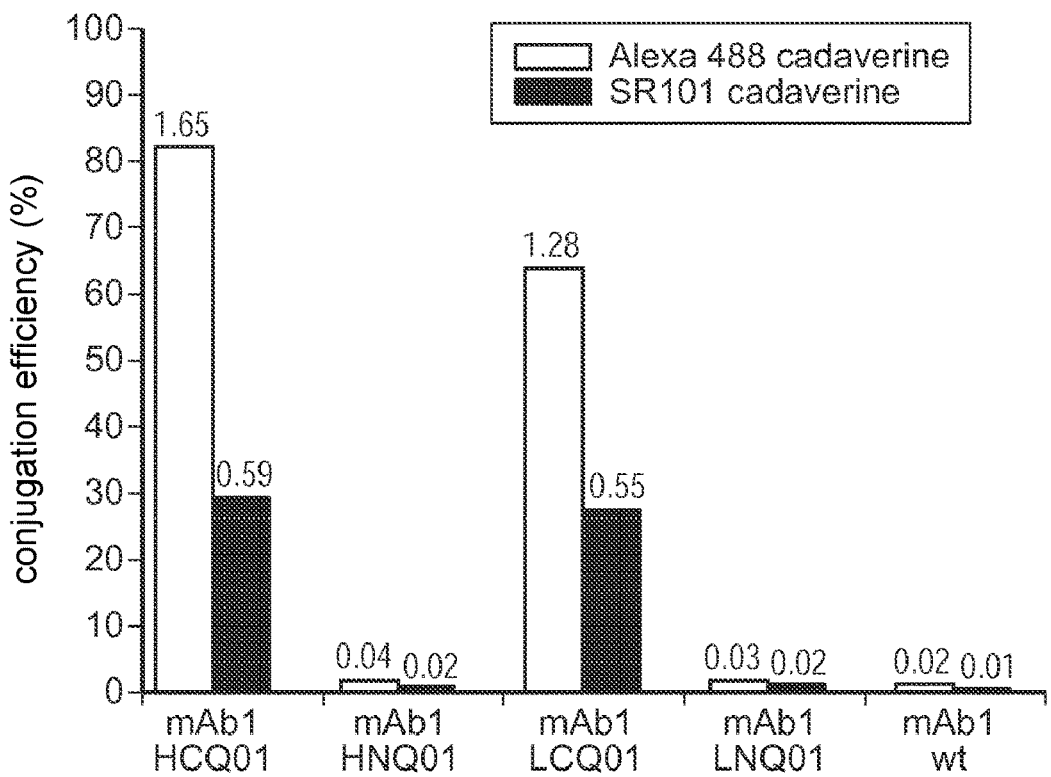
FIG. 2A and FIG. 2B show the efficiencies of transglutaminase-catalyzed conjugation of two fluorophore cadaverines to mAb1 (IgG1 subtype) carrying a Q-(glutamine) tag at the heavy chain carboxyl or amino termini (HCQ01 (SEQ ID NO:2) and HNQ01 (QVQLKE (SEQ ID NO:39)), respectively) or the light chain carboxyl or amino termini (LCQ01 (GGGLLQGG (SEQ ID NO: 5)) and LNQ01 (GLLQG (SEQ ID NO:6), respectively), and to untagged mAb1 at 150 mM NaCl, 25 mM HEPES, and pH 8.0 (A) or at 150 mM NaCl, 25 mM HEPES, and pH 8.8 (B). The efficiency values for purified conjugates were calculated from the relative UV-vis absorbance at the excitation wavelength of each fluorophore and at 280 nm. The corresponding fluorophore/antibody loading is indicated above each bar.
Figure 2B:
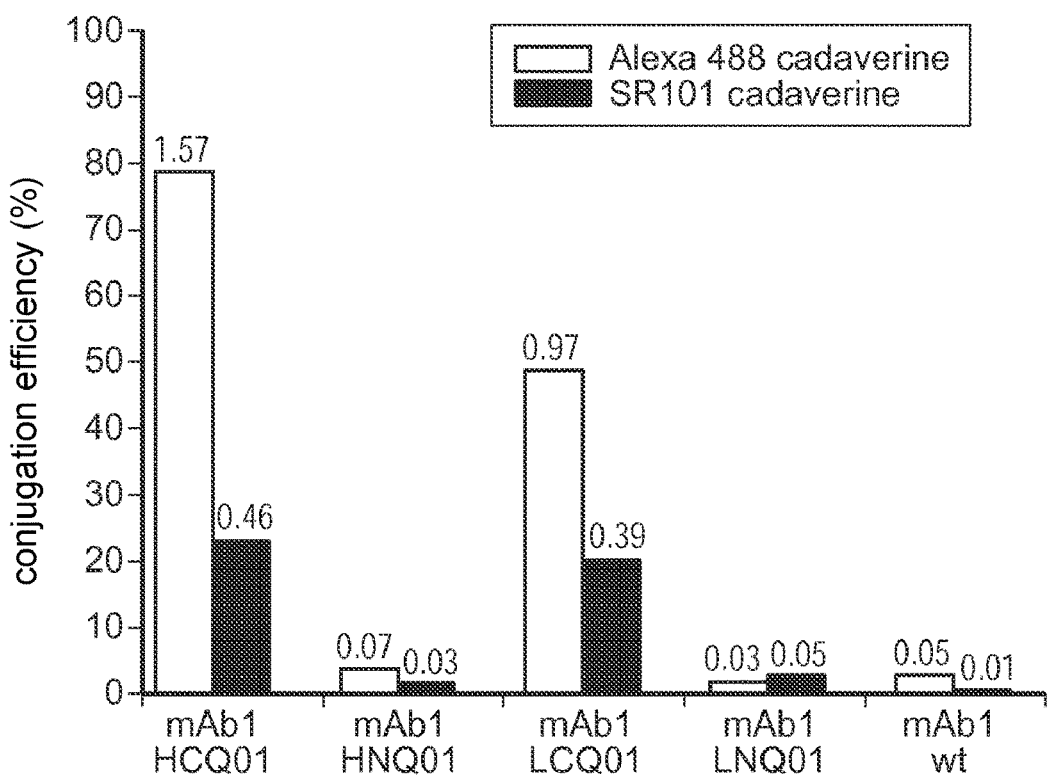
Figure 3:
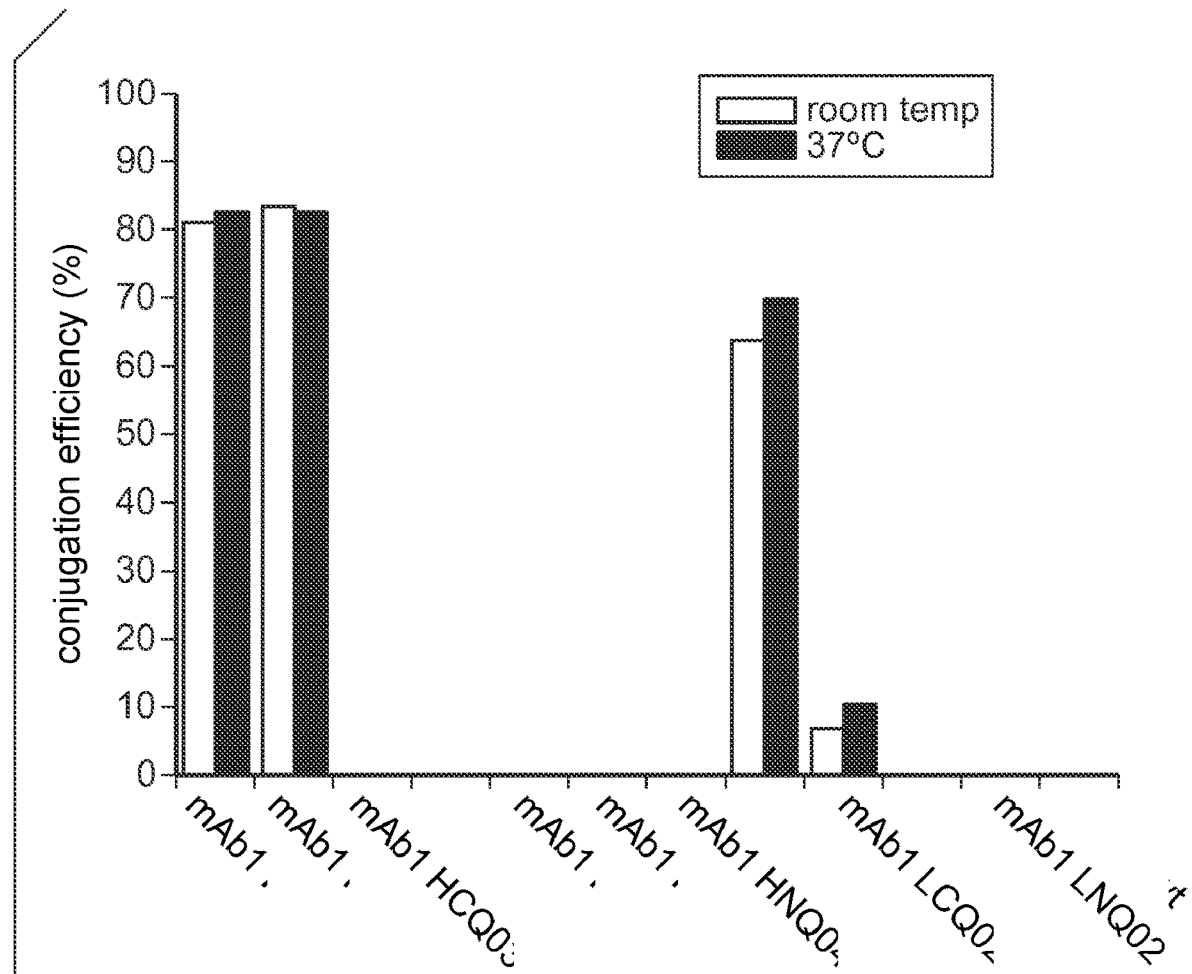
FIG. 3 shows the efficiencies of transglutaminase-catalyzed conjugation of Alexa 488 cadaverine to IgG1 mAb1 carrying various Q-tags incorporated at either termini of the heavy or light chain, as indicated, and to the wild type mAb1 without any tags. The efficiency values for purified conjugates were calculated from the relative UV-vis absorbance at 495 nm (the excitation wavelength of Alexa 488) and at 280 nm. The amino acid sequences of all the Q-tags and the portions of the monoclonal antibodies are shown below. The symbol "–" indicates deletion of an amino acid sequence. For example, in HCQ01, LSLSPG is a portion of the monoclonal antibody sequence with the last amino acid deleted, and the Q-tag LLQGG is engineered to the monoclonal antibody.
Figure 4:
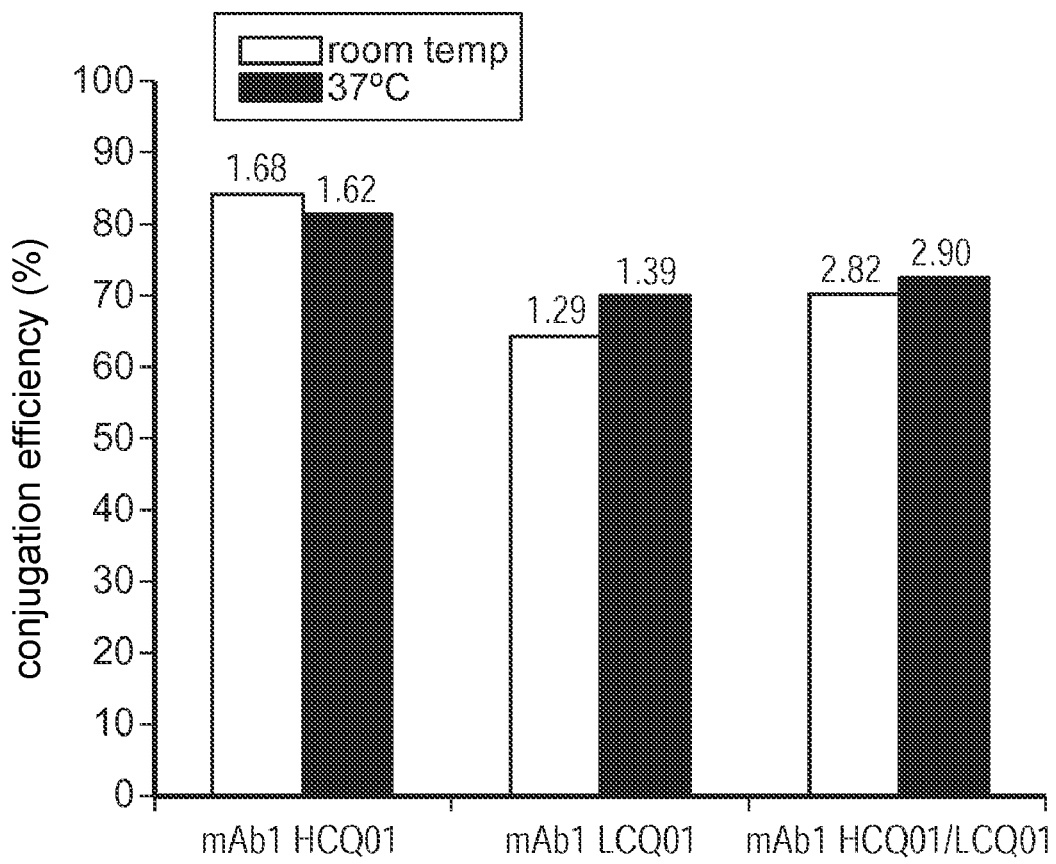
FIG. 4 shows the efficiencies of transglutaminase-catalyzed conjugation of Alexa 488 cadaverine to IgG1 mAb1-HCQ01 carrying the HCQ01 tag at the carboxyl terminus of the heavy chain, mAb1-LCQ01 with the LCQ01 tag at the C terminus of the light chain, and double mutant carrying both the HCQ01 and LCQ01 tags. The efficiency values for purified conjugates were calculated from the relative UV-vis absorbance at 495 nm (the excitation wavelength of Alexa 488) and at 280 nm. The corresponding fluorophore/antibody loading is indicated above each bar.

The efficiencies of transglutaminase-catalyzed conjugation between mAb1-HCQ01 (IgG1 subtype) carrying a Q-containing tag (HCQ01 is LLQGG (SEQ ID NO:2)) at the carboxyl terminus of the heavy chain and various amine-containing fluorophore derivatives were tested. FIG. 1. The conjugation between mAb1-HCQ01 and fluorophore derivative Alexa 488 cadaverine had the highest conjugation efficiency at 79%. The efficiencies of transglutaminase-catalyzed conjugation were further tested using two fluorophore cadaverines (Alexa 488 cadaverine and SR101 cadaverine) carrying a Q-containing tag at the heavy chain carboxyl or amino termini (HCQ01) and HNQ01 (QVQLKE (SEQ ID NO:39)), respectively) or the light chain carboxyl or amino termini (LCQ01 (GGGLLQGG (SEQ ID NO:5)) and LNQ01 (GLLQG (SEQ ID NO:6), respectively) at two different conjugation conditions (150 mM NaCl, 25 mM HEPES, and pH 8.0; or 150 mM NaCl, 25 mM HEPES, and pH 8.8). Conjugation of the fluorophore cadaverine and the mAb1 was observed in mAb1 carrying a Q-tag at the heavy chain carboxyl and the light chain carboxyl termini. FIG. 2A and FIG. 2B. The efficiencies of transglutaminase-catalyzed conjugation of Alexa 488 cadaverine to IgG1 mAb1 carrying various Q-tags incorporated at either termini of the heavy or light chain and the wild type mAb1 without any tags were also tested. FIG. 3. Similar to FIG. 2A and FIG. 2B, conjugation of the Alexa 488 cadaverine to IgG1 mAb1 was observed in the carboxyl termini of the heavy and light chains. Finally, the efficiencies of transglutaminase-catalyzed conjugation of Alexa 488 cadaverine to IgG1 mAb1-HCQ01 carrying the HCQ01 tag at the carboxyl terminus of the heavy chain, mAb1-LCQ01 with the LCQ01 tag at the carboxyl terminus of the light chain, and double mutant carrying both the HCQ01 and LCQ01 tags were tested. In this example, the highest conjugation efficiency was observed in IgG1 mAb-HCQ01-Alexa 488 cadaverine. FIG. 4.

Analysis of Antibody-Drug Conjugation Efficiency Using Hydrophobic Interaction Chromatography Hydrophobic interaction chromatograms obtained for IgG1 mAb1-HCQ01 carrying the HCQ01 tag at the carboxyl terminus of the heavy chain were determined for the following for the drugs: prior to conjugation (A) and following conjugation to Aminocaproyl-MMAE (B), Amino-PEG2-Propionyl-MMAE (C), Amino-PEG3-Propionyl-MMAE (D), Ac-Lys-VC-PABC-MMAD (E), Aminocaproyl-MMAD (F), Ac-Lys-Gly-MMAD (G), Ac-Lys-β-Ala-MMAD (H), Aminocaproyl-VC-PABC-MMAF (I), Aminocaproyl-MMAF (J), Putrescinyl-Geldanamycin (K) and Ac-Lys-Putrescinyl-Geldanamycin (L). Conjugation was observed in (B)-(L). Hydrophobic interaction chromatograms obtained for mAb1-HNQ01 carrying the HNQ01 tag at the amino terminus of the heavy chain were also examined for the following drugs: prior to conjugation (A) and following conjugation to AcLys-Putrescinyl-Geldanamycin (B), mAb1-LCQ01 carrying the LCQ01 tag at the carboxyl terminus of the light chain: unconjugated (C) and conjugated to AcLys-Putrescinyl-Geldanamycin (D), and mAb1-LNQ01 with the LNQ01 (SEQ ID NO:9) tag at the N terminus of the light chain: prior to conjugation (E) and following conjugation to AcLys-Putrescinyl-Geldanamycin (F). Further, control experiment with hydrophobic interaction chromatograms obtained for the wild type IgG1 mAb1 without carrying any Q-tags was also conducted for the following drugs: prior to conjugation (A) and following conjugation with Aminocaproyl-VC-PABC-MMAF (B), Aminocaproyl-MMAF (C), Putrescinyl-Geldanamycin (D) and AcLys-Putrescinyl-Geldanamycin (E). No drugs were observed to conjugate to the antibody in the control experiment.

Antibody-Drug Conjugation Efficiencies and Stabilities

The relative distributions of antibody-drug conjugates with different stoichiometries were obtained by integrating hydrophobic interaction chromatograms. Loading is equivalent to the drug/antibody ratio.

TABLE 2

Antibody-drug conjugation efficiencies

| Antibody-drug conjugate | Relative distribution of conjugates (%) | | | Conjugation Efficiency (%) | Loading |
|---|---|---|---|---|---|
| | 0 drug/Ab | 1 drug/Ab | 2 drug/Ab | | |
| mAb1-HCQ01-Aminocaproyl-MMAE | 33.6 | 49.6 | 16.8 | 41.5 | 0.83 |
| mAb1-HCQ01-Amino-PEG2-Propionyl-MMAE | 2.6 | 29.5 | 67.9 | 82.5 | 1.65 |
| mAb1-HCQ01-Amino-PEG3-Propionyl-MMAE | 2.9 | 30.3 | 66.8 | 82.0 | 1.64 |
| mAb1-HCQ01-Aminocapropyl-VC-PABC-MMAE | 0.9 | 13.0 | 86.1 | 92.6 | 1.85 |
| mAb1-HCQ01-AcLys-VC-PABC-MMAD | 0.6 | 7.1 | 92.3 | 96.0 | 1.92 |
| mAb1-HCQ01-Aminocaproyl-MMAD | 10.1 | 44.3 | 45.6 | 67.5 | 1.35 |
| mAb1-HCQ01-AcLysGly-MMAD | — | 12.7 | 87.3 | 93.5 | 1.87 |
| mAb1-HCQ01-AcLys-β-Ala-MMAD | — | 4.8 | 95.2 | 97.5 | 1.95 |
| mAb1-HCQ01-Aminocaproyl-MMAF | 12.5 | 46.0 | 41.4 | 64.5 | 1.29 |
| mAb1-HCQ01-Aminocaproyl-VC-PABC-MMAF | — | 5.5 | 94.5 | 97.4 | 1.95 |
| mAb1-HCQ01-Putrescinyl-Geldanamycin | 83.1 | 14.0 | 2.9 | 10.0 | 0.20 |
| mAb1-HCQ01-AcLys-Putrescinyl-Geldanamycin | — | 14.3 | 85.7 | 93.0 | 1.86 |
| mAb1-HNQ01-AcLys-Putrescinyl-Geldanamycin | 100.0 | — | — | 0.0 | 0.00 |
| mAb1-LCQ01-AcLys-Putrescinyl-Geldanamycin | 26.6 | 43.3 | 30.1 | 51.5 | 1.03 |
| mAb1-LNQ01-AcLys-Putrescinyl-Geldanamycin | 100.0 | — | — | 0.0 | 0.00 |
| mAb1-wt-Aminocaproyl-VC-PABC-MMAE | 100.0 | — | — | 0.0 | 0.00 |
| mAb1-wt-Aminocaproyl-MMAF | 100.0 | — | — | 0.0 | 0.00 |
| mAb1-wt-Aminocaproyl-VC-PABC-MMAF | 100.0 | — | — | 0.0 | 0.00 |
| mAb1-wt-Putrescinyl-Geldanamycin | 100.0 | — | — | 0.0 | 0.00 |
| mAb1-wt-AcLys-Putrescinyl-Geldanamycin | 100.0 | — | — | 0.0 | 0.00 |

Transglutaminase-catalyzed conjugation of Ac-Lys-Putrescinyl-Geldanamycin to mAb1-HCQ01 was also monitored under varying initial drug per antibody concentration ratios. Conjugation products with different stoichiometries were analyzed using HIC.

TABLE 3

Conjugation Efficiency Using Lower Amounts of Drug Derivative Per Antibody

| [drug]:[antibody] | Relative distribution of conjugates (%) | | | Conjugation efficiency (%) | Loading |
|---|---|---|---|---|---|
| | 0 drug/Ab | 1 drug/Ab | 2 drug/Ab | | |
| 100:1 | 1.9 | 13.6 | 84.4 | 91.0 | 1.82 |
| 80:1 | 2.1 | 16.1 | 81.8 | 90.0 | 1.80 |
| 60:1 | 2.0 | 15.0 | 83.0 | 90.5 | 1.81 |
| 40:1 | 2.0 | 16.6 | 81.4 | 89.5 | 1.79 |
| 20:1 | 3.4 | 18.5 | 78.2 | 87.5 | 1.75 |

The stabilities of several antibody-drug conjugates were examined using HIC following incubation at 4° C. for 4 weeks, at 37° C. for 16 hours, and at 37° C. for 1 week.

TABLE 4

Antibody-Drug Conjugate Stabilities

| Antibody-drug conjugate | Relative distribution of conjugates (%) | | | Conjugation efficiency (%) | Loading |
|---|---|---|---|---|---|
| | 0 drug/Ab | 1 drug/Ab | 2 drug/Ab | | |
| mAb1-HCQ01-Aminocaproyl-MMAF | | | | | |
| freshly prepared | 23.6 | 52.6 | 23.8 | 50.0 | 1.00 |
| incubated at 4° C. for 4 weeks | 30.8 | 49.0 | 20.2 | 44.5 | 0.89 |

TABLE 4-continued

Antibody-Drug Conjugate Stabilities

| Antibody-drug conjugate | Relative distribution of conjugates (%) | | | Conjugation efficiency | |
|---|---|---|---|---|---|
| | 0 drug/Ab | 1 drug/Ab | 2 drug/Ab | (%) | Loading |
| incubated at 37° C. for 16 hours | 29.7 | 44.5 | 25.8 | 48.0 | 0.96 |
| incubated at 37° C. for 1 week | 32.2 | 46.2 | 21.6 | 44.5 | 0.89 |
| mAb1-HCQ01-Aminocaproyl-VC-PABC-MMAF | | | | | |
| freshly prepared | — | 15.3 | 84.7 | 92.5 | 1.85 |
| incubated at 4° C. for 4 weeks | — | 13.8 | 86.2 | 93.0 | 1.86 |
| incubated at 37° C. for 16 hours | — | 15.5 | 84.5 | 92.0 | 1.84 |
| incubated at 37° C. for 1 week | — | 16.6 | 83.4 | 91.5 | 1.83 |
| mAb1-HCQ01-Putrescinyl-Geldanamycin | | | | | |
| freshly prepared | 83.1 | 14.0 | 2.9 | 10.0 | 0.20 |
| incubated at 4° C. for 4 weeks | 83.8 | 12.7 | 3.5 | 10.0 | 0.20 |
| incubated at 37° C. for 16 hours | 85.7 | 11.4 | 2.9 | 8.5 | 0.17 |
| incubated at 37° C. for 1 week | 85.1 | 12.0 | 2.8 | 9.0 | 0.18 |
| mAb1-HCQ01-Ac-Lys-Putrescinyl-Geldanamycin | | | | | |
| freshly prepared | — | 14.3 | 85.7 | 93.0 | 1.86 |
| incubated at 4° C for 4 weeks | — | 12.8 | 87.2 | 93.5 | 1.87 |
| incubated at 37° C. for 16 hours | 1.3 | 13.3 | 85.5 | 92.0 | 1.84 |
| incubated at 37° C. for 1 week | — | 9.8 | 90.2 | 95.0 | 1.90 |

Table 5 shows percentage conjugation of different subtypes of IgG and dye.

| Isotype | Tag position | Tag | Dye | DAR | % conjugation |
|---|---|---|---|---|---|
| IgG1 | HC C-terminus | Q00 | cadaverine-Alexa350 | 1.29 | 64.5 |
| IgG1 | HC C-terminus | Q00 | cadaverine-Alexa647 | 0.11 | 5.5 |
| IgG2 | HC C-terminus | Q01 | cadaverine-Alexa488 | 1.62 | 81.0 |
| IgG2 | HC C-terminus | Q06 | cadaverine-Alexa488 | 1.48 | 74.0 |
| IgG2 | HC C-terminus | Q07 | cadaverine-Alexa488 | 1.67 | 83.5 |
| IgG2 | HC C-terminus | Q01 | cadaverine-Alexa647 | 0.57 | 28.3 |
| IgG2 | HC C-terminus | Q06 | cadaverine-Alexa647 | 0.51 | 25.3 |
| IgG2 | HC C-terminus | Q07 | cadaverine-Alexa647 | 0.75 | 37.5 |
| IgG4 | HC C-terminus | Q01 | cadaverine-Alexa350 | 1.76 | 88.0 |
| IgG4 | HC C-terminus | Q01 | cadaverine-Alexa488 | 1.65 | 82.5 |

Q00 is KGSPLAQSHGG (SEQ ID NO: 18);
Q01 is RGSPLAQSHGG (SEQ ID NO: 19);
Q06 is RLLQGG (SEQ ID NO: 15); and
Q07 is -LLQGG (SEQ ID NO: 25).
DAR indicates Drug to Antibody Ratio.

Mass Spectrometry Verification of Site-Specific Conjugation

Antibodies carrying Q-tag Q01 (GSPLAQSHGG (SEQ ID NO:7)) of IgG1, IgG2, and IgG4 isotypes were conjugated with transglutaminase and cadaverine Alexa-488. As control, antibody missing the glutamine in the introduced tag and an unrelated wild type IgG2 antibody were also conjugated under the same conditions as was done for the other three antibodies. All antibodies were digested into peptides and separated by reverse phase chromatography prior to mass spectrometry analysis. The digested peptides were monitored by absorbance at 490 nm (absorbance maximum of the Alexa488 dye). Two double peaks were identified in the Q-tag containing samples, whereas no labeling was identified in the control antibodies, strongly indicating site specific conjugation under given conditions. The two double peaks from the IgG1,2,4 Q01 samples were further analyzed by mass spectrometry to verify the site of attachment. All peptides that have Alexa488 conjugated were identified as the introduced Q01 tag. (The two peaks observed in using Alexa 488 were due to the fact that Alexa488 used in the experiments is a mixture of two species with the cadaverine linker is attached at the 5-, or 6-position. The double peak character of the tag peptide is a result of small amount of proteolysis at the C-terminus that happens during expression.) FIG. 8A-1, FIG. 8A-2, FIG. 8B-1, and FIG. 8B-2.

Example 2

Transglutaminase Catalyzed Crosslinking of Bispecific Antibodies Using Different K-tag and Q-tag Materials and Methods IgG heterodimers (i.e., bispecific antibodies) were prepared by incubation of the two antibodies (either wild type IgG4 or IgG1 and IgG2 bispecific mutants) in PBS (Phosphate Buffered Saline) with 1-2 mM GSH (Glutathione) for 24 hours at 37° C. The heterodimers were crosslinked by incubation of the formed bispecific antibody with microbial transglutaminase. In the transamidation reaction, the introduced glutamine on the antibody acts as an acyl donor, and either lysine on the antibody, the lysine containing tags, or diamine compounds act as an acyl acceptor. Typically, 1.67-4.04 µM purified antibody is incubated with a 0.1-1.0% (w/v) *Streptoverticillium mobaraense* transglutaminase (ACTIVA, Ajinomoto, Japan) in 150-900 mM NaCl, and 25 mM IVIES (2-[N-morpholine]ethamine sulfonic acid), HEPES or Tris HCl buffer at pH range 6.2-8.8. In the case of crosslinking of two glutamine tags by a diamine compound, 20 molar excess of acyl acceptor, ranging between 167-404 µM was used. Following incubation at room temperature for approximately 2 hours, the antibody is purified on MabSelect resin (GE Healthcare, Waukesha, Wis.) using standard affinity chromatography methods as known by persons skilled in the art. The crosslinking efficiency is determined by running the antibodies on reducing SDS gel, and comparing intensities of heavy chain band relative to heavy-heavy chain crosslinked band.

Transglutaminase Catalyzed Crosslinking of Bispecific Antibodies IgG4 and IgG2

Figure 5:
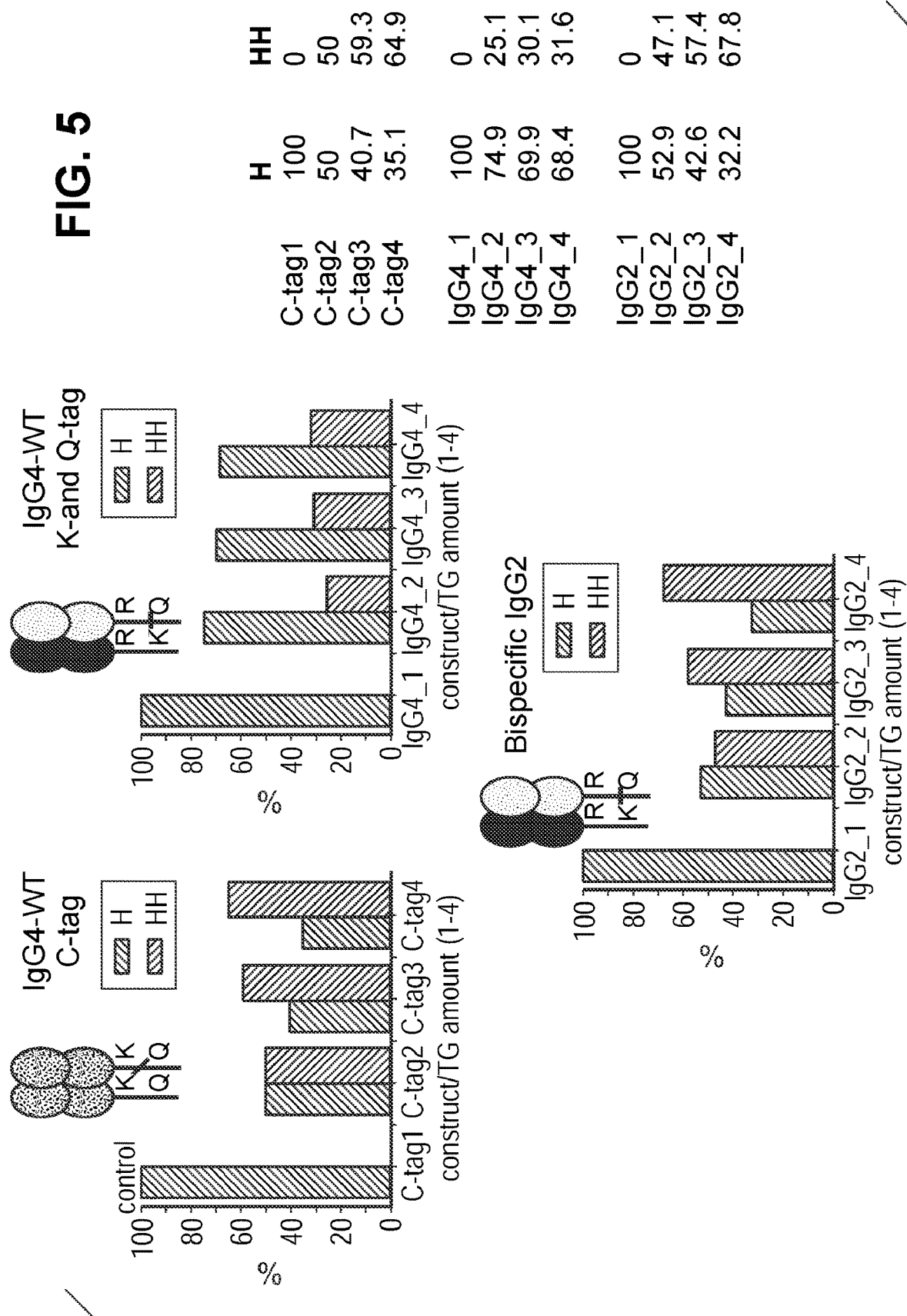
FIG. 5 shows transglutaminase catalyzed crosslinking of bispecific antibodies (IgG4 and IgG2). C-tags 1-4 correspond to GSPLAQSHGG ((SEQ ID NO:7)).

Control antibody carrying a C-terminal (carboxyl terminus) tag with introduced glutamine (Q00 tag: GSPLAQSHGG (SEQ ID NO:7)) was incubated with increasing amount of transglutaminase and then separated by SDS PAGE under reducing conditions. The bands corresponding to monomeric heavy chain, and crosslinked heavy-heavy chain were quantified showing approximately 60% of the IgG4 antibody crosslinks. Bispecific WT (Wild-Type) IgG4 and mutant IgG2 antibodies (one half carrying Q-tag and the other half carrying K-tag) were prepared as described in the method section, crosslinked by transglutaminase and analyzed as the control antibody described above. The data shows that, for WT-IgG4, approximately 30% of the antibodies were crosslinked, while the mutant IgG2 showed 67%. FIG. 5.

Figure 6:
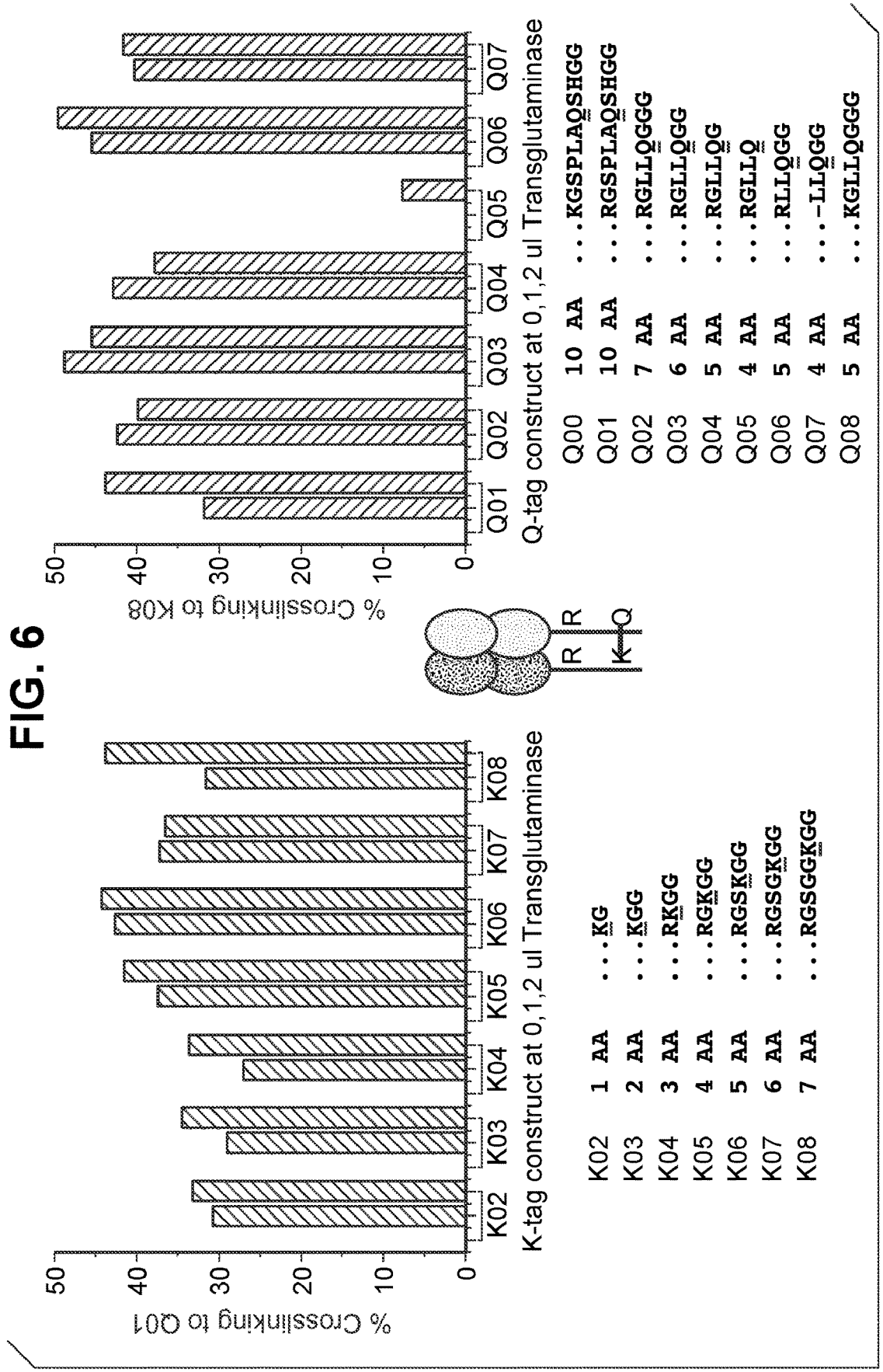
FIG. 6 shows crosslinking efficiency of different K-tags and Q-tags for bispecific antibody crosslinking at different concentrations of transglutaminase. K04, K05, K06, K07, and K08 correspond to SEQ ID NOs:26, 27, 28, 29, and 30, respectively. Q00, Q01, Q02, Q03, Q04, Q05, Q06, Q07, and Q08 correspond to SEQ ID NOs:31, 32, 33, 34, 35, 36, 37, 2, and 38, respectively.

Minimization and Crosslinking Efficiency of Different K-tags and Q-tags for Bispecific Antibodies Mutant IgG2 antibody with Q01 tag was incubated with mutant IgG2 antibodies carrying K02-K08 tags, and bispecific antibodies were formed as described above. The extent of crosslinking was measured using SDS PAGE. Mutant IgG2 antibody with K08 tag was incubated with mutant IgG2 antibodies carrying Q01-Q08 tags, and bispecific antibodies were formed as described above. The extent of crosslinking was measured using SDS PAGE. FIG. 6.

Figure 7:
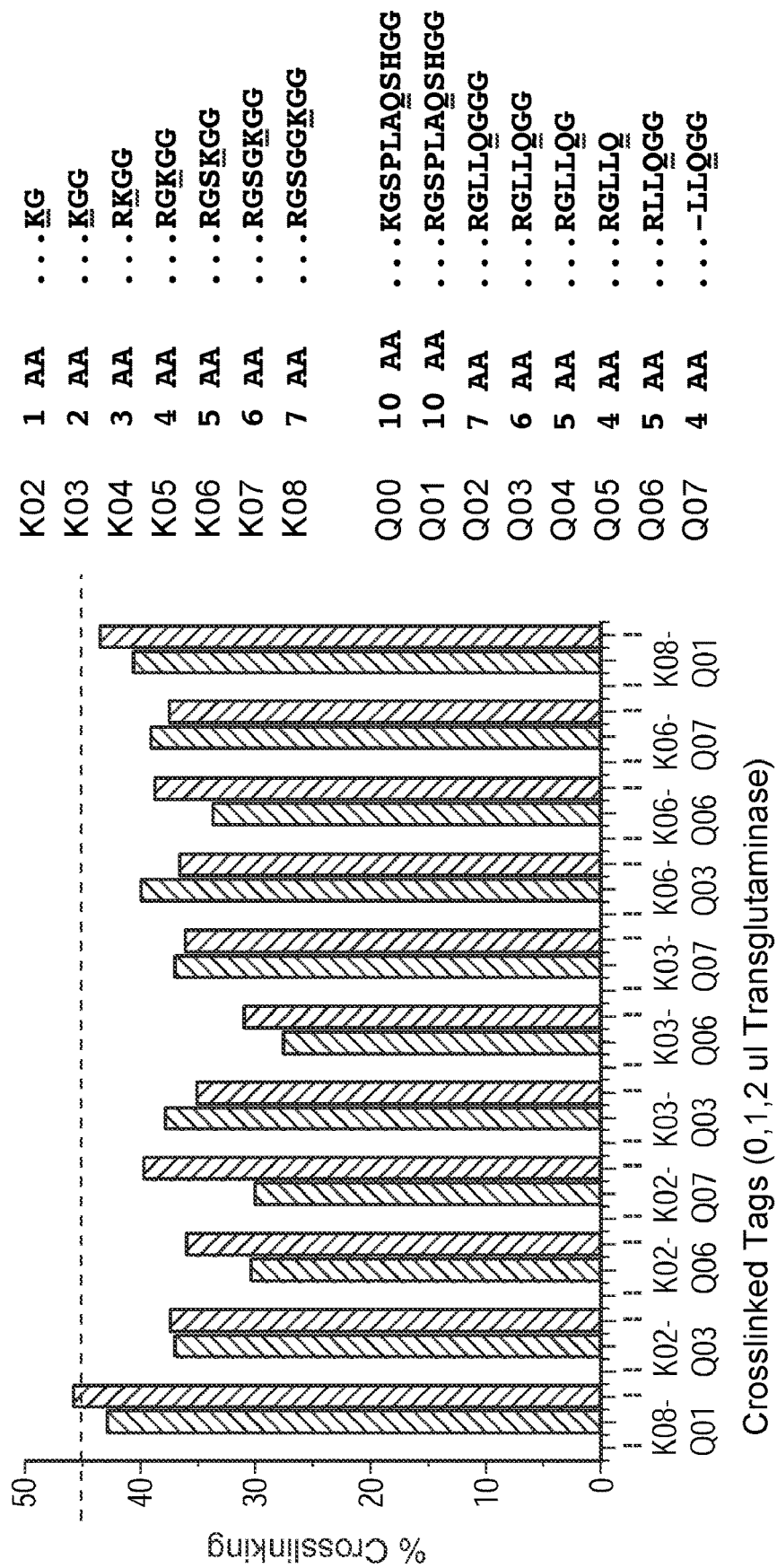
FIG. 7 shows crosslinking efficiency of different K-tags and Q-tags for bispecific antibody crosslinking at different concentrations of transglutaminase. K04, K05, K06, K07, and K08 correspond to SEQ ID NOs:26, 27, 28, 29, and 30, respectively. Q00, Q01, Q02, Q03, Q04, Q05, Q06, and Q07 correspond to SEQ ID NOs:31, 32, 33, 34, 35, 36, 37, and 2, respectively.
Figures 1, 8A:
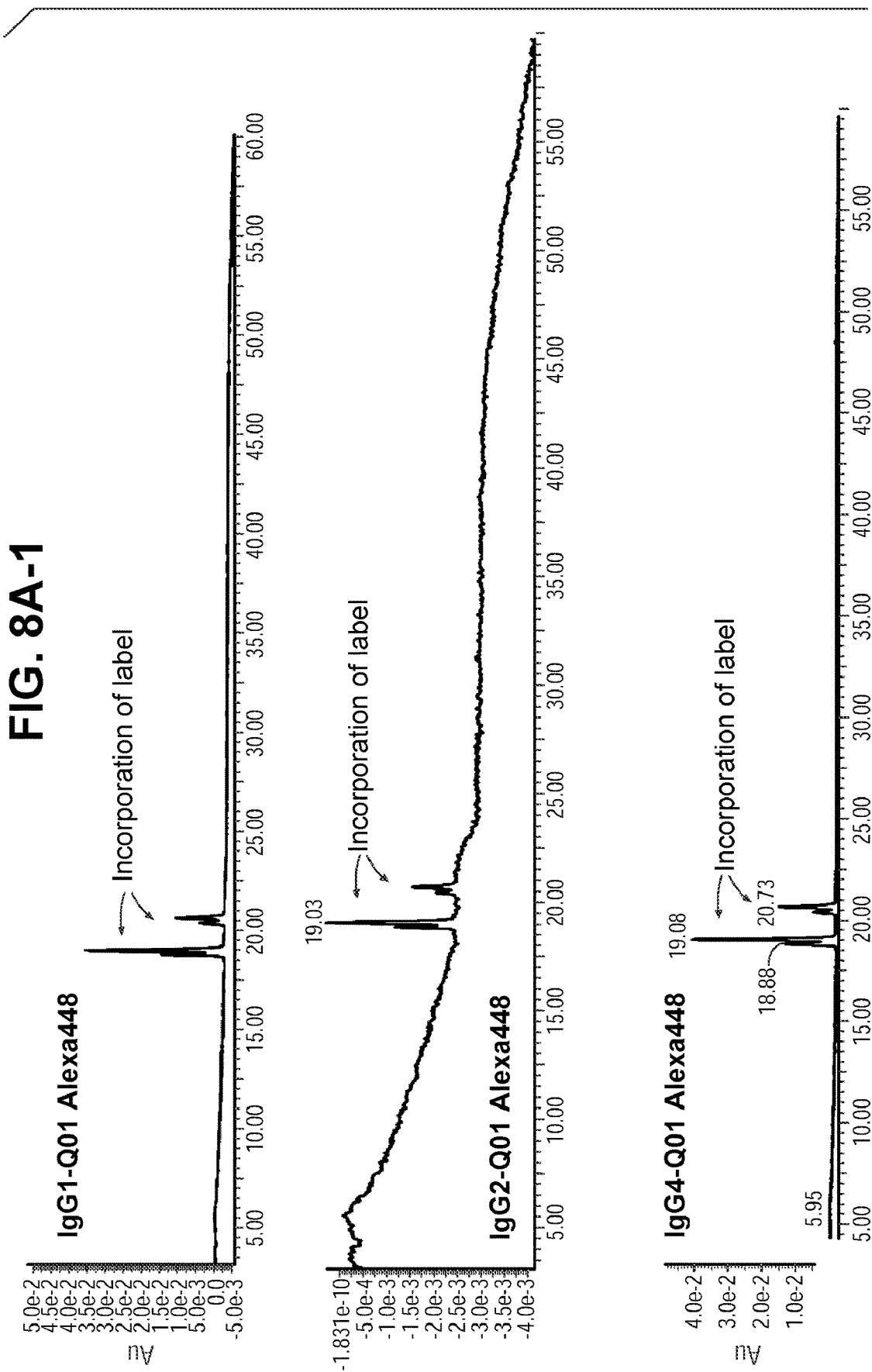
Figures 2, 8B:
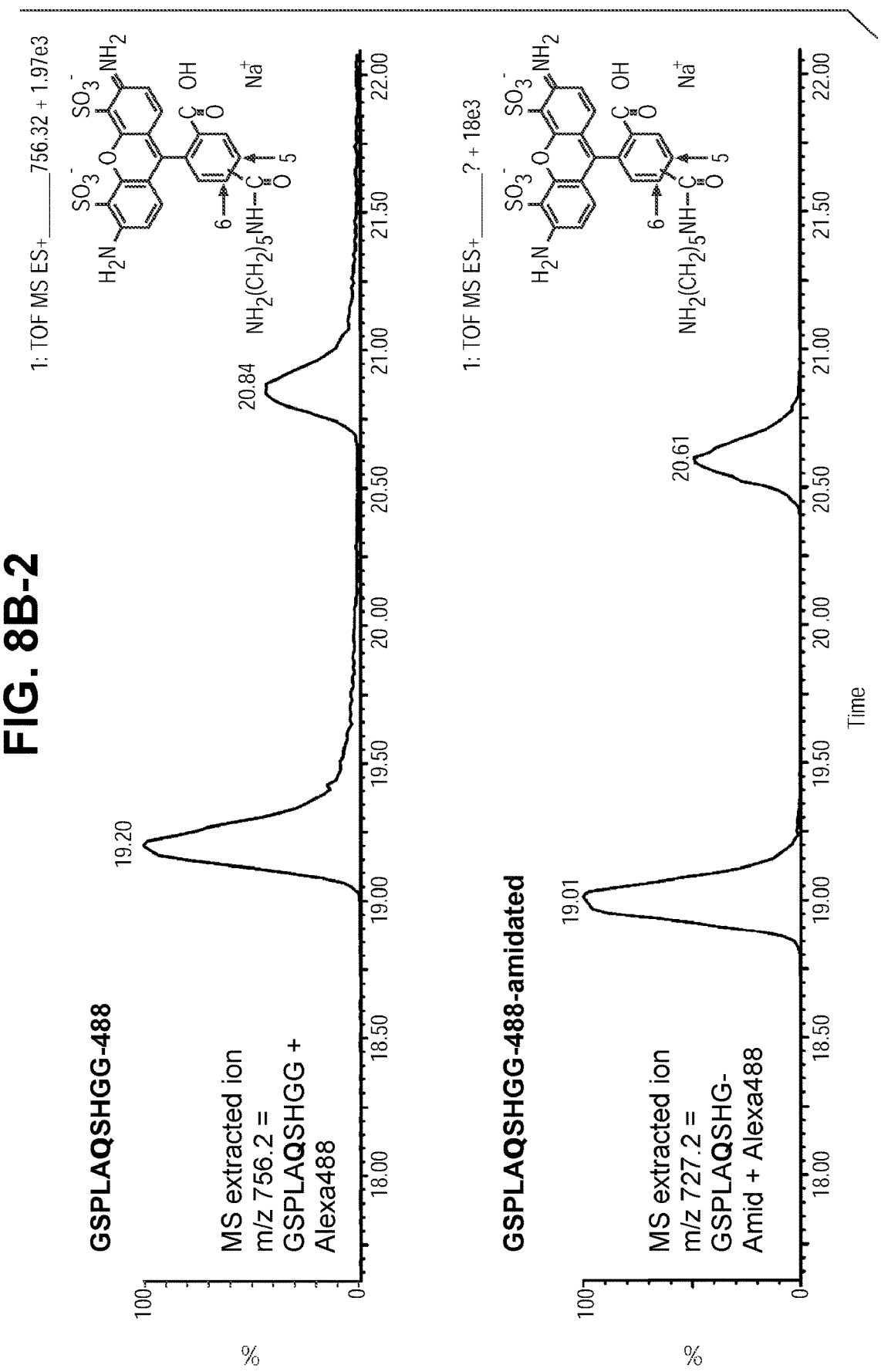

Mutant IgG2 antibodies with Q03, Q06, and Q07 tags were incubated with mutant IgG2 antibodies carrying K02, K03, and K06 tags, and bispecific antibodies were formed as described above. The extent of crosslinking was measured from SDS PAGE. FIG. 7.

Example 3

In Vitro Cytotoxicity Assays

In vitro cytotoxicity assays were carried out using various antibodies, payloads (i.e., agent moieties), and amine donor units. For mAb2 (a chimeric IgG1 antibody), target expressing (A431, OVCAR3, BxPC3 and HT-29) or non-expressing (SW620) cells were seeded on white walled clear bottom plates at 2000 cells/well for 24 hours before treatment. Cells were treated with 4 fold serially diluted antibody-drug conjugates or free compounds (i.e., no antibody conjugated to the drug) in triplicates. Cell viability was determined by CellTiter-Glo® Luminescent Cell Viability Assay 96 (Promega, Madison Wis.) 96 hours after treatment. Relative cell viability was determined as percentage of untreated control. IC50 was calculated by Prism software. Table 6 shows the conjugation ratio and antibody IC50 in different cells using various antibody-drug conjugates and unconjugated drugs.

TABLE 6

| Sample No. | Samples | Conjugation Ratio | A431 Antibody IC50 (ug/mL) | A431 Antibody IC50 (nM) | OVCAR3 Antibody IC50 (ug/mL) | OVCAR3 Antibody IC50 (nM) | BxPC3 Antibody IC50 (ug/mL) | BxPC3 Antibody IC50 (nM) | HT-29 Antibody IC50 (ug/mL) | HT-29 Antibody IC50 (nM) | SW620 Antibody IC50 (ug/mL) | SW620 Antibody IC50 (nM) |
|---|---|---|---|---|---|---|---|---|---|---|---|---|
| Antibody-Drug Conjugates* | | | | | | | | | | | | |
| 1 | mAb2-HCQ0-Aminocaproyl-MMAF | | 41.50 | 276.00 | n/d | n/d | n/d | n/d | n/d | n/d | n/a | n/a |
| 2 | mAb2-HCQ01-Aminocaproyl-MMAF | | 9.40 | 63.00 | n/d | n/d | n/d | n/d | n/d | n/d | n/a | n/a |
| 3 | mAb2-HCQ01-Aminocaproyl-MMAF | 0.69 | 3.30 | 22.00 | 5.03 | 33.69 | n/d | n/d | n/d | n/d | n/a | n/a |
| 4 | mAb2-HCQ01-Aminocaproyl-MMAF | | 28.00 | 186.00 | n/d | n/d | n/d | n/d | n/d | n/d | n/a | n/a |
| 5 | mAb2-HCQ01-Aminocaproyl-MMAF | | 11.60 | 78.00 | n/d | n/d | n/d | n/d | n/d | n/d | n/a | n/a |
| 6 | mAb2-HCQ01-Aminocaproyl-MMAF | | 15.00 | 100.00 | n/d | n/d | n/d | n/d | n/d | n/d | n/a | n/a |
| 7 | mAb2-WT-Aminocaproyl-MMAF | | n/a | n/a | n/d | n/d | n/d | n/d | n/d | n/d | n/a | n/a |
| 8 | mAb2-HCQ01-Aminocaproyl-MMAF | 1.00 | 0.87 | 5.80 | 2.86 | 19.07 | 0.92 | 6.16 | n/d | n/d | n/a | n/a |
| 9 | mAb2-HCQ01-Aminocaproyl-VC-PABC-MMAF | 1.85 | 0.03 | 0.17 | 0.01 | 0.08 | 0.02 | 0.14 | n/d | n/d | n/a | n/a |

TABLE 6-continued

| | | | A431 | | OVCAR3 | | BxPC3 | | HT-29 | | SW620 | |
|---|---|---|---|---|---|---|---|---|---|---|---|---|
| Sample No. | Samples | Conjugation Ratio | Antibody IC50 (ug/mL) | Antibody IC50 (nM) | Antibody IC50 (ug/mL) | Antibody IC50 (nM) | Antibody IC50 (ug/mL) | Antibody IC50 (nM) | Antibody IC50 (ug/mL) | Antibody IC50 (nM) | Antibody IC50 (ug/mL) | Antibody IC50 (nM) |
| 10 | mAb2-HCQ01-Aminocaproyl-MMAF | 1.29 | 0.57 | 3.78 | 1.07 | 7.12 | 0.52 | 3.49 | n/d | n/d | n/a | n/a |
| 11 | mAb2-HCQ01-Aminocaproyl-VC-PABC-MMAF | 1.95 | 0.02 | 0.15 | 0.01 | 0.07 | 0.02 | 0.13 | n/d | n/d | n/a | n/a |
| 12 | mAb2-HCQ01-putrescinyl-geldanamycin | 0.20 | n/a | n/a | n/d | n/d | n/d | n/d | n/d | n/d | n/a | n/a |
| 13 | mAb2-HCQ01-AcLys-Putrescinyl-Geldanamycin | 1.90 | n/a | n/a | n/d | n/d | n/d | n/d | n/d | n/d | n/a | n/a |
| 14 | mAb2-HCQ01-AcLys-VC-PABC-MMAD | 1.92 | 0.02 | 0.13 | n/d | n/d | n/d | n/d | 0.02 | 0.11 | n/d | n/d |
| 15 | mAb2-HCQ01-Aminocaproyl-MMAD | 1.35 | 7.34 | 48.92 | n/d | n/d | n/d | n/d | 10.79 | 71.93 | n/d | n/d |
| 16 | mAb2-HCQ01-AcLysGly-MMAD | 1.87 | 46.97 | 313.13 | n/d | n/d | n/d | n/d | 36.34 | 242.27 | n/d | n/d |
| 17 | mAb2-HCQ01-AcLys-β-ala-MMAD | 1.95 | n/a | n/a | n/d | n/d | n/d | n/d | 5.30 | 35.31 | n/d | n/d |
| 18 | mAb2-HCQ01-Aminocaproyl-MMAE | 0.83 | n/a | n/a | n/d | n/d | n/d | n/d | n/a | n/a | n/d | n/d |
| 19 | mAb2-HCQ01-Amino-PEG2-C2-MMAE | 1.65 | 13.43 | 89.53 | n/d | n/d | n/d | n/d | n/a | n/a | n/d | n/d |
| 20 | mAb2-HCQ01-Amino-PEG2-C2-MMAE | 1.64 | 1.01 | 6.81 | n/d | n/d | n/d | n/d | n/a | n/a | n/d | n/d |
| 21 | mAb2-HCQ01-Aminocaproyl-VC-PABC-MMAE | 1.60 | 0.05 | 0.32 | n/d | n/d | n/d | n/d | n/d | n/d | n/a | n/a |
| 22 | mAb2-HCQ01-Aminocaproyl-VC-PABC-MMAE | 1.61 | n/a | n/a | n/d | n/d | n/d | n/d | n/d | n/d | n/a | n/a |
| | Free Compounds (drugs) | | | | | | | | | | | |
| 23 | Aminocaproyl-MMAF | n/a | n/d | n/d | n/d | n/d | n/a | 0.28 | n/d | n/d | n/a | 0.01 |
| 24 | VC-PABC-MMAF | n/a | n/d | n/d | n/d | n/d | n/a | 426.6 | n/d | n/d | n/a | 482.6 |
| 25 | Putrescinyl-Geldanamycin | n/a | n/a | >1000 | n/d | n/d | n/d | n/d | n/a | 317.8 | n/a | >1000 |
| 26 | AcLys-Putrescinyl-Geldanamycin | n/a | n/a | >1000 | n/d | n/d | n/d | n/d | n/d | n/d | n/a | >1000 |
| 27 | AcLys-VC-PABC-MMAD | n/a | n/a | 0.003 | n/d | n/d | n/d | n/d | n/a | 0.189 | n/d | n/d |
| 28 | Aminocaproyl-MMAD | n/a | n/a | 145.7 | n/d | n/d | n/d | n/d | n/a | 97.52 | n/d | n/d |
| 29 | AcLysGly-MMAD | n/a | n/a | 8.42 | n/d | n/d | n/d | n/d | n/a | 5.14 | n/d | n/d |
| 30 | AcLys-β-Ala-MMAD | n/a | n/a | 98.46 | n/d | n/d | n/d | n/d | n/a | 59.5 | n/d | n/d |
| 31 | Aminocaproyl-MMAE | n/a | n/a | n/a | n/d | n/d | n/d | n/d | n/a | n/a | n/d | n/d |
| 32 | Amino-PEG2-C2-MMAE | n/a | n/a | n/a | n/d | n/d | n/d | n/d | n/a | n/a | n/d | n/d |
| 33 | Amino-PEG3-C2-MMAE | n/a | n/a | 258 | n/d | n/d | n/d | n/d | n/a | 211 | n/d | n/d |

*Antibody-Drug Conjugates were conjugated in 1) 150 mM NaCl and 25 mM Tris HCL, and at pH 8.8 (for Sample Nos 3, 6, 8-22), 2) 150 mM NaCl, 25 mM HEPES, and at pH 7.0 (for Sample Nos 1 and 4 only), or 3) 150 mM NaCl, 25 mM HEPES, and at pH 8.0 (for Sample Nos 2, 5, and 7 only).
§ n/d: not determined; n/a: not applicable.

For mAb3 (a humanized IgG1 antibody), target expressing (BT474, HCC1954, MDA-MB-361-DYT2, N87) or non-expressing (MDA-MB-468) cells were seeded in 96-well cell culture plates for 24 hours before treatment. Cells were treated with 3-fold serially diluted antibody-drug conjugates or free compounds (i.e., no antibody conjugated to the drug) in duplicate at 10 concentrations. Cell viability was determined by CellTiter 96® AQ$_{ueous}$ One Solution Cell Proliferation MTS Assay (Promega, Madison Wis.) 96 hours after treatment. Relative cell viability was determined as percentage of untreated control. IC50 values were calculated using a four parameter logistic model #203 with XLfit v4.2 (IDBS, Guildford, Surry, UK). Table 7 shows the conjugation ratio and antibody IC50 in different cells using various antibody-drug conjugates at various conjugating positions.

was initiated when the average tumor volume reached approximately 400 mm$^3$. Dosing was done through bolus tail vein injection. Depending on the tumor response to treatment, animals were injected with 1-10 mg/kg of antibody drug conjugates (mAb3) and treated four times every four days. The antibody drug conjugates include mAb3-TG1-Aminocaproyl-VC-PABC-MMAD, mAb3-H10-TG6-Amino-PEG6-C2-MMAD, mAb3-N297A-Amino-PEG6-C2-MMAD, and mAb3-N297Q-Amino-PEG6-C2-MMAD. TG1 (or HCQ01), H10, and TG6 are Q-tags having the sequences of SEQ ID NOs:2, 3, and 48, respectively. The specific amino acid positions on mAb that were replaced with Q-tag (i.e., TG1, H10, and TG6) are listed in Table 9. N297A represents amino acid substitution from N to A at position 297, resulting in aglycosylation at position 297 and

TABLE 7

| Conjugating position | Q-tag or mutated sequence | Samples | Max. Loading | Payload loading | Payload (% loading) | BT475 | HCC 1954 | MDA-MB-361-DYT2 | MDA-MB-468 | N87 |
|---|---|---|---|---|---|---|---|---|---|---|
| | | | | | | | | IC50 nM | | |
| C-terminus Heavy Chain (HC) | TG1: LLQGG (SEQ ID NO: 2) | mAb3-Amino-PEG6-C2-MMAD | 2 | 1.86 | 93 | 0.19 | 0.10 | 0.24 | 843.10 | 0.81 |
| Amino acid position 297 | N297A | mAb3-Amino-PEG6-C2-MMAD | 2 | 1.81 | 90.5 | 0.19 | 0.08 | 0.22 | >1000 | 0.78 |
| Amino acid position 297 | N297Q | mAb3-Amino-PEG6-C2-MMAD | 4 | 2.98 | 74.5 | 0.17 | 0.10 | 0.15 | >1000 | 0.72 |
| C-terminus HC | TG5: LLQLLQGA (SEQ ID NO: 47) | mAb3-Amino-PEG6-C2-MMAD | 4 | 3.15 | 78.75 | 0.25 | 0.14 | 0.19 | 489.15 | 0.94 |
| Amino acid positions 190-192 and C-terminus HC | H10: LLQG (SEQ ID NO: 3) and TG6: LLQGA (SEQ ID NO: 48) | mAb3-Amino-PEG6-C2-MMAD | 4 | 3.42 | 85.5 | 0.29 | 0.11 | 0.24 | 400.00 | 0.94 |
| Amino acid positions 190-192 | H10: LLQG (SEQ ID NO: 3) | mAb3-Amino-caproyl-VC-PABC-MMAD | 2 | 1.74 | 87 | 0.20 | 0.19 | 0.90 | 802.60 | 0.39 |
| C-terminus HC | TG1: LLQGG (SEQ ID NO: 2) | mAb3-Amino-caproyl-VC-PABC-MMAD | 2 | 1.8 [Q: | 90 | 0.17 | 0.20 | 1.53 | 354.00 | 0.36 |

Example 4

In Vivo MDA-361 DYT2 Tumor Xenograft Model

Figure 9:
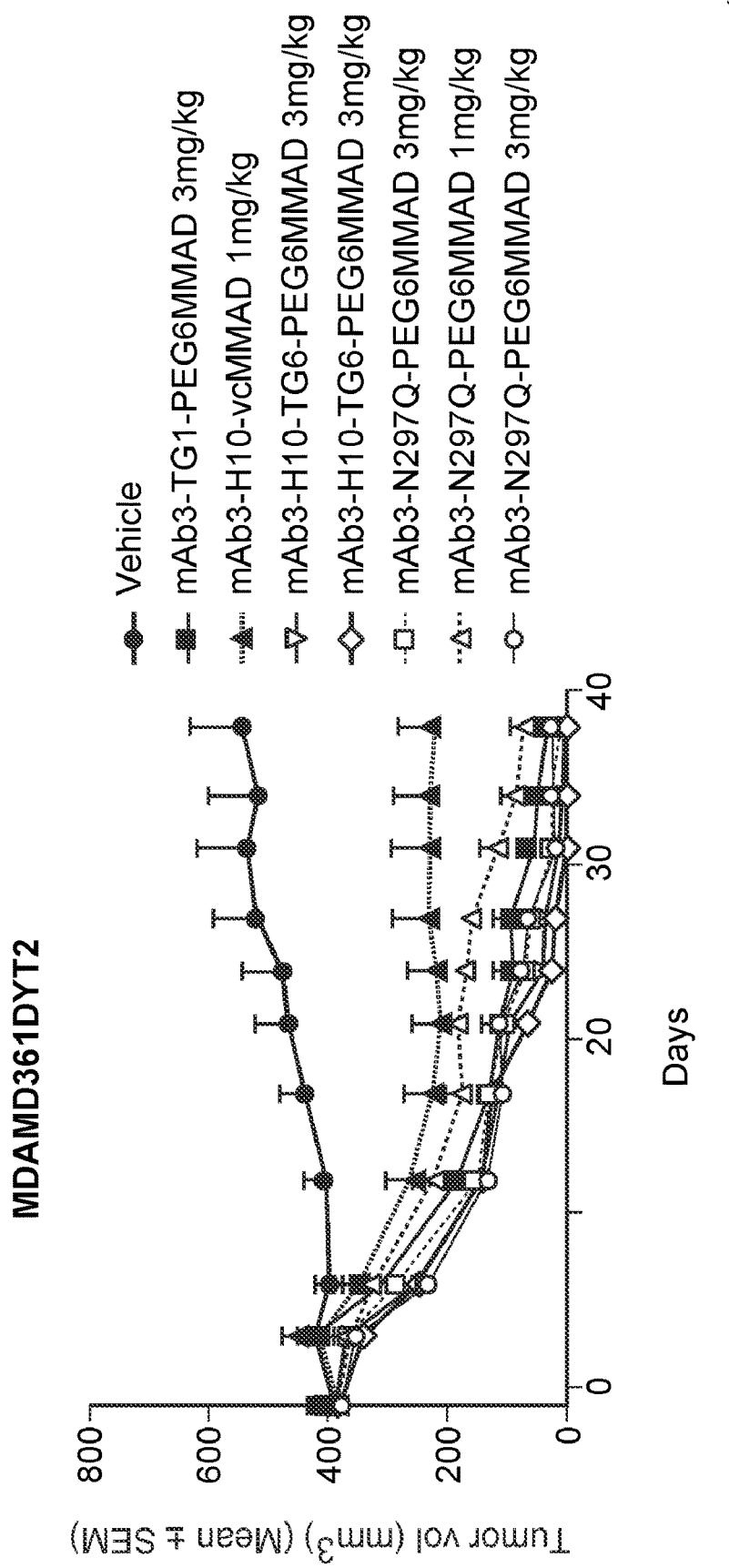
FIG. 9 shows in vivo efficacy of transglutaminase conjugated antibody (humanized IgG1) in MDA-MB361-DYT2 models. TG1 (or HCQ01), H10, and TG6 are Q-tags having the sequences of SEQ ID NOs:2, 3, and 48, respectively. N297A represents amino acid substitution from N to A at position 297, resulting in aglycosylation at position 297 and accessible/reactive endogenous glutamine at position 295. N297Q represents amino acid substitution from N to Q at position 297, resulting in aglycosylation at position 297 and accessible/reactive endogenous glutamines at positions 295 and 297. PEG6MMAD represents amino-PEG6-C2-MMAD, and vcMMAD represents aminocaproyl-VC-PABC-MMAD. Vehicle is PBS (phosphate buffered saline) solution only.

In vivo efficacy studies of antibody-drug conjugates were performed with target-expressing xenograft models using the MDA-361 DYT2 cell lines. For DYT2 efficacy studies, 10 million tumor cells in 50% matrigel were implanted subcutaneously into 6-8 week old irradiated nude mice until the tumor sizes reached between 250-350 mm$^3$. Treatment accessible/reactive endogenous glutamine at position 295. N297Q represents amino acid substitution from N to Q at position 297, resulting in aglycosylation at position 297 and accessible/reactive endogenous glutamines at positions 295 and 297. All experimental animals were monitored for body weight changes weekly. Tumor volume was measured twice a week for the first 50 days and once weekly thereafter by a Caliper device and calculated with the following formula: Tumor volume=(length×width$^2$)/2. Animals were humanely sacrificed before their tumor volumes reached 2500 mm$^3$. In all animals treated with antibody drug conjugate, tumor regression was observed within a week after dosing and continued for at least 5 weeks for all conjugates. See FIG. 9. In contrast, tumor volume increased in animals dosed with vehicle only. See FIG. 9. These results demonstrate that the antibody drug conjugates prepared by the methods described herein are effective in reducing tumor size in a mouse xenograft model.

Example 5

In Vivo N87 Tumor Xenograft Model

Figure 10:
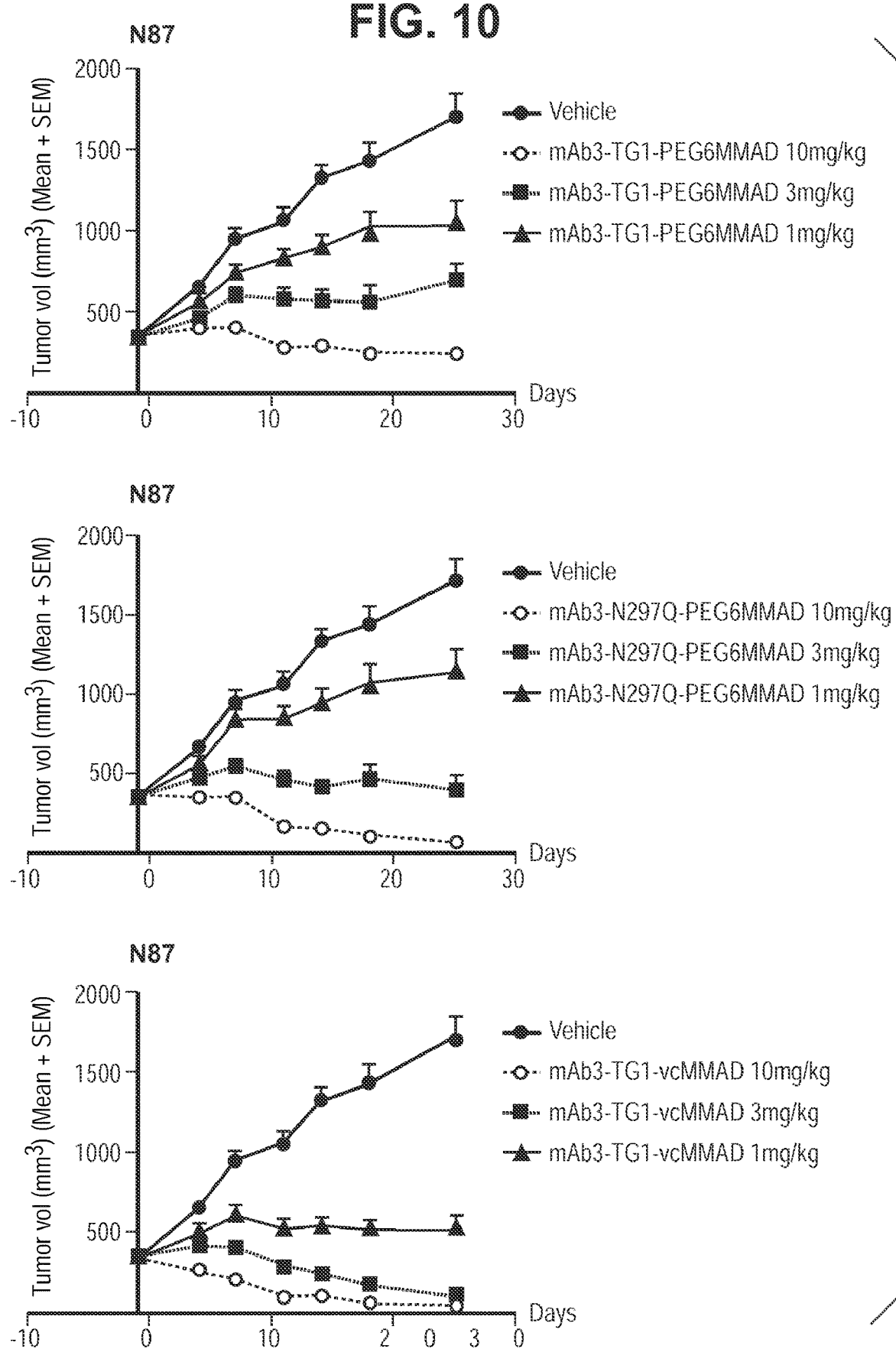
FIG. 10 shows In vivo efficacy of transglutaminase conjugated antibody (humanized IgG1) in N87 models. TG1 (or HCQ01) corresponds to SEQ ID NO:2. N297Q represents amino acid substitution from N to Q at position 297, resulting in aglycosylation at position 297 and accessible/reactive endogenous glutamines at positions 295 and 297. PEG6MMAD represents amino-PEG6-C2-MMAD, and vcMMAD represents aminocaproyl-VC-PABC-MMAD. Vehicle is PBS (phosphate buffered saline) solution only.

In vivo efficacy studies of antibody-drug conjugates were performed with target-expressing xenograft models using the N87 cell lines. For efficacy study, 7.5 million tumor cells in 50% matrigel were implanted subcutaneously into 6-8 weeks old nude mice until the tumor sizes reached between 250 and 350 mm$^3$. Treatment was initiated when the average tumor volume reached 400 mm$^3$. Dosing was done through bolus tail vein injection. Depending on the tumor response to treatment, animals were injected with 1-10 mg/kg (1, 3, and 10 mg/kg; n=8 per group) of antibody drug conjugates (mAb3) and treated four times every four days. The antibody drug conjugates include mAb3-TG1-Aminocaproyl-VC-PABC-MMAD, mAb3-TG1-Amino-PEG6-C2-MMAD, and mAb3-N297Q-Amino-PEG6-C2-MMAD. The Q-tag TG1 (or HCQ01) corresponds to SEQ ID NO:1. The specific amino acid position on mAb that was replaced with Q-tag TG1 is listed in Table 9. N297Q represents amino acid substitution from N to Q at position 297, resulting in aglycosylation at position 297 and accessible/reactive endogenous glutamines at positions 295 and 297. All experimental animals were monitored for body weight changes weekly. Tumor volume was measured twice a week for the first 50 days and once weekly thereafter by a Caliper device and calculated with the following formula: Tumor volume=(length×width$^2$)/2. Animals were humanely sacrificed before their tumor volumes reached 2500 mm$^3$. Tumor regression was observed after one week for all conjugates at 10 mg/kg, and for the 3 mg/kg mAb3-TG1-Aminocaproyl-VC-PABC-MMAD group. Tumor inhibition was observed for the remaining conjugates at 3 mg/kg and 1 mg/kg doses. FIG. 10. These results also demonstrate that the antibody drug conjugates prepared by the methods described herein are effective in reducing tumor size in a mouse xenograft model.

Example 6

In Vivo BxPC3 Tumor Xenograft Model

Figure 11:
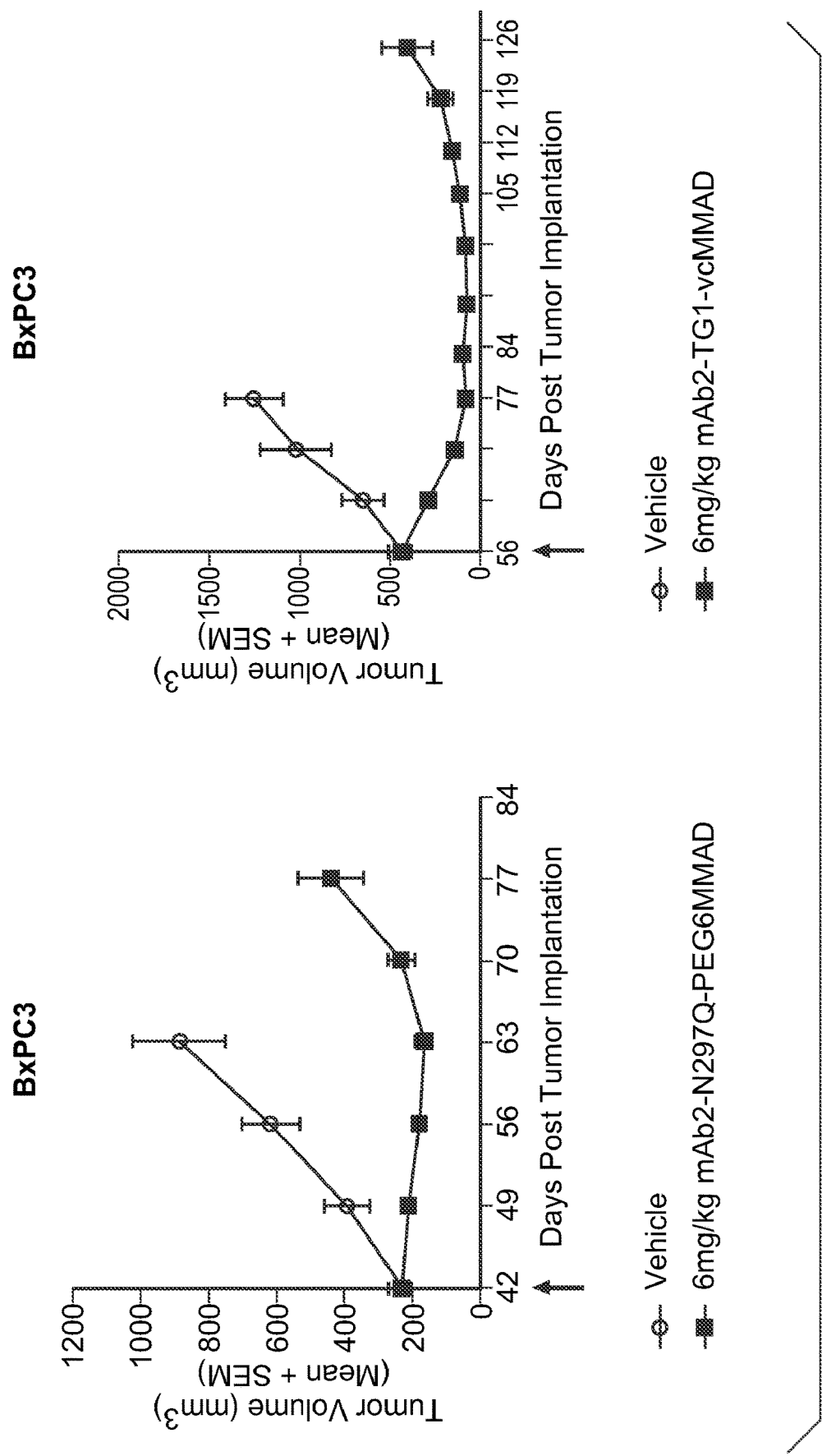
FIG. 11 shows in vivo efficacy of transglutaminase conjugated antibody (chimeric IgG1) in BxPC3 models. N297Q represents amino acid substitution from N to Q at position 297, resulting in aglycosylation at position 297 and accessible/reactive endogenous glutamines at positions 295 and 297. PEG6MMAD represents amino-PEG6-C2-MMAD, and vcMMAD represents aminocaproyl-VC-PABC-MMAD. Vehicle is PBS (phosphate buffered saline) solution only.

In vivo efficacy studies of antibody-drug conjugates were performed with target-expressing BxPC3 xenograft. Tumor cells were implanted subcutaneously into 5-8 weeks old SCID (Severely Combined Immunodeficient) mice until the tumor sizes reached at least 200 mm$^3$. Treatment was initiated when the average tumor volume reached 200-400 mm$^3$. Dosing was done through bolus tail vein injection. Depending on the tumor response to treatment, animals were injected with 1-10 mg/kg of antibody drug conjugates (mAb2) and treated with one single dose. The antibody drug conjugates include mAb2-TG1-Aminocaproyl-VC-PABC-MMAD, and mAb2-N297Q-Amino-PEG6-C2-MMAD. The Q-tag TG1 (or HCQ01) corresponds to SEQ ID NO:1. The specific amino acid position on mAb that was replaced with Q-tag TG1 is listed in Table 9. N297Q represents amino acid substitution from N to Q at position 297, resulting in aglycosylation at position 297 and accessible/reactive endogenous glutamines at positions 295 and 297. All experimental animals were monitored for body weight changes weekly. Tumor volume was measured once a week by a Caliper device and calculated with the following formula: Tumor volume=(length×width)/2. Animals were humanely sacrificed before their tumor volumes reached 2000 mm$^3$. Upon tumor regression, animals were monitored continuously for tumor re-growth after the treatment was discontinued. Tumor regression was observed one week after dosing and continued for 3 weeks for mAb2-N297Q-PEG6MMAD (left panel, FIG. 11) and more than 6 weeks for mAb2-TG1-vcMMAD (right panel, FIG. 11). TG1 (or HCQ01) corresponds to SEQ ID NO:2. These results also demonstrate that the antibody drug conjugates prepared by the methods described herein are effective in reducing tumor size in a mouse xenograft model.

Example 7

Conjugation Site Scanning

The efficiencies of transglutaminase-catalyzed conjugation at various sites on IgG1 antibodies (mAb 2 or mAb4) were explored. Portions of exposed loops (e.g., 1-5 amino acids in length) of an antibody were either replaced with a Q-tag of various lengths, or Q-tag was inserted in these loops. mAb2 and mAb4 mutants were conjugated to various linker-payload (amine donor agents) using transglutaminase, and conjugation yield was determined as described in example 1. The list of tested amino acid positions, Q-tag sequences, and conjugation yields are shown in Tables 8 and 9.

TABLE 8

| Name | Amino Acid Positions | Q-tag sequences | Linker-payload | Maximum loading | Payload (loading) | Payload (% loading) | IC50 nM A431 | IC50 nM BxPC3 | IC50 nM Colo205 |
|---|---|---|---|---|---|---|---|---|---|
| mAb2TG1 | C-terminus HC | LLQGG (SEQ ID NO: 2) | Amino-PEG6-C2-MMAD | 2 | 1.82 | 91.0 | 0.520 | 0.443 | >266 |
| mAb2H10 | 190-192 | LLQG (SEQ ID NO: 3) | Amino-PEG6-C2-MMAD | 2 | 1.47 | 73.5 | 0.647 | 0.080 | >266 |
| mAb2297A | 297 | A | Amino-PEG6-C2-MMAD | 2 | 1.78 | 89.0 | 0.400 | 0.137 | >266 |

TABLE 8-continued

| Name | Amino Acid Positions | Q-tag sequences | Linker-payload | Maximum loading | Payload (loading) | Payload (% loading) | IC50 nM A431 | IC50 nM BxPC3 | IC50 nM Colo205 |
|---|---|---|---|---|---|---|---|---|---|
| mAb2TG5 | C-terminus HC | LLQLLQGA (SEQ ID NO: 47) | Amino-PEG6-C2-MMAD | 4 | 2.31 | 57.8 | 0.367 | 0.350 | 0.167 |
| mAb2H10a | 180-192 | LLQYQG (SEQ ID NO: 51) | Amino-PEG6-C2-MMAD | 4 | 2.35 | 58.8 | 0.340 | 0.058 | 44.920 |
| mAb2H10 & TG6 | 190-192 & C-terminus HC | LLQG (SEQ ID NO: 3) & LLQGA (SEQ ID NO: 48) | Amino-PEG6-C2-MMAD | 4 | 3.49 | 87.3 | 0.347 | 0.094 | 2.977 |
| mAb2297Q | 297 | Q | Amino-PEG6-C2-MMAD | 4 | 3.53 | 88.3 | 0.153 | 0.029 | 1.460 |
| mAb2TG1 | C-terminus HC | LLQGG (SEQ ID NO: 2) | Aminocaproyl-VC-PABC-MMAD | 2 | 1.94 | 97.0 | 0.140 | 0.131 | 1.213 |
| mAb2H10 | 190-192 | LLQG (SEQ ID NO: 3) | Aminocaproyl-VC-PABC-MMAD | 2 | 1.65 | 82.5 | 0.033 | 0.041 | 15.727 |
| mAb2297A | 297 | A | Aminocaproyl-VC-PABC-MMAD | 2 | 1.62 | 81.0 | 0.053 | 0.149 | 4.713 |
| mAb2TG5 | C-terminus HC | LLQLLQGA (SEQ ID NO: 47) | AcLys-VC-PABC-MMAD | 4 | 2.00 | 50.0 | 0.073 | 0.135 | 0.120 |
| mAb2H10a | 189-192 | LLQYQG (SEQ ID NO: 51) | AcLys-VC-PABC-MMAD | 4 | 2.96 | 74.0 | 0.060 | 0.027 | 0.467 |
| mAb2H10 & TG6 | 190-192 & C-terminus HC | LLQG (SEQ ID NO:3) & LLQGA (SEQ ID NO: 48) | Aminocaproyl-VC-PABC-MMAD | 4 | 3.65 | 91.3 | 0.040 | 0.021 | 0.060 |
| mAb2297Q | 297 | Q | Aminocaproyl-VC-PABC-MMAD | 4 | 3.55 | 88.0 | 0.053 | 0.033 | 0.233 |

TABLE 9

| Name | Amino Acid Position(s) | Wild type Sequences | Q tag or mutated sequences | Maximum loading | Alexa 488 Conjugation (loading) | Alexa 488 Conjugation (%) |
|---|---|---|---|---|---|---|
| mAb4 WT | | | | | | |
| mAb4 HCQ01 | 447 | K | LLQGG (SEQ ID NO: 2) | 2 | 1.75 | 85.0 |
| mAb4 H1 | 1 | N-term | LLQGSG (SEQ ID NO: 50) | 2 | 1.22 | 60.9 |
| MAb4 H2 | 15-17 | SQS | LLQG (SEQ ID NO: 3) | 2 | 0.01 | 0.6 |
| MAb4 H3 | 62-65 | PFTS (SEQ ID NO: 57) | LLQG (SEQ ID NO: 3) | 2 | 0.03 | 1.4 |
| MAb4 H4 | 72-75 | DNSK (SEQ ID NO: 58) | LLQG (SEQ ID NO: 3) | 2 | 0.01 | 0.6 |

TABLE 9-continued

| Name | Amino Acid Position(s) | Wild type Sequences | Q tag or mutated sequences | Maximum loading | Alexa 488 Conjugation (loading) | Alexa 488 Conjugation (%) |
|---|---|---|---|---|---|---|
| MAb4 H5 | 82b-84 | SLQS (SEQ ID NO: 59) | LLQG (SEQ ID NO: 3) | 2 | 0.01 | 0.4 |
| MAb4 H6 | 113-120 | SAST (SEQ ID NO: 60) | LLQG (SEQ ID NO: 3) | 2 | 0.13 | 6.5 |
| MAb4 H6a | 114-120 | AST | LLQG (SEQ ID NO: 3) | 2 | 0.01 | 0.4 |
| MAb4 H6b | 113-119 | SAS | LLQG (SEQ ID NO: 3) | 2 | 0.01 | 0.5 |
| MAb4 H6c | 114-119 | AS | LLQG (SEQ ID NO: 3) | 2 | 0.04 | 2.0 |
| MAb4 H7 | 134-136 | STS | LLQ | 2 | 0.05 | 2.7 |
| MAb4 H7a | 136 | S | LLQ (SEQ ID NO: 3) | 2 | 0.04 | 2.2 |
| MAb4 H7b | 135-136 | TS | LLQG (SEQ ID NO: 3) | 2 | 0.14 | 7.2 |
| MAb4 H7c | 135 | insertion | LLQG (SEQ ID NO: 3) | 2 | 1.92 | 96.1 |
| MAb4 H8 | 159-162 | NSGA (SEQ ID NO: 61) | LLQG (SEQ ID NO: 3) | 2 | 0.04 | 2.1 |
| MAb4 H8a | 160 | insertion | LLQG (SEQ ID NO: 3) | 2 | 1.87* | 93.4* |
| MAb4 H9 | 175-177 | QSS | LLQ | 2 | 0.01 | 0.3 |
| MAb4 H9a | 176 | insertion | LLQG (SEQ ID NO: 3) | 4 | 0.06 | 1.4 |
| MAb4 H10 | 190-192 | SSS | LLQG (SEQ ID NO: 3) | 2 | 1.72 | 86.1 |
| MAb4 H10a | 189-192 | PSSS (SEQ ID NO: 62) | LLQYQG (SEQ ID NO: 51) | 4 | 1.92 | 47.9 |
| MAb4 H10b | 189-192 | PSSS (SEQ ID NO: 62) | LLQLLQG (SEQ ID NO: 52) | 4 | 0.85 | 21.3 |
| MAb4 H11 | 194-196 | GTQ | LQG | 2 | 0.01 | 0.7 |
| MAb4 H11.5a | 206-208 | PSN | LLQG (SEQ ID NO: 3) | 2 | 0.02 | 1.1 |
| MAb4 H11.5b | 205-207 | KPS | LLQG (SEQ ID NO: 3) | 2 | 0.03 | 1.7 |
| MAb4 H11.5c | 206 | insertion | LLQG (SEQ ID NO: 3) | 2 | 0.02 | 0.9 |
| MAb4 H12 | 222-225 | KTHT (SEQ ID NO: 63) | LLQG (SEQ ID NO: 3) | 2 | 0.25 | 12.5 |
| MAb4 H12a | 223-225 | THT | LLQG (SEQ ID NO: 3) | 2 | 0.02 | 1.0 |
| MAb4 H12b | 222-224 | KTH | LLQG (SEQ ID NO: 3) | 2 | 0.01 | 0.6 |
| MAb4 H12c | 222-223 | KT | LLQG (SEQ ID NO: 3) | 2 | 1.79* | 89.3* |
| MAb4 H12d | 223 | insertion | LLQG (SEQ ID NO: 3) | 2 | 0.76* | 37.8* |
| MAb4 H13 | 252-254 | MIS | LQG | 2 | 0.75 | 37.5 |
| MAb4 H13a | 251-254 | LMIS (SEQ ID NO: 64) | SLLQG (SEQ ID NO: 53) | 2 | 1.86 | 92.8 |

TABLE 9-continued

| Name | Amino Acid Position(s) | Wild type Sequences | Q tag or mutated sequences | Maximum loading | Alexa 488 Conjugation (loading) | Alexa 488 Conjugation (%) |
|---|---|---|---|---|---|---|
| MAb4 H13b | 252-253 | MI | LQG | 2 | 1.36 | 67.8 |
| MAb4 H14 | 267-270 | SHED (SEQ ID NO: 65) | LLQG (SEQ ID NO: 3) | 2 | 0.01 | 0.7 |
| MAb4 H15a | 282-284 | VEV | LLQG (SEQ ID NO: 3) | 2 | 0.01 | 0.6 |
| MAb4 H15b | 281-283 | GVE | LLQG (SEQ ID NO: 3) | 2 | 0.42 | 21.2 |
| MAb4 H16 | 294-297 | EQYN (SEQ ID NO: 66) | LLQG (SEQ ID NO: 3) | 2 | 1.93* | 96.4* |
| MAb4 H16a | 293-297 | EEQYN (SEQ ID NO: 67) | LLQLQG (SEQ ID NO: 52) | 4 | 3.48* | 87.0* |
| MAb4 H16b | 293-297 | EEQYN (SEQ ID NO: 67) | LLQLLQG (SEQ ID NO: 52) | 4 | 3.40* | 84.9* |
| MAb4 H16c | 294-297 | EQYN (SEQ ID NO: 66) | LLQLQ (SEQ ID NO: 54) | 4 | 3.16* | 79.1* |
| MAb4 H16d | 294-297 | EQYN (SEQ ID NO: 66) | LLQLLQ (SEQ ID NO: 55) | 4 | 3.37* | 84.3* |
| MAb4 N297A | 297 | N | A | 2 | 1.61* | 80.5* |
| MAb4 N297Q | 297 | N | Q | 4 | 2.57* | 64.3* |
| MAb4 H17 | 310-312 | HQD | LQG | 2 | 0.02 | 0.8 |
| MAb4 H18 | 324-327 | SNKA (SEQ ID NO: 68) | LLQG (SEQ ID NO: 3) | 2 | 0.02 | 1.2 |
| MAb4 H18a | 325 | insertion | LLQG (SEQ ID NO: 3) | 2 | 0.07 | 3.6 |
| MAb4 H19 | 340-342 | KGQ | LLQG (SEQ ID NO: 3) | 2 | 0.08 | 3.9 |
| MAb4 H20 | 357-360 | EMTK (SEQ ID NO: 69) | LLQG (SEQ ID NO: 3) | 2 | 0.01 | 0.6 |
| MAb4 H20a | 359 | insertion | LLQG (SEQ ID NO: 3) | 2 | 0.05 | 2.5 |
| MAb4 H21 | 384-386 | NGQ | LLQG (SEQ ID NO: 3) | 2 | 0.01 | 0.3 |
| MAb4 H21a | 385 | insertion | LLQG (SEQ ID NO: 3) | 4 | 2.05* | 51.2* |
| MAb4 H22 | 418 | Q | LL | 2 | 0.02 | 1.1 |
| MAb4 H23 | 431-434 | ALHN (SEQ ID NO: 70) | LLQG (SEQ ID NO: 3) | 2 | 0.00 | 0.0 |
| MAb4 H23a | 432 | insertion | LLQG (SEQ ID NO: 3) | 2 | 0.00 | 0.0 |
| MAb4 H24 | 444-445 | SP | LQ | 2 | 0.01 | 0.7 |
| MAb4 L1 | 16-17 | GE | LLQG (SEQ ID NO: 3) | 2 | 0.05 | 2.5 |
| MAb4 L2 | 60-61 | SR | LLQG (SEQ ID NO: 3) | 2 | 0.46 | 23.2 |
| MAb4 L3 | 78-81 | VESE (SEQ ID NO: 71) | LLQG (SEQ ID NO: 3) | 2 | 0.01 | 0.4 |
| MAb4 L4 | 107-110 | KRTV (SEQ ID NO: 72) | LLQG (SEQ ID NO: 3) | 2 | 0.01 | 0.3 |

TABLE 9-continued

| Name | Amino Acid Position(s) | Wild type Sequences | Q tag or mutated sequences | Maximum loading | Alexa 488 Conjugation (loading) | Alexa 488 Conjugation (%) |
|---|---|---|---|---|---|---|
| MAb4 L4a | 109-110 | TV | LLQG (SEQ ID NO: 3) | 2 | 0.02 | 0.8 |
| MAb4 L4b | 108 | insertion | LLQG (SEQ ID NO: 3) | 2 | 0.60 | 29.8 |
| MAb4 L5 | 121-124 | SDEQ (SEQ ID NO: ) | LLQG (SEQ ID NO: 3) | 2 | 0.03 | 1.5 |
| MAb4 L5a | 122 | insertion | LLQG (SEQ ID NO: 3) | 4 | 0.00 | 0.1 |
| MAb4 L6 | 124-127 | QLKS (SEQ ID NO: 74) | LLQG (SEQ ID NO: 3) | 2 | 0.02 | 1.1 |
| MAb4 L7 | 153-156 | ALQS (SEQ ID NO: 75) | LLQG (SEQ ID NO: 3) | 2 | 0.01 | 0.6 |
| MAb4 L7a | 154 | insertion | LLQG (SEQ ID NO: 3) | 4 | 0.00 | 0.0 |
| MAb4 L8 | 167-170 | DSKD (SEQ ID NO: 76) | LLQG (SEQ ID NO: 3) | 2 | 0.00 | 0.0 |
| MAb4 L8a | 168 | insertion | LLQG (SEQ ID NO: 3) | 2 | 1.93 | 96.3 |
| MAb4 L9 | 182-185 | SKAD (SEQ ID NO: 77) | LLQG (SEQ ID NO: 3) | 2 | 0.03 | 1.4 |
| MAb4 L9a | 184 | insertion | LLQG (SEQ ID NO: 3) | 2 | 0.01 | 0.4 |
| MAb4 L10 | 186-189 | YEKH (SEQ ID NO: 78) | LLQG (SEQ ID NO: 3) | 2 | 0.01 | 0.5 |
| MAb4 L11 | 200-203 | GLSS (SEQ ID NO: 79) | LLQG (SEQ ID NO: 3) | 2 | 0.21 | 10.6 |
| MAb4 L11a | 202-203 | SS | LQG | 2 | 0.01 | 0.7 |
| MAb4 L11b | 200-202 | GLS | LLQG (SEQ ID NO: 3) | 2 | 1.95 | 97.3 |
| MAb4 L11c | 200-202 | GLS | LLQGR (SEQ ID NO: 56) | 2 | 1.99* | 99.3* |
| MAb4 L11d | 202 | S | LLQGR (SEQ ID NO: 56) | 2 | 0.14 | 6.8 |
| MAb4 L12 | 211-214 | RGEC (SEQ ID NO: 80) | LLQG (SEQ ID NO: 3) | 2 | 0.05 | 2.5 |
| MAb4 TG4 | 447 | K | LLQYQGA (SEQ ID NO: 49) | 4 | 2.30 | 57.6 |
| MAb4 TG5 | 447 | K | LLQLLQGA (SEQ ID NO: 47) | 4 | 2.69 | 67.2 |
| MAb4 TG6 | 447 | K | LLQGA (SEQ ID NO: 48) | 2 | 1.82 | 91.1 |
| MAb4 H10 TG6 | 190-192/ 447 | | See above | 4 | 3.68 | 92.1 |

*Indicates that the conjugation reaction was run at 37° C. rather than at room temperature.

Example 8

In Vivo Antibody Conjugate Stability Determination

Figure 12:
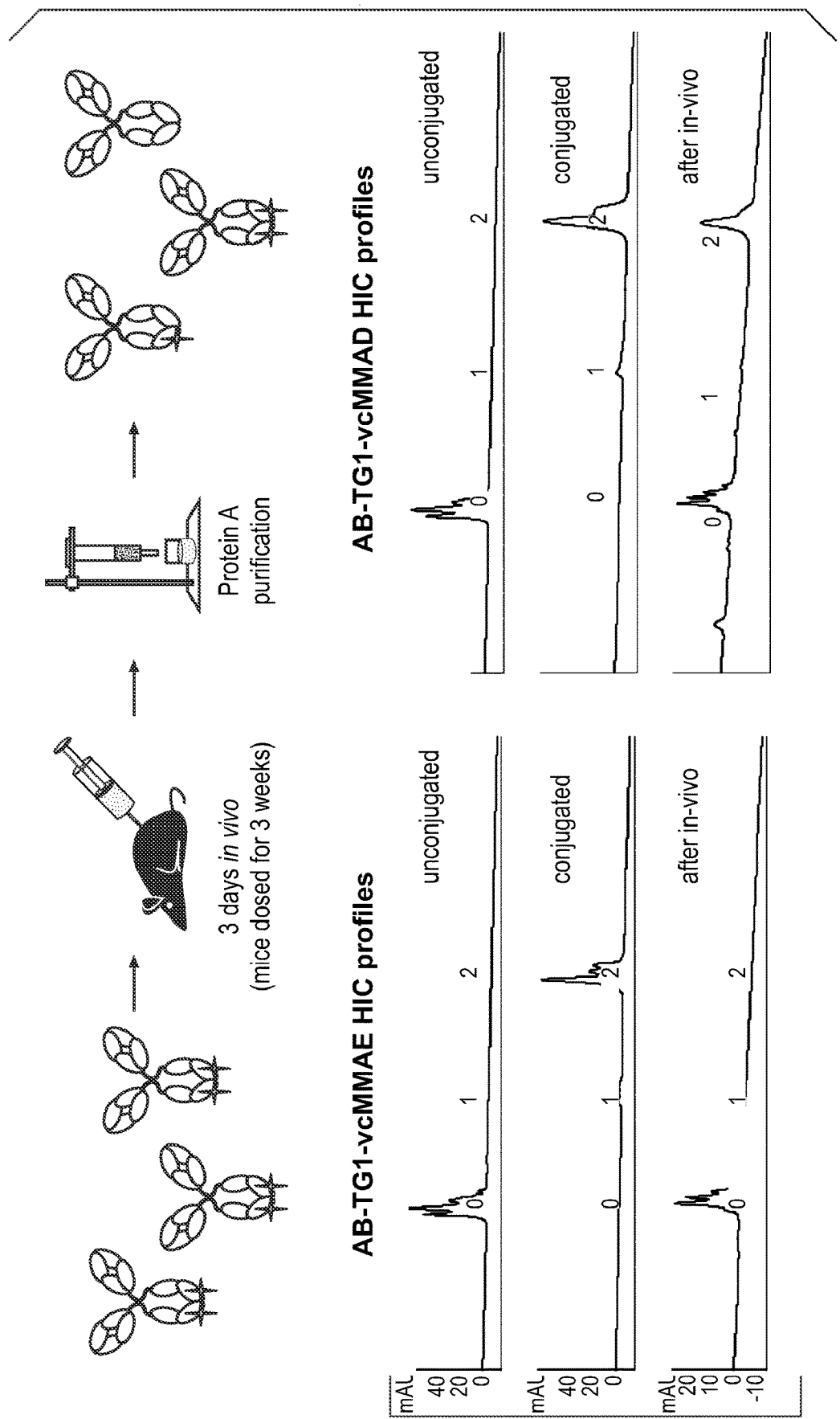
FIG. 12 shows in vivo antibody conjugate stability determination. Antibody engineered with Q-tag (TG1 (SEQ ID NO:1)) was conjugated to either aminocaproyl-VC-PABC-MMAE or aminocaproyl-VC-PABC-MMAD and was injected into SCID (Severely Combined Immunodeficient) mice.

Antibody (mAb2) engineered with Q-tag (SEQ ID NO:2) at C-terminus (amino acid position 447) was conjugated to either aminocaproyl-VC-PABC-MMAE or aminocaproyl-VC-PABC-MMAD and was injected at 10 mg/kg into SCID mice. The mice were then sacrificed 3 days later. Antibody conjugates were purified from the mouse plasma using Protein A, and run on HIC column to quantify the amount conjugate remaining as was described in Example 1. The aminocaproyl-VC-PABC-MMAE conjugated at the C-terminus with Ab-TG1 was found to be nearly completely cleaved in vivo after 3 days. The aminocaproyl-VC-PABC-MMAD conjugated at the C-terminus with Ab-TG1 was found to have approximately 60% of the intact conjugate left after 3 days in vivo. See FIG. 12.

Example 9

Site-Specific Fab Conjugation Using a Transglutaminase

Fab conjugation to a biocompatible polymer is achieved via microbial transglutaminase-catalyzed transamidation reaction between a Fab fragment carrying a glutamine tag (Q-tag) on the heavy and/or light chains and an amine-containing biocompatible polymer. In this transamidation reaction, the glutamine on the Fab fragment acts as an acyl donor, and the amine-containing polymer acts as an acyl acceptor (amine donor). Purified Fab is incubated with an excess acyl acceptor in the presence of Streptoverticillium mobaraense transglutaminase (ACTIVA™, Ajinomoto, Japan). The reaction conditions are adjusted for individual acyl acceptor derivatives. Following incubation at room temperature or at 37° C. for the Fab conjugate is purified using standard affinity chromatography methods known to persons skilled in the art, as described in Example 1. The conjugation efficiency is determined by mass spectrometry, hydrophobic chromatography, or spectrophotometry (relative absorbance), or ion exchange chromatography. The efficiencies of transglutaminase-catalyzed conjugation between Fab fragment and biocompatible polymer are better than 50% and result in homogeneous site specific conjugation.

Example 10

Site-Specific Toxin Polypeptide Conjugation Using a Transglutaminase

Toxin polypeptide conjugation to a biocompatible polymer is achieved via microbial transglutaminase-catalyzed transamidation reaction between a toxin polypeptide carrying a glutamine tag (Q-tag) and an amine-containing polymer or between a toxin polypeptide carrying primary amine and biocompatible polymer carrying glutamine tag. Toxin polypeptide can be an inhibitory cysteine knot (such as ceratotoxin), conotoxin (such as KIIIA or SmIIIa), or any other small toxin protein scaffold. In this transamidation reaction, the glutamine acts as an acyl donor, and the amine acts as an acyl acceptor. Purified toxin polypeptide is incubated with acyl acceptor in the presence of Streptoverticillium mobaraense transglutaminase (ACTIVA™, Ajinomoto, Japan). The reaction conditions are adjusted for individual acyl acceptor derivatives. Following incubation at room temperature the toxin polypeptide conjugate is purified using standard affinity chromatography methods known to persons skilled in the art. The conjugation efficiency is determined by mass spectrometry, hydrophobic chromatography, or ion exchange chromatography. The efficiencies of transglutaminase-catalyzed conjugation between toxin polypeptide and biocompatible polymer are better than 50% and results in homogeneous site specific conjugation.

Example 11

Site-Specific Drug Conjugation to the Antibody Loop Using a Transglutaminase

Conjugation of different drugs (e.g., MMAE, MMAD, MMAF, or geldanamycin) to an antibody on its loop is achieved via microbial transglutaminase-catalyzed transamidation reaction between an antibody carrying a glutamine tag (Q-tag) in a loop of the heavy and/or light chains and a drug containing an amine donor unit (e.g., Aminocaproyl-Val-Cit-PABC, Ac-Lys-putrescine, Ac-Lys-β-Ala, or Ac-Lys-Val-Cit-PABC). In this transamidation reaction, the glutamine in the antibody loop acts as an acyl donor, and the amine donor unit linked to the drug acts as an acyl acceptor (amine donor). Purified antibody is incubated with an excess acyl acceptor in the presence of Streptoverticillium mobaraense transglutaminase (ACTIVA™, Ajinomoto, Japan). The reaction conditions are adjusted for individual acyl acceptor derivatives. Following incubation at room temperature, the antibody-drug conjugate is purified using standard affinity chromatography methods known to persons skilled in the art, as described in Example 1. The conjugation efficiency is determined by mass spectrometry, hydrophobic chromatography, or ion exchange chromatography. The efficiencies of transglutaminase-catalyzed conjugation between antibody and the drug are better than 50% and result in homogeneous site specific conjugation at the site of an antibody loop.

Although the disclosed teachings have been described with reference to various applications, methods, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

What is claimed is:

1. An isolated engineered Fc-containing antibody conjugate comprising the formula: (Fc-containing antibody)-T-A, wherein T is an acyl donor glutamine-containing tag engineered at a specific site; wherein A is an amine donor agent; wherein the amine donor agent is site-specifically conjugated to the acyl donor glutamine-containing tag at position 294 or 296 (EU numbering system) in the Fc-containing antibody, wherein the acyl donor glutamine-containing tag is LLQG (SEQ ID NO:3).

2. The engineered Fc-containing antibody conjugate of claim 1, wherein the antibody is an IgG.

3. The engineered Fc-containing antibody conjugate of claim 1, wherein the amine donor agent comprises the formula:
X-Y-Z, wherein X is an amine donor unit; Y is a linker; and Z is an agent moiety.

4. The engineered Fc-containing antibody conjugate of claim 3, wherein the amine donor unit-linker (X-Y) is selected from the group consisting of Ac-Lys-Gly, aminocaproic acid, Ac-Lys-β-Ala, amino-PEG2-C2, amino-PEG3-C2, amino-PEG6-C2, Ac-Lys-Val-Cit-PABC, aminocaproyl-Val-Cit-PABC, putrescine, and Ac-Lys-putrescine.

5. The engineered Fc-containing antibody conjugate of claim 3, wherein the agent moiety is a cytotoxic agent.

6. The engineered Fc-containing antibody conjugate of claim 5, wherein the cytotoxic agent is selected from the group consisting of an anthracycline, an auristatin, a dolastatin, a duocarmycin, an enediyne, a geldanamycin, a maytansine, a puromycin, a taxane, a vinca alkaloid, SN-38, a tubulysin, a hemiasterlin, and stereoisomers, and isosteres thereof.

* * * * *

SEQUENCE LISTING

```
<160> NUMBER OF SEQ ID NOS: 82

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa = Leu, Ala, Gly, Ser, Val, Phe, Tyr, His,
      Arg, Asn, Glu, Asp, Cys, Gln, Ile, Met, Pro, Thr, Lys, or Trp
```

```
<220> FEATURE:
<221> NAME/KEY: MISC_FEATURE
<222> LOCATION: (4)..(4)
<223> OTHER INFORMATION: Xaa = Leu, Ala, Gly, Ser, Val, Phe, Tyr, His,
      Arg, Asn, Glu, Asp, Cys, Gln, Ile, Met, Pro, Thr, Lys, or Trp

<400> SEQUENCE: 1

Xaa Xaa Gln Xaa
1

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Leu Leu Gln Gly Gly
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Leu Leu Gln Gly
1

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Leu Ser Leu Ser Gln Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Gly Gly Gly Leu Leu Gln Gly Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Gly Leu Leu Gln Gly
1               5
```

```
<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Gly Ser Pro Leu Ala Gln Ser His Gly Gly
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Synthetic Construct

<400> SEQUENCE: 8

Gly Leu Leu Gln Gly Gly Gly
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

Gly Leu Leu Gln Gly Gly
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic Construct

<400> SEQUENCE: 10

Gly Leu Leu Gln
1

<210> SEQ ID NO 11
<211> LENGTH: 4
<212> TYPE: PRT
<213> ORGANISM: Artificial Sequence
<220> FEATURE:
<223> OTHER INFORMATION: Synthetic Construct

<400> SEQUENCE: 11

Gly Lys Gly Gly
1

<210> SEQ ID NO 12
<211> LENGTH: 5
<212> TYPE: PRT
<213> ORGANISM: Artificial Sequence
<220> FEATURE:
<223> OTHER INFORMATION: Synthetic Construct

<400> SEQUENCE: 12

Gly Ser Lys Gly Gly
1               5
```

```
<210> SEQ ID NO 13
<211> LENGTH: 6
<212> TYPE: PRT
<213> ORGANISM: Artificial Sequence
<220> FEATURE:
<223> OTHER INFORMATION: Synthetic Construct

<400> SEQUENCE: 13

Gly Ser Gly Lys Gly Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Gly Ser Gly Gly Lys Gly Gly
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Leu Ser Leu Ser Pro Gly Leu Leu Gln Gly Gly
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Leu Ser Leu Ser Pro Gly Leu Leu Gln Gly
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Leu Ser Leu Ser Gln Gly Gly
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Gly Leu Leu Gln Val Gln Leu Lys Glu
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Leu Leu Gln Val Gln Leu Lys Glu
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct

<400> SEQUENCE: 20

Gly Leu Val Gln Leu Lys Glu
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Construct

<400> SEQUENCE: 21

Leu Val Gln Leu Lys Glu
1               5

<210> SEQ ID NO 22
<211> LENGTH: 14
<212> TYPE: PRT
<213> ORGANISM: Artificial Sequence
<220> FEATURE:
<223> OTHER INFORMATION: Synthetic Construct

<400> SEQUENCE: 22

Phe Asn Arg Gly Glu Cys Gly Gly Gly Leu Leu Gln Gly Gly
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic Construct

<400> SEQUENCE: 23

Phe Asn Arg Gly Glu Cys Leu Leu Gln Gly Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Gly Leu Leu Gln Gly Asp Ile Val Leu Thr
1               5                   10
```

```
<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Leu Leu Gln Ile Val Leu Thr
1               5

<210> SEQ ID NO 26
<211> LENGTH: 4
<212> TYPE: PRT
<213> ORGANISM: Artificial Sequence
<220> FEATURE:
<223> OTHER INFORMATION: Synthetic Construct

<400> SEQUENCE: 26

Arg Lys Gly Gly
1

<210> SEQ ID NO 27
<211> LENGTH: 5
<212> TYPE: PRT
<213> ORGANISM: Artificial Sequence
<220> FEATURE:
<223> OTHER INFORMATION: Synthetic Construct

<400> SEQUENCE: 27

Arg Gly Lys Gly Gly
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Construct

<400> SEQUENCE: 28

Arg Gly Ser Lys Gly Gly
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Arg Gly Ser Gly Lys Gly Gly
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30

Arg Gly Ser Gly Gly Lys Gly Gly
1               5
```

```
<210> SEQ ID NO 31
<211> LENGTH: 11
<212> TYPE: PRT
<213> ORGANISM: Artificial Sequence
<220> FEATURE:
<223> OTHER INFORMATION: Synthetic Construct

<400> SEQUENCE: 31

Lys Gly Ser Pro Leu Ala Gln Ser His Gly Gly
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Arg Gly Ser Pro Leu Ala Gln Ser His Gly Gly
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Synthetic Construct

<400> SEQUENCE: 33

Arg Gly Leu Leu Gln Gly Gly Gly
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

Arg Gly Leu Leu Gln Gly Gly
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic Construct

<400> SEQUENCE: 35

Arg Gly Leu Leu Gln Gly
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Arg Gly Leu Leu Gln
1               5
```

```
<210> SEQ ID NO 37
<211> LENGTH: 6
<212> TYPE: PRT
<213> ORGANISM: Artificial Sequence
<220> FEATURE:
<223> OTHER INFORMATION: Synthetic Construct

<400> SEQUENCE: 37

Arg Leu Leu Gln Gly Gly
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Lys Gly Leu Leu Gln Gly Gly Gly
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic Construct

<400> SEQUENCE: 39

Gln Val Gln Leu Lys Glu
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Construct

<400> SEQUENCE: 40

Val Gln Leu Lys Glu
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

Leu Gly Gly Gln Gly Gly Gly
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Construct

<400> SEQUENCE: 42

Gly Gly Gly Gln Gly Gly Leu
1               5
```

```
<210> SEQ ID NO 43
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa = Gly, Ala, Ser, Leu, Val, Phe, Tyr, Arg,
      Asn, or Glu

<400> SEQUENCE: 43

Gly Xaa Gly Gln Gly Gly Gly
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa = Gly, Ala, Ser, Leu, Val, Phe, Tyr, Arg,
      Asn, or Glu

<400> SEQUENCE: 44

Gly Gly Xaa Gln Gly Gly Gly
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa = Gly, Ala, Ser, Leu, Val, Phe, Tyr, Arg,
      Asn, or Glu

<400> SEQUENCE: 45

Gly Gly Gly Gln Xaa Gly Gly
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa = Gly, Ala, Ser, Leu, Val, Phe, Tyr, Arg,
      Asn, or Glu

<400> SEQUENCE: 46

Gly Gly Gly Gln Gly Xaa Gly
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 47

Leu Leu Gln Leu Leu Gln Gly Ala
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Construct

<400> SEQUENCE: 48

Leu Leu Gln Gly Ala
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic Construct

<400> SEQUENCE: 49

Leu Leu Gln Tyr Gln Gly Ala
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic Construct

<400> SEQUENCE: 50

Leu Leu Gln Gly Ser Gly
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Construct

<400> SEQUENCE: 51

Leu Leu Gln Tyr Gln Gly
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct

<400> SEQUENCE: 52

Leu Leu Gln Leu Leu Gln Gly
1               5

<210> SEQ ID NO 53
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 53

Ser Leu Leu Gln Gly
1               5

<210> SEQ ID NO 54
<211> LENGTH: 5
<212> TYPE: PRT
<213> ORGANISM: Artificial Sequence
<220> FEATURE:
<223> OTHER INFORMATION: Synthetic Construct

<400> SEQUENCE: 54

Leu Leu Gln Leu Gln
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct

<400> SEQUENCE: 55

Leu Leu Gln Leu Leu Gln
1               5

<210> SEQ ID NO 56
<211> LENGTH: 5
<212> TYPE: PRT
<213> ORGANISM: Artificial Sequence
<220> FEATURE:
<223> OTHER INFORMATION: Synthetic Construct

<400> SEQUENCE: 56

Leu Leu Gln Gly Arg
1               5

<210> SEQ ID NO 57
<211> LENGTH: 4
<212> TYPE: PRT
<213> ORGANISM: Artificial Sequence
<220> FEATURE:
<223> OTHER INFORMATION: Synthetic Construct

<400> SEQUENCE: 57

Pro Phe Thr Ser
1

<210> SEQ ID NO 58
<211> LENGTH: 4
<212> TYPE: PRT
<213> ORGANISM: Artificial Sequence
<220> FEATURE:
<223> OTHER INFORMATION: Synthetic Construct

<400> SEQUENCE: 58

Asp Asn Ser Lys
1

<210> SEQ ID NO 59
<211> LENGTH: 4
<212> TYPE: PRT
<213> ORGANISM: Artificial Sequence
<220> FEATURE:
<223> OTHER INFORMATION: Synthetic Construct
```

```
<400> SEQUENCE: 59

Ser Leu Gln Ser
1

<210> SEQ ID NO 60
<211> LENGTH: 4
<212> TYPE: PRT
<213> ORGANISM: Artificial Sequence
<220> FEATURE:
<223> OTHER INFORMATION: Synthetic Construct

<400> SEQUENCE: 60

Ser Ala Ser Thr
1

<210> SEQ ID NO 61
<211> LENGTH: 4
<212> TYPE: PRT
<213> ORGANISM: Artificial Sequence
<220> FEATURE:
<223> OTHER INFORMATION: Synthetic Construct

<400> SEQUENCE: 61

Asn Ser Gly Ala
1

<210> SEQ ID NO 62
<211> LENGTH: 4
<212> TYPE: PRT
<213> ORGANISM: Artificial Sequence
<220> FEATURE:
<223> OTHER INFORMATION: Synthetic Construct

<400> SEQUENCE: 62

Pro Ser Ser Ser
1

<210> SEQ ID NO 63
<211> LENGTH: 4
<212> TYPE: PRT
<213> ORGANISM: Artificial Sequence
<220> FEATURE:
<223> OTHER INFORMATION: Synthetic Construct

<400> SEQUENCE: 63

Lys Thr His Thr
1

<210> SEQ ID NO 64
<211> LENGTH: 4
<212> TYPE: PRT
<213> ORGANISM: Artificial Sequence
<220> FEATURE:
<223> OTHER INFORMATION: Synthetic Construct

<400> SEQUENCE: 64

Leu Met Ile Ser
1

<210> SEQ ID NO 65
<211> LENGTH: 4
<212> TYPE: PRT
<213> ORGANISM: Artificial Sequence
<220> FEATURE:
<223> OTHER INFORMATION: Synthetic Construct
```

```
<400> SEQUENCE: 65

Ser His Glu Asp
1

<210> SEQ ID NO 66
<211> LENGTH: 4
<212> TYPE: PRT
<213> ORGANISM: Artificial Sequence
<220> FEATURE:
<223> OTHER INFORMATION: Synthetic Construct

<400> SEQUENCE: 66

Glu Gln Tyr Asn
1

<210> SEQ ID NO 67
<211> LENGTH: 5
<212> TYPE: PRT
<213> ORGANISM: Artificial Sequence
<220> FEATURE:
<223> OTHER INFORMATION: Synthetic Construct

<400> SEQUENCE: 67

Glu Glu Gln Tyr Asn
1               5

<210> SEQ ID NO 68
<211> LENGTH: 4
<212> TYPE: PRT
<213> ORGANISM: Artificial Sequence
<220> FEATURE:
<223> OTHER INFORMATION: Synthetic Construct

<400> SEQUENCE: 68

Ser Asn Lys Ala
1

<210> SEQ ID NO 69
<211> LENGTH: 4
<212> TYPE: PRT
<213> ORGANISM: Artificial Sequence
<220> FEATURE:
<223> OTHER INFORMATION: Synthetic Construct

<400> SEQUENCE: 69

Glu Met Thr Lys
1

<210> SEQ ID NO 70
<211> LENGTH: 4
<212> TYPE: PRT
<213> ORGANISM: Artificial Sequence
<220> FEATURE:
<223> OTHER INFORMATION: Synthetic Construct

<400> SEQUENCE: 70

Ala Leu His Asn
1

<210> SEQ ID NO 71
<211> LENGTH: 4
<212> TYPE: PRT
<213> ORGANISM: Artificial Sequence
<220> FEATURE:
<223> OTHER INFORMATION: Synthetic Construct
```

```
<400> SEQUENCE: 71

Val Glu Ser Glu
1

<210> SEQ ID NO 72
<211> LENGTH: 4
<212> TYPE: PRT
<213> ORGANISM: Artificial Sequence
<220> FEATURE:
<223> OTHER INFORMATION: Synthetic Construct

<400> SEQUENCE: 72

Lys Arg Thr Val
1

<210> SEQ ID NO 73
<211> LENGTH: 4
<212> TYPE: PRT
<213> ORGANISM: Artificial Sequence
<220> FEATURE:
<223> OTHER INFORMATION: Synthetic Construct

<400> SEQUENCE: 73

Ser Asp Glu Gln
1

<210> SEQ ID NO 74
<211> LENGTH: 4
<212> TYPE: PRT
<213> ORGANISM: Artificial Sequence
<220> FEATURE:
<223> OTHER INFORMATION: Synthetic Construct

<400> SEQUENCE: 74

Gln Leu Lys Ser
1

<210> SEQ ID NO 75
<211> LENGTH: 4
<212> TYPE: PRT
<213> ORGANISM: Artificial Sequence
<220> FEATURE:
<223> OTHER INFORMATION: Synthetic Construct

<400> SEQUENCE: 75

Ala Leu Gln Ser
1

<210> SEQ ID NO 76
<211> LENGTH: 4
<212> TYPE: PRT
<213> ORGANISM: Artificial Sequence
<220> FEATURE:
<223> OTHER INFORMATION: Synthetic Construct

<400> SEQUENCE: 76

Asp Ser Lys Asp
1

<210> SEQ ID NO 77
<211> LENGTH: 4
<212> TYPE: PRT
<213> ORGANISM: Artificial Sequence
<220> FEATURE:
<223> OTHER INFORMATION: Synthetic Construct
```

```
<400> SEQUENCE: 77

Ser Lys Ala Asp
1

<210> SEQ ID NO 78
<211> LENGTH: 4
<212> TYPE: PRT
<213> ORGANISM: Artificial Sequence
<220> FEATURE:
<223> OTHER INFORMATION: Synthetic Construct

<400> SEQUENCE: 78

Tyr Glu Lys His
1

<210> SEQ ID NO 79
<211> LENGTH: 4
<212> TYPE: PRT
<213> ORGANISM: Artificial Sequence
<220> FEATURE:
<223> OTHER INFORMATION: Synthetic Construct

<400> SEQUENCE: 79

Gly Leu Ser Ser
1

<210> SEQ ID NO 80
<211> LENGTH: 4
<212> TYPE: PRT
<213> ORGANISM: Artificial Sequence
<220> FEATURE:
<223> OTHER INFORMATION: Synthetic Construct

<400> SEQUENCE: 80

Arg Gly Glu Cys
1

<210> SEQ ID NO 81
<211> LENGTH: 37
<212> TYPE: PRT
<213> ORGANISM: Artificial Sequence
<220> FEATURE:
<223> OTHER INFORMATION: Synthetic Construct

<400> SEQUENCE: 81

Asp Cys Leu Gly Trp Phe Lys Ser Cys Asp Pro Lys Asn Asp Lys Cys
1               5                   10                  15

Cys Lys Asn Tyr Thr Cys Ser Arg Arg Asp Arg Trp Cys Lys Tyr Asp
            20                  25                  30

Leu Leu Gln Gly Gly
        35

<210> SEQ ID NO 82
<211> LENGTH: 22
<212> TYPE: PRT
<213> ORGANISM: Artificial Sequence
<220> FEATURE:
<223> OTHER INFORMATION: Synthetic Construct

<400> SEQUENCE: 82

Gln Arg Cys Cys Asn Gly Arg Arg Gly Cys Ser Ser Arg Trp Cys Arg
1               5                   10                  15

Asp His Ser Arg Cys Cys
            20
```